US010736951B2

(12) United States Patent
Carlyon

(10) Patent No.: US 10,736,951 B2
(45) Date of Patent: Aug. 11, 2020

(54) OMPA AND ASP14 IN VACCINE COMPOSITIONS AND AS DIAGNOSTIC TARGETS

(71) Applicant: Virginia Commonwealth University, Richmond, VA (US)

(72) Inventor: Jason A. Carlyon, Richmond, VA (US)

(73) Assignee: Virginia Commonwealth University, Richmond, VA (US)

( * ) Notice: Subject to any disclaimer, the term of this patent is extended or adjusted under 35 U.S.C. 154(b) by 0 days.

(21) Appl. No.: 16/454,797

(22) Filed: Jun. 27, 2019

(65) Prior Publication Data

US 2019/0336592 A1 Nov. 7, 2019

Related U.S. Application Data

(62) Division of application No. 15/981,950, filed on May 17, 2018, now Pat. No. 10,376,570, which is a division of application No. 15/477,137, filed on Apr. 3, 2017, now Pat. No. 10,039,815, which is a division of application No. 14/967,687, filed on Dec. 14, 2015, now abandoned, which is a division of application No. 14/408,760, filed as application No. PCT/US2013/047325 on Jun. 24, 2013, now Pat. No. 9,248,174.

(60) Provisional application No. 61/665,223, filed on Jun. 27, 2012, provisional application No. 61/698,979, filed on Sep. 10, 2012.

(51) Int. Cl.

| | |
|---|---|
| ***A61K 39/02*** | (2006.01) |
| ***A61K 39/40*** | (2006.01) |
| ***C07K 16/12*** | (2006.01) |
| ***G01N 33/569*** | (2006.01) |
| *A61K 39/00* | (2006.01) |

(52) U.S. Cl.

CPC .......... *A61K 39/0233* (2013.01); *A61K 39/40* (2013.01); *C07K 16/1246* (2013.01); *G01N 33/56911* (2013.01); *G01N 33/56983* (2013.01); *A61K 2039/55566* (2013.01); *A61K 2039/6031* (2013.01); *A61K 2039/6081* (2013.01); *A61K 2039/70* (2013.01); *C07K 2317/76* (2013.01); *G01N 2333/195* (2013.01); *G01N 2333/29* (2013.01); *G01N 2469/10* (2013.01); *G01N 2800/42* (2013.01); *Y02A 50/403* (2018.01)

(58) Field of Classification Search

None

See application file for complete search history.

(56) References Cited

U.S. PATENT DOCUMENTS

| | | | | |
|---|---|---|---|---|
| 9,248,174 | B2 * | 2/2016 | Carlyon | A61K 39/0233 |
| 10,039,815 | B2 * | 8/2018 | Carlyon | A61K 39/40 |
| 10,376,570 | B2 * | 8/2019 | Carlyon | C07K 16/1246 |

* cited by examiner

*Primary Examiner* — Padmavathi Baskar

(74) *Attorney, Agent, or Firm* — W&C IP

(57) ABSTRACT

*Anaplasma phagocytophilum* surface proteins Asp14 and OmpA and homologous genes from Anaplasmatacaea family members are used in compositions suitable for vaccines to treat or prevent infections caused by tick-born bacteria of the Anaplasmatacaea family. Asp14 and/or OmpA proteins or peptide fragments may be used in combination with other Anaplasmatacaea surface proteins to elicit an immune response. Furthermore, antibodies to Asp14 and/or OmpA proteins can be used in diagnostic methods to determine whether an individual has contracted an Anaplasmatacaea infection. Because of the conserved invasin domains in the surface proteins, a wide range of Anaplasmatacaea infections may be diagnosed, treated or prevented using compositions of the invention.

3 Claims, 21 Drawing Sheets

Specification includes a Sequence Listing.

```
                          30        40        50        60        70        80        90        100
OmpA        --PDSNVGVGRHDLGSHRSVAFAKKVEKVYFDIGKYDLKGPGKKVILELVEQLRQDDSMYLVVIGHADATGTEEYSLALGEK
AM854       LFSKEKVGMDIVGVPFS-----AGRVEKVYFDFNKYEIKGSGKKVLLGLVERMKADKRSTLLIIGHTDSRGTEEYNLALGER
ACIS_00486  --NKEKVNIDIGGVPLS-----AGRVEKVYFDFNKYEIKGSGKKVLLGLVERMKADKMSTLLIVGHTDSRGTEEYNLALGKR
ECH_0462    ---------NVDHVFSN-----TKTIEKIYFGFGKATIEDSDKTILEKVMQKAEEYPDTNIIIVGHTDTRGTDEYNLELGEQ
Ecaj_0563   -TTDHVPLVNTDHVFSN-----MKTIEKIYFDFGKATIGDSDKAILEKVIQKAQKDTNTNIVIVGHTDTRGTDEYNLELGEQ
Erum_5620   -NSKHVPLVNVHNLFSN-----IKAIDKVYFDLDKTVIKDSDKVLLEKLVQKAQEDPTTDIIIVGHTDTRGTDEYNLALGEQ

                   110       120       130       140       150       160                 170
OmpA        RANAVKQFIIGCDKSLAPRVTTQSRGKAEPEVLVYSTDAQEVEKANAQNRRAVIVVEFAHIPRS-------------GVADM
AM854       RANAVKEFIIGCDRSLSPRISTQSRGKAEPEVLVYSSDFKFAEKAHAQNRRVVLIVECQHSVSPKKKMAIKWPFSFGRSAAK
ACIS_00486  RANAVKEFILGCDRSLSPRISTQSRGKAEPEILVYSSDFKEAEKAHAQNRRVVLIMECQHAASPKKARVSRWPFSFGRSSAT
ECH_0462    RANAVKDFILERNKSLEDRIIIESKGKSEPAVLVYSNNPEEAEYAHTKNRRVVITLTDNLI--------------Y-KAKSS
Ecaj_0563   RANAVKDFIIEHDKSLENRITVQSKGKSEPAVLVYSSNPEEAEHAHAKNRRVVITLTDN----------------------
Erum_5620   RANAVRDFIISCDKSLEKRITVRSKGKSEPAILVYSNNPKEAEDAHAKNRRVVITLVNNSTSTDNKVPTTTTPFNE-EAHNT

                   180       190       200
OmpA        HAPVASSITSENSNASAEG-----ED-MEASEFSSAIAN                          SEQ ID NO:10
AM854       QDDVGSSEVSDENPVDDSSEGIASEEAAPEEGVVSEEAAEEAPEVAQDSSAGVVAPE        SEQ ID NO:67
ACIS_00486  QQDNGGGTVAAGSPGEDAP----AEVVEPEE---TQEAGE                         SEQ ID NO:68
ECH_0462    DKDPSSNKTEQ                                                      SEQ ID NO:69
Ecaj_0563   -----GNKTSQ                                                      SEQ ID NO:70
Erum_5620   ISKDQENNTQQQAKSDNINN-INTQQKLEQDNNNTPEVN                          SEQ ID NO:71
```

Figure 6A

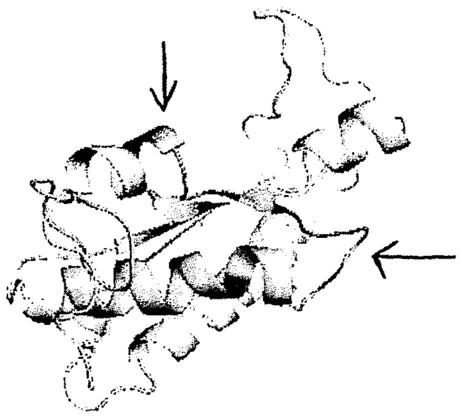

Figure 6B

```
                        10        20        30        40        50        60        70        80
                         |         |         |         |         |         |         |         |
Asp14        MIPLAPWKSISVVYMSGSDEYKEIIKQCIGSVKEVFEEGR-FDDVVASIMRMQEKVLASSMQQDDTGTVGQIESGEGSGARL
AM936        --------------MSGEDEYKEIIRQCIGSVKEVFEEGR-FDDVVASIMRMQEKVLASSMKDGDP--VGQIAA-DGVGNEL
ACIS_00403   --------------MSGEDEYKEIIRQCIGSVKEVFEEGR-FDDVVASIMRMQEKVLASSMKDGDP--VGQIAA-DGVGNEL
ECH_0377     ---------------MAEEDYKGVIKQYIDTVKEIVGDSKTFDQMFESVVRIQERVMEANAQNNED----GVIDNGDQVKRI
Ecaj_0636    ---------------MADIEYKGVIQQYINTVKEIVSDSKTFDQMFESVVKIQERVMEANAQN----------DDGSQVKRI
Erum6320     ----------MCSSFMADEDYKGVIKQYIDTVKEIVGDSKTFDQMFESVVKIQERVMEASAQNEAN---GALVEGDSKMKRI
                              ..::   : :   .:  :..:.:   ::.  ::::  : : :. ::          .    .:

                       90        100       110                 120
                        |         |         |                   |
                                  ******************         *******
Asp14        SDEQVQQLMNSIREEFKDDIRAIKRRIEKLERAVYG----------------ANTPKES---------   SEQ ID NO:01
AM936        YDRIADRLEERVSQKISEDLRIIKKRLLRLERVVLGGGSVSGD-AAAHQVSGNQPSQQNSSAAAEGG   SEQ ID NO:13
ACIS_00403   YDRIADRLEERVSQKISEDLRIIKKRLLRLERVVLGGGSVSGDAAAAHQVSGNQPSQQNSSAAAEGG   SEQ ID NO:15
ECH_0377     GSSTSESISNTEYKELMEELKVIKKRILRLERKILKP-----------------KEEV---------   SEQ ID NO:19
Ecaj_0636    GSSTSDSISDSQYKELIEELKVIKKRLLRLEHKVLKP-----------------KEGA---------   SEQ ID NO:23
Erum6320     R-SADDSIAYTQSQELLEELKVLKKRIARLERHVFKSN----------------KTEV---------   SEQ ID NO:72
                 : :      ::: :: : : : : :  : :
```

FIGURE 11

```
                           34-                      54-           62- 67-    72- 77-
                            39                       59           69  68     73  78   80
                         30    40                 50           60         70
         **********************************************************************************
SEQ ID NO:10 OmpA        --PDSNVGVGRHDLGSHRSVAFANKVE V DIG YDLKGPG KVILELVEQL RQDDSMYJ
SEQ ID NO:32 AM854       LFSKEKVGMDIVGVPFS------AGRVE V DEN VEIKGSG KVLLGLVERMKADKRST
SEQ ID NO:34 ACIS_00486  NKEKVNIDIGGVPLS-------AGRVE V DEN VEIKGSG KVLLGLVERMKADKMST
SEQ ID NO:40 ECH_0462    -------NVDHVFSN--------TKTIE I GRG ATIEDSD TILEKVMQKAEEYPDEN
SEQ ID NO:46 ECaj_0563   -TTDHVPLVNTDHVFSN------MKTIE I DEG ATIGDSD ALLEKVIQKAQKDTNTN
SEQ ID NO:52 Erum5620    -NSKHVPLVNVHNLFSN------IKAID V DLD TVIKDSD VLLEKLVQKAQEDPTTD
                         .             .          ::       ::   :::         ::          .
```

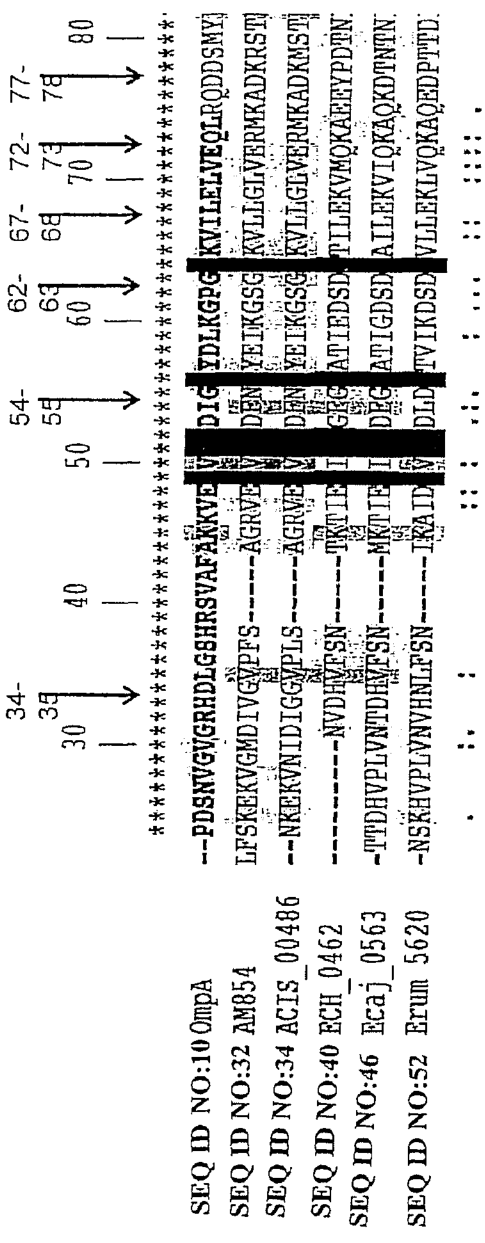

FIGURE 14

SEQUENCE LISTING

```
<160> NUMBER OF SEQ ID NOS: 72

<210> SEQ ID NO 1
<211> LENGTH: 124
<212> TYPE: PRT
<213> ORGANISM: Anaplasma phagocytophilum

<400> SEQUENCE: 1

Met Ile Pro Leu Ala Pro Trp Lys Ser Ile Ser Val Val Tyr Met Ser
1               5                   10                  15

Gly Ser Asp Glu Tyr Lys Glu Ile Ile Lys Gln Cys Ile Gly Ser Val
            20                  25                  30

Lys Glu Val Phe Gly Glu Gly Arg Phe Asp Asp Val Val Ala Ser Ile
        35                  40                  45

Met Lys Met Gln Glu Lys Val Leu Ala Ser Ser Met Gln Gln Asp Asp
    50                  55                  60

Thr Gly Thr Val Gly Gln Ile Glu Ser Gly Glu Gly Ser Gly Ala Arg
65                  70                  75                  80

Leu Ser Asp Glu Gln Val Gln Gln Leu Met Asn Ser Ile Arg Glu Glu
                85                  90                  95

Phe Lys Asp Asp Leu Arg Ala Ile Lys Arg Arg Ile Leu Lys Leu Glu
            100                 105                 110

Arg Ala Val Tyr Gly Ala Asn Thr Pro Lys Glu Ser
        115                 120


<210> SEQ ID NO 2
<211> LENGTH: 24
<212> TYPE: PRT
<213> ORGANISM: Anaplasma phagocytophilum

<400> SEQUENCE: 2

Leu Arg Ala Ile Lys Arg Arg Ile Leu Lys Leu Glu Arg Ala Val Tyr
1               5                   10                  15

Gly Ala Asn Thr Pro Lys Glu Ser
            20


<210> SEQ ID NO 3
<211> LENGTH: 12
<212> TYPE: PRT
<213> ORGANISM: Anaplasma phagocytophilum

<400> SEQUENCE: 3

Arg Ala Val Tyr Gly Ala Asn Thr Pro Lys Glu Ser
1               5                   10


<210> SEQ ID NO 4
<211> LENGTH: 205
<212> TYPE: PRT
<213> ORGANISM: Anaplasma phagocytophilum

<400> SEQUENCE: 4

Met Leu Arg Arg Ser Ser Phe Phe Cys Leu Leu Ala Leu Leu Ser Val
1               5                   10                  15

Thr Ser Cys Gly Thr Leu Leu Pro Asp Ser Asn Val Gly Val Gly Arg
            20                  25                  30
```

-continued

```
His Asp Leu Gly Ser His Arg Ser Val Ala Phe Ala Lys Lys Val Glu
        35                  40                  45

Lys Val Tyr Phe Asp Ile Gly Lys Tyr Asp Leu Lys Gly Pro Gly Lys
    50                  55                  60

Lys Val Ile Leu Glu Leu Val Glu Gln Leu Arg Gln Asp Asp Ser Met
65                  70                  75                  80

Tyr Leu Val Val Ile Gly His Ala Asp Ala Thr Gly Thr Glu Glu Tyr
                85                  90                  95

Ser Leu Ala Leu Gly Glu Lys Arg Ala Asn Ala Val Lys Gln Phe Ile
            100                 105                 110

Ile Gly Cys Asp Lys Ser Leu Ala Pro Arg Val Thr Thr Gln Ser Arg
        115                 120                 125

Gly Lys Ala Glu Pro Glu Val Leu Val Tyr Ser Thr Asp Ala Gln Glu
    130                 135                 140

Val Glu Lys Ala Asn Ala Gln Asn Arg Arg Ala Val Ile Val Val Glu
145                 150                 155                 160

Phe Ala His Ile Pro Arg Ser Gly Val Ala Asp Met His Ala Pro Val
                165                 170                 175

Ala Ser Ser Ile Thr Ser Glu Asn Ser Asn Ala Ser Ala Glu Gly Glu
            180                 185                 190

Asp Met Glu Ala Ser Glu Phe Ser Ser Ala Ile Ala Asn
        195                 200                 205
```

<210> SEQ ID NO 5
<211> LENGTH: 57
<212> TYPE: PRT
<213> ORGANISM: Anaplasma phagocytophilum

<400> SEQUENCE: 5

```
Cys Gly Thr Leu Leu Pro Asp Ser Asn Val Gly Val Gly Arg His Asp
1               5                   10                  15

Leu Gly Ser His Arg Ser Val Ala Phe Ala Lys Lys Val Glu Lys Val
            20                  25                  30

Tyr Phe Asp Ile Gly Lys Tyr Asp Leu Lys Gly Pro Gly Lys Lys Val
        35                  40                  45

Ile Leu Glu Leu Val Glu Gln Leu Arg
    50                  55
```

<210> SEQ ID NO 6
<211> LENGTH: 16
<212> TYPE: PRT
<213> ORGANISM: Anaplasma phagocytophilum

<400> SEQUENCE: 6

```
Leu Lys Gly Pro Gly Lys Lys Val Ile Leu Glu Leu Val Glu Gln Leu
1               5                   10                  15
```

<210> SEQ ID NO 7
<211> LENGTH: 9
<212> TYPE: PRT
<213> ORGANISM: Anaplasma phagocytophilum

<400> SEQUENCE: 7

```
Glu Lys Val Tyr Phe Asp Ile Gly Lys
1               5
```

<210> SEQ ID NO 8
<211> LENGTH: 16
<212> TYPE: PRT

<213> ORGANISM: Anaplasma phagocytophilum

<400> SEQUENCE: 8

```
Gly His Ala Asp Ala Thr Gly Thr Glu Glu Tyr Ser Leu Ala Leu Gly
1               5                   10                  15
```

<210> SEQ ID NO 9
<211> LENGTH: 21
<212> TYPE: PRT
<213> ORGANISM: Anaplasma phagocytophilum

<400> SEQUENCE: 9

```
Leu Val Tyr Ser Thr Asp Ala Gln Glu Val Glu Lys Ala Asn Ala Gln
1               5                   10                  15

Asn Arg Arg Ala Val
            20
```

<210> SEQ ID NO 10
<211> LENGTH: 149
<212> TYPE: PRT
<213> ORGANISM: Anaplasma phagocytophilum

<400> SEQUENCE: 10

```
Pro Asp Ser Asn Val Gly Val Gly Arg His Asp Leu Gly Ser His Arg
1               5                   10                  15

Ser Val Ala Phe Ala Lys Lys Val Glu Lys Val Tyr Phe Asp Ile Gly
            20                  25                  30

Lys Tyr Asp Leu Lys Gly Pro Gly Lys Lys Val Ile Leu Glu Leu Val
        35                  40                  45

Glu Gln Leu Arg Gln Asp Asp Ser Met Tyr Leu Val Val Ile Gly His
    50                  55                  60

Ala Asp Ala Thr Gly Thr Glu Glu Tyr Ser Leu Ala Leu Gly Glu Lys
65                  70                  75                  80

Arg Ala Asn Ala Val Lys Gln Phe Ile Ile Gly Cys Asp Lys Ser Leu
                85                  90                  95

Ala Pro Arg Val Thr Thr Gln Ser Arg Gly Lys Ala Glu Pro Glu Val
            100                 105                 110

Leu Val Tyr Ser Thr Asp Ala Gln Glu Val Glu Lys Ala Asn Ala Gln
        115                 120                 125

Asn Arg Arg Ala Val Ile Val Val Glu Phe Ala His Ile Pro Arg Ser
    130                 135                 140

Gly Val Ala Asp Met
145
```

<210> SEQ ID NO 11
<211> LENGTH: 12
<212> TYPE: PRT
<213> ORGANISM: Anaplasma phagocytophilum

<400> SEQUENCE: 11

```
Leu Arg Ala Ile Lys Arg Arg Ile Leu Lys Leu Glu
1               5                   10
```

<210> SEQ ID NO 12
<211> LENGTH: 42
<212> TYPE: PRT
<213> ORGANISM: Anaplasma phagocytophilum

<400> SEQUENCE: 12

```
Asp Glu Tyr Lys Glu Ile Ile Lys Gln Cys Ile Gly Ser Val Lys Glu
```

1 5 10 15

Val Phe Gly Glu Gly Arg Phe Asp Asp Val Val Ala Ser Ile Met Lys
20 25 30

Met Gln Glu Lys Val Leu Ala Ser Ser Met
35 40

<210> SEQ ID NO 13
<211> LENGTH: 130
<212> TYPE: PRT
<213> ORGANISM: Anaplasma marginale

<400> SEQUENCE: 13

Met Ser Gly Glu Asp Glu Tyr Lys Glu Ile Ile Arg Gln Cys Ile Gly
1 5 10 15

Ser Val Lys Glu Val Phe Gly Glu Gly Arg Phe Asp Asp Val Val Ala
20 25 30

Ser Ile Met Lys Met Gln Glu Lys Val Leu Ala Ser Ser Met Lys Asp
35 40 45

Gly Asp Pro Val Gly Gln Ile Ala Ala Asp Gly Val Gly Asn Glu Leu
50 55 60

Tyr Asp Arg Ile Ala Asp Arg Leu Glu Glu Arg Val Ser Gln Lys Ile
65 70 75 80

Ser Glu Asp Leu Arg Ile Ile Lys Lys Arg Leu Leu Arg Leu Glu Arg
85 90 95

Val Val Leu Gly Gly Gly Ser Val Ser Gly Asp Ala Ala Ala His Gln
100 105 110

Val Ser Gly Asn Gln Pro Ser Gln Gln Asn Ser Ser Ala Ala Ala Glu
115 120 125

Gly Gly
130

<210> SEQ ID NO 14
<211> LENGTH: 32
<212> TYPE: PRT
<213> ORGANISM: Anaplasma marginale

<400> SEQUENCE: 14

Leu Gly Gly Gly Ser Val Ser Gly Asp Ala Ala Ala His Gln Val Ser
1 5 10 15

Gly Asn Gln Pro Ser Gln Gln Asn Ser Ser Ala Ala Ala Glu Gly Gly
20 25 30

<210> SEQ ID NO 15
<211> LENGTH: 131
<212> TYPE: PRT
<213> ORGANISM: Anaplasma marginale, subspecies Centrale

<400> SEQUENCE: 15

Met Ser Gly Glu Asp Glu Tyr Lys Glu Ile Ile Arg Gln Cys Ile Gly
1 5 10 15

Ser Val Lys Glu Val Phe Gly Glu Gly Arg Phe Asp Asp Val Val Ala
20 25 30

Ser Ile Met Lys Met Gln Glu Lys Val Leu Ala Ser Ser Met Lys Asp
35 40 45

Gly Asp Pro Val Gly Gln Ile Ala Ala Asp Gly Val Gly Asn Glu Leu
50 55 60

Tyr Asp Arg Ile Ala Asp Arg Leu Glu Glu Arg Val Ser Gln Lys Ile
65 70 75 80

Ser Glu Asp Leu Arg Ile Ile Lys Lys Arg Leu Leu Arg Leu Glu Arg
85 90 95

Val Val Leu Gly Gly Gly Ser Val Ser Gly Asp Ala Ala Ala Ala His
100 105 110

Gln Val Ser Gly Asn Gln Pro Ser Gln Gln Asn Ser Ser Ala Ala Ala
115 120 125

Glu Gly Gly
130

<210> SEQ ID NO 16
<211> LENGTH: 33
<212> TYPE: PRT
<213> ORGANISM: Anaplasma marginale, subspecie Centrale

<400> SEQUENCE: 16

Leu Gly Gly Gly Ser Val Ser Gly Asp Ala Ala Ala Ala His Gln Val
1 5 10 15

Ser Gly Asn Gln Pro Ser Gln Gln Asn Ser Ser Ala Ala Ala Glu Gly
20 25 30

Gly

<210> SEQ ID NO 17
<211> LENGTH: 46
<212> TYPE: PRT
<213> ORGANISM: Anaplasma marginale and A. marginale subspecies Centrale

<400> SEQUENCE: 17

Met Ser Gly Glu Asp Glu Tyr Lys Glu Ile Ile Arg Gln Cys Ile Gly
1 5 10 15

Ser Val Lys Glu Val Phe Gly Glu Gly Arg Phe Asp Asp Val Val Ala
20 25 30

Ser Ile Met Lys Met Gln Glu Lys Val Leu Ala Ser Ser Met
35 40 45

<210> SEQ ID NO 18
<211> LENGTH: 16
<212> TYPE: PRT
<213> ORGANISM: Anaplasma marginale and A. marginale subspecies Centrale

<400> SEQUENCE: 18

Asp Leu Arg Ile Ile Lys Lys Arg Leu Leu Arg Leu Glu Arg Val Val
1 5 10 15

<210> SEQ ID NO 19
<211> LENGTH: 104
<212> TYPE: PRT
<213> ORGANISM: Ehrlichia chaffeensis

<400> SEQUENCE: 19

Met Ala Glu Asp Asp Tyr Lys Gly Val Ile Lys Gln Tyr Ile Asp Thr
1 5 10 15

Val Lys Glu Ile Val Gly Asp Ser Lys Thr Phe Asp Gln Met Phe Glu
20 25 30

Ser Val Val Arg Ile Gln Glu Arg Val Met Ala Ala Asn Ala Gln Asn
35 40 45

Asn Glu Asp Gly Val Ile Asp Asn Gly Asp Gln Val Lys Arg Ile Gly
50 55 60

Ser Ser Thr Ser Glu Ser Ile Ser Asn Thr Glu Tyr Lys Glu Leu Met
65 70 75 80

```
Glu Glu Leu Lys Val Ile Lys Lys Arg Ile Leu Arg Leu Glu Arg Lys
                85                  90                  95

Ile Leu Lys Pro Lys Glu Glu Val
            100


<210> SEQ ID NO 20
<211> LENGTH: 42
<212> TYPE: PRT
<213> ORGANISM: Ehrlichia chaffeensis

<400> SEQUENCE: 20

Met Ala Glu Asp Asp Tyr Lys Gly Val Ile Lys Gln Tyr Ile Asp Thr
1               5                   10                  15

Val Lys Glu Ile Val Gly Asp Ser Lys Thr Phe Asp Gln Met Phe Glu
            20                  25                  30

Ser Val Val Arg Ile Gln Glu Arg Val Met
        35                  40


<210> SEQ ID NO 21
<211> LENGTH: 13
<212> TYPE: PRT
<213> ORGANISM: Ehrlichia chaffeensis

<400> SEQUENCE: 21

Glu Leu Lys Val Ile Lys Lys Arg Ile Leu Arg Leu Glu
1               5                   10


<210> SEQ ID NO 22
<211> LENGTH: 10
<212> TYPE: PRT
<213> ORGANISM: Ehrlichia chaffeensis

<400> SEQUENCE: 22

Arg Lys Ile Leu Lys Pro Lys Glu Glu Val
1               5                   10


<210> SEQ ID NO 23
<211> LENGTH: 98
<212> TYPE: PRT
<213> ORGANISM: Ehrlichia canis

<400> SEQUENCE: 23

Met Ala Asp Asp Glu Tyr Lys Gly Val Ile Gln Gln Tyr Ile Asn Thr
1               5                   10                  15

Val Lys Glu Ile Val Ser Asp Ser Lys Thr Phe Asp Gln Met Phe Glu
            20                  25                  30

Ser Val Val Lys Ile Gln Glu Arg Val Met Glu Ala Asn Ala Gln Asn
        35                  40                  45

Asp Asp Gly Ser Gln Val Lys Arg Ile Gly Ser Ser Thr Ser Asp Ser
    50                  55                  60

Ile Ser Asp Ser Gln Tyr Lys Glu Leu Ile Glu Glu Leu Lys Val Ile
65                  70                  75                  80

Lys Lys Arg Leu Leu Arg Leu Glu His Lys Val Leu Lys Pro Lys Glu
                85                  90                  95

Gly Ala


<210> SEQ ID NO 24
<211> LENGTH: 42
<212> TYPE: PRT
<213> ORGANISM: Ehrlichia canis
```

<400> SEQUENCE: 24

```
Met Ala Asp Asp Glu Tyr Lys Gly Val Ile Gln Gln Tyr Ile Asn Thr
1               5                   10                  15

Val Lys Glu Ile Val Ser Asp Ser Lys Thr Phe Asp Gln Met Phe Glu
            20                  25                  30

Ser Val Val Lys Ile Gln Glu Arg Val Met
        35                  40
```

<210> SEQ ID NO 25
<211> LENGTH: 13
<212> TYPE: PRT
<213> ORGANISM: Ehrlichia canis

<400> SEQUENCE: 25

```
Glu Leu Lys Val Ile Lys Lys Arg Leu Leu Arg Leu Glu
1               5                   10
```

<210> SEQ ID NO 26
<211> LENGTH: 10
<212> TYPE: PRT
<213> ORGANISM: Ehrlichia canis

<400> SEQUENCE: 26

```
His Lys Val Leu Lys Pro Lys Glu Gly Ala
1               5                   10
```

<210> SEQ ID NO 27
<211> LENGTH: 105
<212> TYPE: PRT
<213> ORGANISM: Ehrlichia ruminantium

<400> SEQUENCE: 27

```
Met Ala Asp Glu Asp Tyr Lys Gly Val Ile Lys Gln Tyr Ile Asp Thr
1               5                   10                  15

Val Lys Glu Ile Val Gly Asp Ser Lys Thr Phe Asp Gln Met Phe Glu
            20                  25                  30

Ser Val Val Lys Ile Gln Glu Arg Val Met Ala Ala Ser Ala Gln Asn
        35                  40                  45

Glu Ala Asn Gly Ala Leu Val Glu Gly Asp Ser Lys Met Lys Arg Ile
    50                  55                  60

Arg Ser Ala Asp Asp Ser Ile Ala Tyr Thr Gln Ser Gln Glu Leu Leu
65                  70                  75                  80

Glu Glu Leu Lys Val Leu Lys Lys Arg Ile Ala Arg Leu Glu Arg His
                85                  90                  95

Val Phe Lys Ser Asn Lys Thr Glu Ala
            100                 105
```

<210> SEQ ID NO 28
<211> LENGTH: 42
<212> TYPE: PRT
<213> ORGANISM: Ehrlichia ruminantium

<400> SEQUENCE: 28

```
Met Ala Asp Glu Asp Tyr Lys Gly Val Ile Lys Gln Tyr Ile Asp Thr
1               5                   10                  15

Val Lys Glu Ile Val Gly Asp Ser Lys Thr Phe Asp Gln Met Phe Glu
            20                  25                  30

Ser Val Val Lys Ile Gln Glu Arg Val Met
        35                  40
```

<210> SEQ ID NO 29
<211> LENGTH: 13
<212> TYPE: PRT
<213> ORGANISM: Ehrlichia ruminantium

<400> SEQUENCE: 29

```
Glu Leu Lys Val Leu Lys Lys Arg Ile Ala Arg Leu Glu
1               5                   10
```

<210> SEQ ID NO 30
<211> LENGTH: 11
<212> TYPE: PRT
<213> ORGANISM: Ehrlichia ruminantium

<400> SEQUENCE: 30

```
Arg His Val Phe Lys Ser Asn Lys Thr Glu Ala
1               5                   10
```

<210> SEQ ID NO 31
<211> LENGTH: 236
<212> TYPE: PRT
<213> ORGANISM: Anaplasma marginale

<400> SEQUENCE: 31

```
Met Leu His Arg Trp Leu Ala Leu Cys Phe Leu Ala Ser Phe Ala Val
1               5                   10                  15

Thr Gly Cys Gly Leu Phe Ser Lys Glu Lys Val Gly Met Asp Ile Val
            20                  25                  30

Gly Val Pro Phe Ser Ala Gly Arg Val Glu Lys Val Tyr Phe Asp Phe
        35                  40                  45

Asn Lys Tyr Glu Ile Lys Gly Ser Gly Lys Lys Val Leu Leu Gly Leu
    50                  55                  60

Val Glu Arg Met Lys Ala Asp Lys Arg Ser Thr Leu Leu Ile Ile Gly
65                  70                  75                  80

His Thr Asp Ser Arg Gly Thr Glu Glu Tyr Asn Leu Ala Leu Gly Glu
                85                  90                  95

Arg Arg Ala Asn Ala Val Lys Glu Phe Ile Leu Gly Cys Asp Arg Ser
            100                 105                 110

Leu Ser Pro Arg Ile Ser Thr Gln Ser Arg Gly Lys Ala Glu Pro Glu
        115                 120                 125

Val Leu Val Tyr Ser Ser Asp Phe Lys Glu Ala Glu Lys Ala His Ala
    130                 135                 140

Gln Asn Arg Arg Val Val Leu Ile Val Glu Cys Gln His Ser Val Ser
145                 150                 155                 160

Pro Lys Lys Lys Met Ala Ile Lys Trp Pro Phe Ser Phe Gly Arg Ser
                165                 170                 175

Ala Ala Lys Gln Asp Asp Val Gly Ser Ser Glu Val Ser Asp Glu Asn
            180                 185                 190

Pro Val Asp Asp Ser Ser Glu Gly Ile Ala Ser Glu Glu Ala Ala Pro
        195                 200                 205

Glu Glu Gly Val Val Ser Glu Glu Ala Ala Glu Glu Ala Pro Glu Val
    210                 215                 220

Ala Gln Asp Ser Ser Ala Gly Val Val Ala Pro Glu
225                 230                 235
```

<210> SEQ ID NO 32
<211> LENGTH: 59

<212> TYPE: PRT
<213> ORGANISM: Anaplasma marginale

<400> SEQUENCE: 32

```
Leu Phe Ser Lys Glu Lys Val Gly Met Asp Ile Val Gly Val Pro Phe
1               5                   10                  15

Ser Ala Gly Arg Val Glu Lys Val Tyr Phe Asp Phe Asn Lys Tyr Glu
            20                  25                  30

Ile Lys Gly Ser Gly Lys Lys Val Leu Leu Gly Leu Val Glu Arg Met
        35                  40                  45

Lys Ala Asp Lys Arg Ser Thr Leu Leu Ile Ile
    50                  55
```

<210> SEQ ID NO 33
<211> LENGTH: 212
<212> TYPE: PRT
<213> ORGANISM: Anaplasma marginale, subspecies Centrale

<400> SEQUENCE: 33

```
Met Leu His Arg Trp Leu Ala Leu Cys Leu Leu Ala Ser Leu Ala Val
1               5                   10                  15

Thr Gly Cys Glu Leu Phe Asn Lys Glu Lys Val Asn Ile Asp Ile Gly
            20                  25                  30

Gly Val Pro Leu Ser Ala Gly Arg Val Glu Lys Val Tyr Phe Asp Phe
        35                  40                  45

Asn Lys Tyr Glu Ile Lys Gly Ser Gly Lys Lys Val Leu Leu Gly Leu
    50                  55                  60

Val Glu Arg Met Lys Ala Asp Lys Met Ser Thr Leu Leu Ile Val Gly
65                  70                  75                  80

His Thr Asp Ser Arg Gly Thr Glu Glu Tyr Asn Leu Ala Leu Gly Glu
                85                  90                  95

Arg Arg Ala Asn Ala Val Lys Glu Phe Ile Leu Gly Cys Asp Arg Ser
            100                 105                 110

Leu Ser Pro Arg Ile Ser Thr Gln Ser Arg Gly Lys Ala Glu Pro Glu
        115                 120                 125

Ile Leu Val Tyr Ser Ser Asp Phe Lys Glu Ala Glu Lys Ala His Ala
    130                 135                 140

Gln Asn Arg Arg Val Val Leu Ile Met Glu Cys Gln His Ala Ala Ser
145                 150                 155                 160

Pro Lys Lys Ala Arg Val Ser Arg Trp Pro Phe Ser Phe Gly Arg Ser
                165                 170                 175

Ser Ala Thr Gln Gln Asp Asn Gly Gly Gly Thr Val Ala Ala Gly Ser
            180                 185                 190

Pro Gly Glu Asp Ala Pro Ala Glu Val Val Glu Pro Glu Glu Thr Gln
        195                 200                 205

Glu Ala Gly Glu
    210
```

<210> SEQ ID NO 34
<211> LENGTH: 59
<212> TYPE: PRT
<213> ORGANISM: Anaplasma marginale, subspecies Centrale

<400> SEQUENCE: 34

```
Leu Phe Asn Lys Glu Lys Val Asn Ile Asp Ile Gly Gly Val Pro Leu
1               5                   10                  15

Ser Ala Gly Arg Val Glu Lys Val Tyr Phe Asp Phe Asn Lys Tyr Glu
```

```
            20                  25                  30

Ile Lys Gly Ser Gly Lys Lys Val Leu Leu Gly Leu Val Glu Arg Met
        35                  40                  45

Lys Ala Asp Lys Met Ser Thr Leu Leu Ile Val
    50                  55


<210> SEQ ID NO 35
<211> LENGTH: 34
<212> TYPE: PRT
<213> ORGANISM: Anaplasma marginale and A. marginale subspecies Centrale

<400> SEQUENCE: 35

Ala Gly Arg Val Glu Lys Val Tyr Phe Asp Phe Asn Lys Tyr Glu Ile
1               5                   10                  15

Lys Gly Ser Gly Lys Lys Val Leu Leu Gly Leu Val Glu Arg Met Lys
            20                  25                  30

Ala Asp


<210> SEQ ID NO 36
<211> LENGTH: 16
<212> TYPE: PRT
<213> ORGANISM: Anaplasma marginale and A. marginale subspecies Centrale

<400> SEQUENCE: 36

Gly His Thr Asp Ser Arg Gly Thr Glu Glu Tyr Asn Leu Ala Leu Gly
1               5                   10                  15


<210> SEQ ID NO 37
<211> LENGTH: 30
<212> TYPE: PRT
<213> ORGANISM: Anaplasma marginale and A. marginale subspecies Centrale

<400> SEQUENCE: 37

Arg Arg Ala Asn Ala Val Lys Glu Phe Ile Leu Gly Cys Asp Arg Ser
1               5                   10                  15

Leu Ser Pro Arg Ile Ser Thr Gln Ser Arg Gly Lys Ala Glu
            20                  25                  30


<210> SEQ ID NO 38
<211> LENGTH: 23
<212> TYPE: PRT
<213> ORGANISM: Anaplasma marginale and A. marginale subspecies Centrale

<400> SEQUENCE: 38

Leu Val Tyr Ser Ser Asp Phe Lys Glu Ala Glu Lys Ala His Ala Gln
1               5                   10                  15

Asn Arg Arg Val Val Leu Ile
            20


<210> SEQ ID NO 39
<211> LENGTH: 175
<212> TYPE: PRT
<213> ORGANISM: Ehrlichia chaffeensis

<400> SEQUENCE: 39

Met Lys His Lys Leu Val Phe Ile Lys Phe Met Leu Leu Cys Leu Ile
1               5                   10                  15

Leu Ser Ser Cys Lys Thr Thr Asp His Val Pro Leu Val Asn Val Asp
            20                  25                  30

His Val Phe Ser Asn Thr Lys Thr Ile Glu Lys Ile Tyr Phe Gly Phe
        35                  40                  45
```

```
Gly Lys Ala Thr Ile Glu Asp Ser Asp Lys Thr Ile Leu Glu Lys Val
    50                  55                  60

Met Gln Lys Ala Glu Glu Tyr Pro Asp Thr Asn Ile Ile Ile Val Gly
65                  70                  75                  80

His Thr Asp Thr Arg Gly Thr Asp Glu Tyr Asn Leu Glu Leu Gly Lys
                85                  90                  95

Gln Arg Ala Asn Ala Val Lys Asp Phe Ile Leu Glu Arg Asn Lys Ser
            100                 105                 110

Leu Glu Asp Arg Ile Ile Ile Glu Ser Lys Gly Lys Ser Glu Pro Ala
        115                 120                 125

Val Leu Val Tyr Ser Asn Asn Pro Glu Glu Ala Glu Tyr Ala His Thr
    130                 135                 140

Lys Asn Arg Arg Val Val Ile Thr Leu Thr Asp Asn Leu Ile Tyr Lys
145                 150                 155                 160

Ala Lys Ser Ser Asp Lys Asp Pro Ser Ser Asn Lys Thr Glu Gln
                165                 170                 175


<210> SEQ ID NO 40
<211> LENGTH: 50
<212> TYPE: PRT
<213> ORGANISM: Ehrlichia chaffeensis

<400> SEQUENCE: 40

Asn Val Asp His Val Phe Ser Asn Thr Lys Thr Ile Glu Lys Ile Tyr
1               5                   10                  15

Phe Gly Phe Gly Lys Ala Thr Ile Glu Asp Ser Asp Lys Thr Ile Leu
            20                  25                  30

Glu Lys Val Met Gln Lys Ala Glu Glu Tyr Pro Asp Thr Asn Ile Ile
        35                  40                  45

Ile Val
    50


<210> SEQ ID NO 41
<211> LENGTH: 27
<212> TYPE: PRT
<213> ORGANISM: Ehrlichia chaffeensis

<400> SEQUENCE: 41

Ile Glu Asp Ser Asp Lys Thr Ile Leu Glu Lys Val Met Gln Lys Ala
1               5                   10                  15

Glu Glu Tyr Pro Asp Thr Asn Ile Ile Ile Val
            20                  25


<210> SEQ ID NO 42
<211> LENGTH: 17
<212> TYPE: PRT
<213> ORGANISM: Ehrlichia chaffeensis

<400> SEQUENCE: 42

Gly His Thr Asp Thr Arg Gly Thr Asp Glu Tyr Asn Leu Glu Leu Gly
1               5                   10                  15

Glu


<210> SEQ ID NO 43
<211> LENGTH: 33
<212> TYPE: PRT
<213> ORGANISM: Ehrlichia chaffeensis

<400> SEQUENCE: 43
```

```
Gln Arg Ala Asn Ala Val Lys Asp Phe Ile Leu Glu Arg Asn Lys Ser
1               5                   10                  15

Leu Glu Asp Arg Ile Ile Ile Glu Ser Lys Gly Lys Ser Glu Pro Ala
            20                  25                  30

Val


<210> SEQ ID NO 44
<211> LENGTH: 22
<212> TYPE: PRT
<213> ORGANISM: Ehrlichia chaffeensis

<400> SEQUENCE: 44

Leu Val Tyr Ser Asn Asn Pro Glu Glu Ala Glu Tyr Ala His Thr Lys
1               5                   10                  15

Asn Arg Arg Val Val Ile
            20


<210> SEQ ID NO 45
<211> LENGTH: 162
<212> TYPE: PRT
<213> ORGANISM: Ehrlichia canis

<400> SEQUENCE: 45

Met Lys His Lys Leu Val Phe Ile Lys Phe Ile Leu Leu Cys Leu Ile
1               5                   10                  15

Leu Ser Ser Cys Lys Thr Thr Asp His Val Pro Leu Val Asn Thr Asp
            20                  25                  30

His Val Phe Ser Asn Met Lys Thr Ile Glu Lys Ile Tyr Phe Asp Phe
        35                  40                  45

Gly Lys Ala Thr Ile Gly Asp Ser Asp Lys Ala Ile Leu Glu Lys Val
    50                  55                  60

Ile Gln Lys Ala Gln Lys Asp Thr Asn Thr Asn Ile Val Ile Val Gly
65                  70                  75                  80

His Thr Asp Thr Arg Gly Thr Asp Glu Tyr Asn Leu Glu Leu Gly Glu
                85                  90                  95

Gln Arg Ala Asn Ala Val Lys Asp Phe Ile Ile Glu His Asp Lys Ser
            100                 105                 110

Leu Glu Asn Arg Ile Thr Val Gln Ser Lys Gly Lys Ser Glu Pro Ala
        115                 120                 125

Val Leu Val Tyr Ser Ser Asn Pro Glu Glu Ala Glu His Ala His Ala
    130                 135                 140

Lys Asn Arg Arg Val Val Ile Thr Leu Thr Asp Asn Gly Asn Lys Thr
145                 150                 155                 160

Ser Gln


<210> SEQ ID NO 46
<211> LENGTH: 58
<212> TYPE: PRT
<213> ORGANISM: Ehrlichia canis

<400> SEQUENCE: 46

Thr Thr Asp His Val Pro Leu Val Asn Thr Asp His Val Phe Ser Asn
1               5                   10                  15

Met Lys Thr Ile Glu Lys Ile Tyr Phe Asp Phe Gly Lys Ala Thr Ile
            20                  25                  30

Gly Asp Ser Asp Lys Ala Ile Leu Glu Lys Val Ile Gln Lys Ala Gln
        35                  40                  45
```

```
Lys Asp Thr Asn Thr Asn Ile Val Ile Val
    50                  55


<210> SEQ ID NO 47
<211> LENGTH: 26
<212> TYPE: PRT
<213> ORGANISM: Ehrlichia canis

<400> SEQUENCE: 47

Gly Asp Ser Asp Lys Ala Ile Leu Glu Lys Val Ile Gln Lys Ala Gln
1               5                   10                  15

Lys Asp Thr Asn Thr Asn Ile Val Ile Val
            20                  25


<210> SEQ ID NO 48
<211> LENGTH: 17
<212> TYPE: PRT
<213> ORGANISM: Ehrlichia canis

<400> SEQUENCE: 48

Gly His Thr Asp Thr Arg Gly Thr Asp Glu Tyr Asn Leu Glu Leu Gly
1               5                   10                  15

Glu


<210> SEQ ID NO 49
<211> LENGTH: 33
<212> TYPE: PRT
<213> ORGANISM: Ehrlichia canis

<400> SEQUENCE: 49

Gln Arg Ala Asn Ala Val Lys Asp Phe Ile Ile Glu His Asp Lys Ser
1               5                   10                  15

Leu Glu Asn Arg Ile Thr Val Gln Ser Lys Gly Lys Ser Glu Pro Ala
            20                  25                  30

Val


<210> SEQ ID NO 50
<211> LENGTH: 22
<212> TYPE: PRT
<213> ORGANISM: Ehrlichia canis

<400> SEQUENCE: 50

Leu Val Tyr Ser Ser Asn Pro Glu Glu Ala Glu His Ala His Ala Lys
1               5                   10                  15

Asn Arg Arg Val Val Ile
            20


<210> SEQ ID NO 51
<211> LENGTH: 217
<212> TYPE: PRT
<213> ORGANISM: Ehrlichia runantium

<400> SEQUENCE: 51

Met Arg Tyr Gln Leu Ile Val Ala Asn Leu Ile Leu Leu Cys Leu Thr
1               5                   10                  15

Leu Asn Gly Cys His Phe Asn Ser Lys His Val Pro Leu Val Asn Val
            20                  25                  30

His Asn Leu Phe Ser Asn Ile Lys Ala Ile Asp Lys Val Tyr Phe Asp
        35                  40                  45

Leu Asp Lys Thr Val Ile Lys Asp Ser Asp Lys Val Leu Leu Glu Lys
```

```
    50                  55                  60

Leu Val Gln Lys Ala Gln Glu Asp Pro Thr Thr Asp Ile Ile Ile Val
65                  70                  75                  80

Gly His Thr Asp Thr Arg Gly Thr Asp Glu Tyr Asn Leu Ala Leu Gly
                85                  90                  95

Glu Gln Arg Ala Asn Ala Val Arg Asp Phe Ile Ile Ser Cys Asp Lys
            100                 105                 110

Ser Leu Glu Lys Arg Ile Thr Val Arg Ser Lys Gly Lys Ser Glu Pro
        115                 120                 125

Ala Ile Leu Val Tyr Ser Asn Asn Pro Lys Glu Ala Glu Asp Ala His
    130                 135                 140

Ala Lys Asn Arg Arg Val Val Ile Thr Leu Val Asn Asn Ser Thr Ser
145                 150                 155                 160

Thr Asp Asn Lys Val Pro Thr Thr Thr Thr Pro Phe Asn Glu Glu Ala
                165                 170                 175

His Asn Thr Ile Ser Lys Asp Gln Glu Asn Asn Thr Gln Gln Gln Ala
            180                 185                 190

Lys Ser Asp Asn Ile Asn Asn Ile Asn Thr Gln Gln Lys Leu Glu Gln
        195                 200                 205

Asp Asn Asn Asn Thr Pro Glu Val Asn
    210                 215


<210> SEQ ID NO 52
<211> LENGTH: 58
<212> TYPE: PRT
<213> ORGANISM: Ehrlichia ruminantium

<400> SEQUENCE: 52

Asn Ser Lys His Val Pro Leu Val Asn Val His Asn Leu Phe Ser Asn
1               5                   10                  15

Ile Lys Ala Ile Asp Lys Val Tyr Phe Asp Leu Asp Lys Thr Val Ile
            20                  25                  30

Lys Asp Ser Asp Lys Val Leu Leu Glu Lys Leu Val Gln Lys Ala Gln
        35                  40                  45

Glu Asp Pro Thr Thr Asp Ile Ile Ile Val
    50                  55


<210> SEQ ID NO 53
<211> LENGTH: 25
<212> TYPE: PRT
<213> ORGANISM: Ehrlichia ruminantium

<400> SEQUENCE: 53

Asp Ser Asp Lys Val Leu Leu Glu Lys Leu Val Gln Lys Ala Gln Glu
1               5                   10                  15

Asp Pro Thr Thr Asp Ile Ile Ile Val
            20                  25


<210> SEQ ID NO 54
<211> LENGTH: 17
<212> TYPE: PRT
<213> ORGANISM: Erhlichia ruminantium

<400> SEQUENCE: 54

Gly His Thr Asp Thr Arg Gly Thr Asp Glu Tyr Asn Leu Ala Leu Gly
1               5                   10                  15

Glu
```

<210> SEQ ID NO 55
<211> LENGTH: 33
<212> TYPE: PRT
<213> ORGANISM: Ehrlichia ruminantium

<400> SEQUENCE: 55

```
Gln Arg Ala Asn Ala Val Arg Asp Phe Ile Ile Ser Cys Asp Lys Ser
1               5                   10                  15

Leu Glu Lys Arg Ile Thr Val Arg Ser Lys Gly Lys Ser Glu Pro Ala
            20                  25                  30

Ile
```

<210> SEQ ID NO 56
<211> LENGTH: 22
<212> TYPE: PRT
<213> ORGANISM: Ehrlichia ruminantium

<400> SEQUENCE: 56

```
Leu Val Tyr Ser Asn Asn Pro Lys Glu Ala Glu Asp Ala His Ala Lys
1               5                   10                  15

Asn Arg Arg Val Val Ile
            20
```

<210> SEQ ID NO 57
<211> LENGTH: 355
<212> TYPE: PRT
<213> ORGANISM: Anaplasma phagocytophilum

<400> SEQUENCE: 57

```
Met Ser Phe Thr Met Ser Lys Leu Ser Leu Asp Pro Thr Gln Gly Ser
1               5                   10                  15

His Thr Ala Glu Asn Ile Ala Cys Ser Ile Phe Asp Met Val Leu Gly
            20                  25                  30

Val Lys Ser Thr Ala Lys Leu Leu Ala Gly Thr Trp Ala Gly Thr Ser
        35                  40                  45

Ser Thr Ile Trp Lys Thr Val Thr Gly Ala Ala Ser Ser Thr Lys Glu
    50                  55                  60

Ala Ser Ser Lys Ser Tyr Gly Thr Leu Arg Ser Ser Leu Gly Ser Ser
65                  70                  75                  80

Ala Ser Arg Arg Met Leu Gly Thr Cys Ala Thr Ala Ala Leu Cys Leu
                85                  90                  95

Thr Ala Pro Leu Leu Gly Ala Ala Ala Ala Gly Ala Ala Ile Thr Cys
            100                 105                 110

Ala Leu Ile Thr Ile Cys Met Ala Leu Leu Phe Leu Val Leu Tyr Thr
        115                 120                 125

Val Leu His Ile Ala Ser Gln Met Leu Arg Cys Ala Ser Leu Leu Leu
    130                 135                 140

Ser Met Val Cys Asn Ile Leu His Ser Thr Phe Thr Ala Thr Lys Ser
145                 150                 155                 160

Cys Leu Gly Gly Lys Ser Pro Ala Arg Thr Thr Glu Glu Arg Val Ala
                165                 170                 175

Gly Asp Leu Asp His Lys Gly Val Asp Ser Asp Arg Lys His Asp Ala
            180                 185                 190

Glu Lys Thr Glu Glu Lys Lys His Gly Leu Gly Ser Leu Cys Lys Ser
        195                 200                 205

Leu Ala Ile Asn Leu Val Ser Leu Met Gly Thr Ala Leu Val Thr Thr
    210                 215                 220
```

```
Pro Ile Ile Leu Leu Ala Val Val Leu Leu Val Leu Val Pro Val Tyr
225                 230                 235                 240

Leu Leu Cys Ala Thr Val His His Ile Tyr Gln Gly Asn Tyr Glu Asp
                245                 250                 255

Arg Asn Asn Asp Lys Gly Ser Ser Arg Gly Gly Gly Thr Thr Tyr Tyr
            260                 265                 270

Pro Met Thr Met Ser Ala Ser Ala Ser Glu Glu Ser Leu Ser Ser Ile
        275                 280                 285

Ile Ser Glu Gly Gly Leu Ser Lys Thr Ser Leu Pro Ser Tyr Ser Ala
    290                 295                 300

Ala Thr Ala Thr Gly Thr Gly Asn Ala Thr Gly Glu Val Phe Ser His
305                 310                 315                 320

Ser His Ser Ser Gly Lys Ser Ser Ser Lys Pro Glu Ser Arg Pro Glu
                325                 330                 335

Ser Asn Leu Gln Asn Val Val Ala Glu Thr Met Ser Gln Gln Gln Arg
            340                 345                 350

Ser Val Ser
        355


<210> SEQ ID NO 58
<211> LENGTH: 338
<212> TYPE: PRT
<213> ORGANISM: Anaplasma phagocytophilum

<400> SEQUENCE: 58

Met Arg Thr Phe Cys Trp Phe Val His Arg Phe Tyr Leu Arg Asn Tyr
1               5                   10                  15

Cys Phe Leu Asn Lys Asn Cys Ser Gln Cys Ser Asn Thr Thr Tyr Thr
            20                  25                  30

Ser Thr Thr Val Ile Ile Tyr Ala Thr Ile Ser Ser Lys Ser Ile Val
        35                  40                  45

Ile Ser Phe Ser Asp Ala Arg Cys Val Glu Asp Phe Lys Gly Lys Phe
    50                  55                  60

Thr Thr Leu Asp Ala Gly Ile Ala Ser Arg Ala Ile Phe Ser Met Ser
65                  70                  75                  80

Val Ala Ile Lys Tyr Ser Asp Lys Asn Leu Val Glu Leu Ile Pro Glu
                85                  90                  95

Gly Glu Phe Thr Tyr Cys Asp Val Asn Thr Met Val Gly His Met Leu
            100                 105                 110

Arg His Gly Phe Thr Phe Lys Gln Glu Val Leu Ser Ser Ile Leu Glu
        115                 120                 125

Gln Ala Ser Ala Leu Ala Thr Glu Asn Phe Val Val Leu Lys Ala Gly
    130                 135                 140

Glu Arg Ser Ser Tyr Ile Val Gly Val Tyr Gln Asp Thr Val Thr Val
145                 150                 155                 160

Ser Pro Leu Thr Ser Glu Tyr Leu Asp Leu Glu Ser Gly Pro Ser Gln
                165                 170                 175

Arg Leu Val Lys Leu Leu Arg Thr Glu Ser Ala Ile Ser Ser Val Asn
            180                 185                 190

Val Asp Ala Gln Asn Arg Ser Ile Thr Ile Leu Val Arg Gly Asn Val
        195                 200                 205

Cys Asp Ala Leu Gly Thr Leu Cys Asn Val Met Ile Thr Ile Gly Ala
    210                 215                 220

Ile Glu Ala Lys Glu Lys Gly Ala Val Leu Val Lys Leu Val Arg Leu
```

```
225                 230                 235                 240

Ala Phe Leu Asp Leu Met Gly Asn Glu Ile Arg Ser Val Arg Asn Ile
                245                 250                 255

Ala Ser Cys Ser Val Ala His Pro Leu Ser Lys Tyr Lys Gly Val Ala
            260                 265                 270

Arg Thr Ile Glu Asn Ile Leu Thr Cys Leu Ser Asn Lys Thr Leu Asp
        275                 280                 285

Ala Val Val Leu Gly Gln Leu Glu Asp Ala Leu Glu Gly Lys Gly Glu
    290                 295                 300

Phe Ser Ala Leu Pro Ser Val Leu Thr Lys Gly Phe Val Lys Leu Asn
305                 310                 315                 320

Arg Asp Phe Asn Gly Gln Leu Glu Asn Ile Ile Gly Ser Glu Lys Arg
                325                 330                 335

Val Gln


<210> SEQ ID NO 59
<211> LENGTH: 147
<212> TYPE: PRT
<213> ORGANISM: Anaplasma phagocytophilum

<400> SEQUENCE: 59

Met Gln Gln Ser Ile Ser Thr Asp Thr Leu Gly Ser Ser Glu Val Arg
1               5                   10                  15

Gln Pro Lys Pro Arg Lys Ile Ala Thr Gly Ala Arg Ala Ser Arg Ala
            20                  25                  30

Thr Thr Ala Ala Arg Lys Ser Val Ser Ser Thr Thr Asn Lys Asn Val
        35                  40                  45

Ala Val Asp Val Arg Ser Arg Ser Ser Lys Ser His Asn Asp Asp Lys
    50                  55                  60

Val Ala Ile Asp Ser His Ala Glu Ala Arg Gln Leu Pro Glu Glu Asp
65                  70                  75                  80

Arg Lys Glu Ser Leu Ser Pro Asp Val Ser Thr Val Lys Ser Glu His
                85                  90                  95

Ala Ser Arg Ser Ser Glu Asp Ile Gln Ser Pro Val Asp Asn Ser Gly
            100                 105                 110

Pro Glu Val Ser Gly Gly Leu Lys Thr Arg Tyr Ser Ala Trp Ile Ala
        115                 120                 125

Leu Leu Cys Lys Gln Tyr Gly Arg Phe Thr Ala Phe Phe Ser Lys Lys
    130                 135                 140

Arg Glu Ser
145


<210> SEQ ID NO 60
<211> LENGTH: 645
<212> TYPE: PRT
<213> ORGANISM: Anaplasma phagocytophilum

<400> SEQUENCE: 60

Met Ala Ala Glu Arg Ile Ile Gly Ile Asp Leu Gly Thr Thr Asn Ser
1               5                   10                  15

Cys Val Ala Val Met Glu Ala Gly Thr Ala Lys Val Ile Glu Asn Ser
            20                  25                  30

Glu Gly Ser Arg Thr Thr Pro Ser Val Val Ala Phe Thr Asp Asn Glu
        35                  40                  45

Arg Leu Val Gly Glu Leu Ala Lys Arg Gln Ala Asn Ile Asn Ala Gln
    50                  55                  60
```

```
Asn Thr Ile Tyr Ala Ser Lys Arg Ile Ile Gly Arg Arg Tyr Asp Asp
65                  70                  75                  80

Met Arg Asp Leu Lys Cys Pro Tyr Glu Val Phe Pro Ala Lys Asn Gly
                85                  90                  95

Asp Ala Trp Ile Arg Ala Lys Gly Glu Gly Tyr Ser Pro Val Gln Ile
            100                 105                 110

Gly Ala Phe Val Leu Glu Lys Ile Lys Glu Thr Ala Glu Arg Tyr Phe
        115                 120                 125

Gly Ala Pro Val Lys Lys Ala Val Ile Thr Val Pro Ala Tyr Phe Asn
    130                 135                 140

Asp Ala Gln Arg Gln Ala Thr Lys Asp Ala Gly Thr Ile Ala Gly Leu
145                 150                 155                 160

Asp Val Val Arg Ile Ile Asn Glu Pro Thr Ala Ala Ala Leu Ala Tyr
                165                 170                 175

Gly Leu Asp Lys Gly Asp Lys Gln Arg Thr Ile Val Val Tyr Asp Leu
            180                 185                 190

Gly Gly Gly Thr Phe Asp Val Ser Val Leu Glu Ile Ala Asp Gly Val
        195                 200                 205

Phe Glu Val Lys Ala Thr Asn Gly Asp Thr Lys Leu Gly Gly Glu Asp
    210                 215                 220

Phe Asp Asn Ala Ile Met Glu His Met Met Glu Ser Phe Gln Lys Glu
225                 230                 235                 240

Thr Gly Ile Asn Leu Arg Asn Asp Pro Met Ala Val Gln Arg Val Lys
                245                 250                 255

Glu Ala Ala Glu Lys Ala Lys Ile Glu Leu Ser Thr Arg Leu Glu Thr
            260                 265                 270

Asp Ile Thr Leu Pro Phe Ile Ser Ser Asp Ser Thr Gly Ala Lys His
        275                 280                 285

Leu Ser Leu Lys Leu Ser Arg Ala Lys Phe Glu Gly Leu Val Asp Glu
    290                 295                 300

Leu Ile Glu Arg Thr Ile Glu Pro Cys Lys Lys Ala Leu Ser Asp Ala
305                 310                 315                 320

Gly Ile Lys Asp Asn Ser Lys Val Asp Glu Val Val Leu Val Gly Gly
                325                 330                 335

Met Thr Arg Val Pro Lys Val Ile Gln Arg Val Lys Asp Phe Phe Gly
            340                 345                 350

Lys Glu Pro Cys Gln Gly Val Asn Pro Asp Glu Val Val Ala Val Gly
        355                 360                 365

Ala Ala Ile Gln Gly Gly Ile Leu Thr Gly Asp Val Arg Asp Val Leu
    370                 375                 380

Leu Leu Asp Val Ala Pro Leu Ser Leu Gly Ile Glu Thr Leu Gly Gly
385                 390                 395                 400

Val Phe Thr Pro Leu Ile Glu Arg Asn Thr Thr Ile Pro Thr Lys Lys
                405                 410                 415

Ser Gln Val Phe Ser Thr Ala Glu Asp Gly Gln Thr Ala Val Thr Ile
            420                 425                 430

Lys Val Tyr Gln Gly Glu Arg Lys Met Ala Ile Asp Asn Lys Leu Leu
        435                 440                 445

Gly Gln Phe Ser Leu Glu Gly Ile Pro His Ala Pro Arg Gly Val Pro
    450                 455                 460

Gln Ile Glu Val Thr Phe Asp Ile Asp Ala Asn Gly Ile Val His Val
465                 470                 475                 480
```

-continued

Ser Ala Lys Asp Lys Ala Ser Gly Lys Glu Gln Thr Ile Lys Ile Gln
485 490 495

Ser Ser Gly Gly Leu Ser Asp Glu Glu Ile Lys Lys Met Val Lys Asp
500 505 510

Ala Gln Asp Arg Ala Glu Asp Asp Glu Lys Arg Lys Lys His Val Glu
515 520 525

Leu Lys Asn Ser Ser Glu Gly Leu Ile His Ser Val Glu Lys Ser Leu
530 535 540

Lys Asp Tyr Gly Asp Lys Val Ala Gly Ala Asp Lys Ser Asn Ile Glu
545 550 555 560

Ser Ala Ile Lys Asp Leu Arg Glu Cys Leu Asn Asp Ser Asn Cys Ser
565 570 575

Thr Asp Thr Leu Gln Gln Lys Tyr Asp Ala Leu Met Asn Leu Ser Met
580 585 590

Lys Leu Gly Glu Ala Ala Tyr Ala Ala Asn Lys Asn Asp Gly Ala Gly
595 600 605

Ser Ala Asp Gln Ser Gly Ser Ser Ser Gly Gly Ser Asp Gly Asn Pro
610 615 620

Glu Glu Arg Val Val Asp Ser Glu Tyr Gln Glu Ile Asn Lys Asp Glu
625 630 635 640

Asp Lys Lys Asn Thr
645

<210> SEQ ID NO 61
<211> LENGTH: 453
<212> TYPE: PRT
<213> ORGANISM: Anaplasma phagocytophilum

<400> SEQUENCE: 61

Met Lys Ala Thr Leu Ile Thr Cys Tyr Thr Gln Val Cys Val Cys Tyr
1 5 10 15

Gly Tyr Val Met His Ser Ser Met Ile Tyr Asn Ser Lys Thr Tyr Arg
20 25 30

Val Tyr Ser Arg Val Ala Gly Glu Ile Lys Asp Asp Arg Leu Thr His
35 40 45

Arg Ala Val Ala Val Tyr Cys Ser Trp Leu Leu Glu Arg Ser Ile Asn
50 55 60

Glu Leu Arg Ala Val Leu Glu Thr Ser Gly Pro Asp Gly Tyr Val Phe
65 70 75 80

Val Gln Leu Ala Leu Asp Arg Met Glu Glu Val Tyr Asn Asp Ile Tyr
85 90 95

Gln Ala Arg Ala Gly Thr His Asp Asp Ile Val Lys Ala Leu Ser Ala
100 105 110

Asn Cys Asp Gln Tyr Leu Phe Gln Cys Arg Ser Ala Leu Phe His Leu
115 120 125

Ser Arg Phe Arg Asp Gly Ser Leu Pro Leu Glu Gly Pro Val Gly Asp
130 135 140

Asp Val Ser Ser Phe Cys Thr Ala Ser Ser Asn Ile Ala Ser Val Ile
145 150 155 160

Thr Leu Leu Gln Thr Asn Arg Ser Leu Pro Asp Arg Val Ser Ser Asp
165 170 175

Thr Arg Asn Arg Leu Cys Met Leu Ile Asp Ser Leu Ser Asp Ser Val
180 185 190

Thr Ala Met Pro Asp Ser Ala Phe Met His Leu Ala Gln Gly Ser Ala
195 200 205

```
Gly Phe Ala Ser Val Tyr Asp Ala Arg Cys Ala Phe Leu Phe Ala Val
    210                 215                 220

Glu Glu Leu Arg Ala Leu Ala Tyr Thr Val His Thr Asp Thr Asp Thr
225                 230                 235                 240

Ala Ala Arg Val Cys Leu Gly Asp Ser Phe Glu Ala Leu Leu Glu Asn
                245                 250                 255

Ile Arg Glu Ala Ile Arg Arg Val Ser Asp Ala Pro Gly Val Thr Ala
            260                 265                 270

Arg Ala Ser Cys Ser Cys Thr Leu Ala Asn Lys Ala Leu Ala Arg Ile
        275                 280                 285

Gln Ala Met Phe Glu Asn Tyr Val Asn Gly Thr His Ala Arg Asp Ser
    290                 295                 300

Asp Leu Ser Asp Glu Met Tyr Met Ser Thr Thr Ile Val Ser Ala Tyr
305                 310                 315                 320

Ala Ala Ala Arg Ser Leu Cys Tyr Ser Cys Ile Ser Ala Ala Ser Glu
                325                 330                 335

Leu Pro Cys Val Pro Ser Ile Ile Glu Cys Ser Ser Ala Leu Tyr Asp
            340                 345                 350

Leu Tyr Ser His Leu Ser Ala Arg Ala Phe Ile Asp Leu Ala Asp Pro
        355                 360                 365

His Asp Val Asn Asn Ile Leu Pro Ala Leu Asn Lys Ala Arg Glu Ala
    370                 375                 380

Leu Gly Lys Val Asp Arg Ser Thr Leu Pro Ser Asn Arg Asp Thr Glu
385                 390                 395                 400

Ile Tyr Asp Arg Leu Arg Lys Ala Ile Glu Gln Ala Ser Gly Arg Cys
                405                 410                 415

Ile Met Arg Gln Leu Glu Pro Asp Tyr Leu Asp Leu Ala Pro Ser Thr
            420                 425                 430

Gly Gln Asn Asp Leu Ser Ile Glu Gly Leu Gly Ala Ala Gly Ala Ser
        435                 440                 445

His Asp Leu His His
    450


<210> SEQ ID NO 62
<211> LENGTH: 442
<212> TYPE: PRT
<213> ORGANISM: Anaplasma phagocytophilum

<400> SEQUENCE: 62

Met Cys Val Cys Tyr Gly Ala Val Met His Ser Phe Ile Asp Pro Ile
1               5                   10                  15

Ser Lys Thr Tyr Arg Val Tyr Ser Asn Val Glu Glu Ser Leu Arg Ser
            20                  25                  30

Gly Glu Phe Thr Glu Arg Ala Val Ala Val Arg Thr Ser Trp Leu Leu
        35                  40                  45

Glu Gln Ala Leu Glu Arg Leu His Arg Val Val Glu Ala Ser Glu Glu
    50                  55                  60

Gly Ile Pro Ser Ser Leu Val Lys Met Ala Leu Gln Asn Val Arg Asp
65                  70                  75                  80

Ile Tyr Ser Asn Ile Tyr Arg Ala Arg Glu Gly Thr Ala Asn Asn Ile
                85                  90                  95

Lys Lys Ala Leu Val Asp Asn Gly Arg Glu His Ile Ser Lys Leu Arg
            100                 105                 110

Thr Val Leu Leu Tyr Leu Ala Leu Ala Arg Ser Lys Ser Leu Pro Asn
```

-continued

```
        115                 120                 125

Glu Gly Pro Ala Gly Ala Ser Val Thr Glu Ile Ser Ala Ala Ser Tyr
    130                 135                 140

Asn Ala Ala Ser Ala Leu Ser Ile Leu Gln Ser Asn Leu Gly Leu Pro
145                 150                 155                 160

Asp Glu Ala Ser Val Asn Thr Arg Asp Arg Leu Cys Val Leu Leu Asp
                165                 170                 175

Ser Leu Ser Gly Thr Ile Glu Leu Ile Pro Gly Arg Ala Leu Leu Arg
            180                 185                 190

Ser Val Arg Gly Ser Thr Gly Phe Ile Ser Pro Ser Glu Val Arg Asn
        195                 200                 205

Ala Leu Leu Leu Ala Val Glu Glu Ala His Ala Leu Val Tyr Thr Thr
    210                 215                 220

His Asp Ser Ala Asp Lys Asp Ala Arg Gly Cys Val Gln Gly Ala Leu
225                 230                 235                 240

Glu Leu Val Leu Tyr Ser Ile Lys Arg Val Ile Cys Gly Ile Arg Gly
                245                 250                 255

Lys Asn Ile Ser Ser Arg Ala Ser Trp Ser Cys Ala Leu Ala Ser Gln
            260                 265                 270

Met Met Tyr Thr Ile Gln Glu Val Phe Asp Gly Tyr Val Ser Asn Thr
        275                 280                 285

His Thr Arg Asp Ser Asp Val Ser Asp Lys Glu Phe Leu Ser Asn Asn
    290                 295                 300

Val Ile Arg Ala Phe Thr Ser Ala Arg His Leu Leu Ala Ser Cys Val
305                 310                 315                 320

Ser Val Pro Pro Glu Glu Arg Pro Ser Ser Ser Glu Tyr Val Ile Arg
                325                 330                 335

Cys Ser Gly Met Leu Arg Glu Val Tyr Ser His Leu Gly Thr Cys Glu
            340                 345                 350

Ser Ile Asp Leu Ala Asn Pro His Gly Ala Asn Asn Ile Leu Pro Ala
        355                 360                 365

Leu Asn Lys Ala Arg Glu Ala Leu Asp Glu Val Asp Pro Ser Asp Leu
    370                 375                 380

Pro Ser His Arg Asp Ala Glu Thr Tyr Ser Arg Ile Arg Glu Ala Ile
385                 390                 395                 400

Met Gln Ala Ser Arg Arg Cys Ile Met Gln Gln Cys Ser Glu Pro Asp
                405                 410                 415

Leu Leu Asp Ser Ala Leu Gly Ala Gly Trp Asp Ala Leu Ser Ile Glu
            420                 425                 430

Gly Leu Gly Ala Gly Cys Trp Arg Phe Ser
        435                 440


<210> SEQ ID NO 63
<211> LENGTH: 1047
<212> TYPE: PRT
<213> ORGANISM: Anaplasma phagocytophilum

<400> SEQUENCE: 63

Met Ala Lys Arg Phe Leu Asn Asp Thr Glu Lys Lys Leu Leu Ser Leu
1               5                   10                  15

Leu Lys Ser Val Met Gln His Tyr Lys Pro Arg Thr Gly Phe Val Arg
            20                  25                  30

Ala Leu Leu Ser Ala Leu Arg Ser Ile Ser Val Gly Asn Pro Arg Gln
        35                  40                  45
```

-continued

```
Thr Ala His Asp Leu Ser Val Leu Val Thr Gln Asp Phe Leu Val Glu
    50                  55                  60

Val Ile Gly Ser Phe Ser Thr Gln Ala Ile Ala Pro Ser Phe Leu Asn
65                  70                  75                  80

Ile Met Ala Leu Val Asp Glu Glu Ala Leu Asn His Tyr Asp Arg Pro
                85                  90                  95

Gly Arg Ala Pro Met Phe Ala Asp Met Leu Arg Tyr Ala Gln Glu Gln
            100                 105                 110

Ile Arg Arg Gly Asn Leu Leu Gln His Arg Trp Asn Glu Glu Thr Phe
        115                 120                 125

Ala Ser Phe Ala Asp Ser Tyr Leu Arg Arg Arg His Glu Arg Val Ser
    130                 135                 140

Ala Glu His Leu Arg Gln Ala Met Gln Ile Leu His Ala Pro Ala Ser
145                 150                 155                 160

Tyr Arg Val Leu Ser Thr Asn Trp Phe Leu Leu Arg Leu Ile Ala Ala
                165                 170                 175

Gly Tyr Val Arg Asn Ala Val Asp Val Val Asp Ala Glu Ser Ala Gly
            180                 185                 190

Leu Thr Ser Pro Arg Ser Ser Ser Glu Arg Thr Ala Ile Glu Ser Leu
        195                 200                 205

Leu Lys Asp Tyr Asp Glu Glu Gly Leu Ser Glu Met Leu Glu Thr Glu
    210                 215                 220

Lys Gly Val Met Thr Ser Leu Phe Gly Thr Val Leu Leu Ser Thr Tyr
225                 230                 235                 240

Val Asn Glu Leu Arg Ala Glu Val Ala Gln Glu Phe Ala Glu His His
                245                 250                 255

Arg Phe Leu Ser Arg Val Leu Ser Thr Cys Ser Ala Leu Leu Ser Pro
            260                 265                 270

Leu Gly Thr Val Ala Val Val Ala Tyr Cys Ala Ser Met Phe Ser Ser
        275                 280                 285

Ile Ile Gln Gln Ala Thr Asn Pro Ser Ser Asp Lys Glu Lys Tyr Cys
    290                 295                 300

Ala Leu Ile Asp Tyr Ile Asn Glu Thr Ile Ala Ser Phe Gly Ser Gly
305                 310                 315                 320

Asn Gly Asn Ala Thr Ile Thr Glu Ala Leu Ile Arg Gly Ser Asn Leu
                325                 330                 335

Thr Ala Leu Phe Gly Asn His Ser Cys Ser Glu Ser Asn Glu Ala Leu
            340                 345                 350

His Asp Ile Leu Ser Asn Arg Arg Asn Glu Ser Leu Ser Ile Thr Asn
        355                 360                 365

Met Ser Ala Met Pro Ala Ser Ile Ser Val Leu Thr Thr Met Tyr Leu
    370                 375                 380

Ala Leu Pro Ile Ile Ala Phe Gly Gly Tyr Ala Ala Gln Trp Val Ser
385                 390                 395                 400

Arg Arg Met Ser Ser Arg Gly Arg Gly Gly Phe Ser Ser Pro Glu Met
                405                 410                 415

Phe Ser Met Leu Ser Ala Val Val Cys Ala Lys Leu Gly Leu Asn Thr
            420                 425                 430

Phe Leu Thr Leu Thr Ala His Val Ser His Lys Ala Phe Ser Thr Ala
        435                 440                 445

Leu Asn Trp Ser Val Thr Arg Leu Phe Leu Pro Leu Ser Leu Ile Glu
    450                 455                 460

Gln Pro Lys Lys Ile Gly Leu Phe Val Asn Ser Ala Met Ser Ala Ala
```

-continued

```
465                 470                 475                 480

Trp Ser Ser Arg Arg Leu Arg Phe Glu Pro Ser Ser Arg Ala Cys Ala
                485                 490                 495

Ile Ala Ala Ala Leu Ser Ile Pro Phe Glu Tyr Ala Gly His Val Val
            500                 505                 510

Ala Lys Leu His Val Ile Asn Thr Gly Trp Thr Gln Val Pro Pro Ser
        515                 520                 525

Cys Arg Gln Ile Leu Asn Phe Thr Val Lys His Ala Arg Val Ala Ala
    530                 535                 540

Phe Phe Gly Thr Ile Ile Ala Ala Arg Arg His Ile Arg Asn Met Pro
545                 550                 555                 560

Tyr Ser Arg Arg Leu Glu Arg Ile Ile Trp Ala Asp Gly Val Lys Ala
                565                 570                 575

Thr Thr Ala Pro Ala Ala Leu Leu Leu Leu Asp Val Ala Ala Gly Asn
            580                 585                 590

Val Phe Leu Ser Thr Val Val Leu Thr Val Asp Ser Leu Val Ser Leu
        595                 600                 605

Ile Pro Asp Met Ile Cys Ser Ala Asn Val Asp Met Leu Asn Asn Ala
    610                 615                 620

Gly Asn Gln Leu Ala Ala Leu Glu Gln Trp Leu Val Glu Asn Leu Asp
625                 630                 635                 640

Glu Glu Ala Leu Leu Lys Ile Ala Met Leu Thr Ser Leu Gln Arg Leu
                645                 650                 655

Pro Gly Ser Thr His Gly Glu Leu Glu Lys Ile Leu Glu Glu Phe Tyr
            660                 665                 670

Asn Lys Asp Gln Ile Thr Asp His Gly Val Asp Leu Thr Val Asp Asp
        675                 680                 685

Asp Phe Thr Glu Gly Ile Thr Glu Arg Gln Leu Leu Glu Trp Gln Ser
    690                 695                 700

Asp Asp Ala Ser Arg Arg Arg Thr Arg Gly Gly Asp Cys Ala Asp Ala
705                 710                 715                 720

Ser Ser Glu Gly Glu Leu Ile Gly Ala Thr Ser Arg Asp Tyr Tyr Asp
                725                 730                 735

Pro Pro Glu Arg Arg Arg Gly Pro Thr Leu Tyr Glu Glu Leu Val Arg
            740                 745                 750

Gly Ile Leu Glu Arg His Gly Thr Arg Phe Ser Asp Ala Leu Ala Gly
        755                 760                 765

Glu Glu Glu Asp Ala Asp Glu Ala Leu Leu Phe Ser Asp Leu Arg Leu
    770                 775                 780

Gln Leu Asp Asp Ala Ala Val Pro His Glu Glu Gln Ser Glu Arg Gly
785                 790                 795                 800

Arg Ser Ser Arg Arg Gly Arg Phe Cys Gly Asp Glu Asp Phe Asp Val
                805                 810                 815

Lys Cys Gln Gly Gln Gly Asp Gly Arg Arg Ser Arg Arg Ser Asp Arg
            820                 825                 830

Arg Gly Tyr Ser Glu Glu Pro Ala Leu Gly Asp Met Arg His Ser Ser
        835                 840                 845

Arg Gly Ala Ala Ser Glu Ser Asp Ala Arg Arg Ser Arg Arg Ser Asp
    850                 855                 860

Arg Glu Glu Pro Ala Thr Ser Pro Arg Arg His Pro Ala Gly Glu Val
865                 870                 875                 880

Pro Gln Arg Gln Asp Glu Ala Ser Pro Ser Gly Leu Arg Asn His Pro
                885                 890                 895
```

```
Ser Gly Ala Ile Pro Lys Val Arg Ser Ala Ser Ala Ala Met His Thr
            900                 905                 910

Lys Lys Asp Lys Ser Lys Lys Ser Ala Arg Ser Ser Glu Ser Thr Arg
        915                 920                 925

Arg Gly Val Asp Leu Gly Phe Leu Gly Ser Pro Lys Asp Leu Glu Arg
    930                 935                 940

Cys Val Leu Glu Gly Glu Arg Ala Arg Ala Arg Ser Pro Arg Cys Gly
945                 950                 955                 960

Val Gly Thr Pro Pro Cys His Leu Asp Arg Val Val Tyr Glu Thr Glu
                965                 970                 975

Gly Ala Gln Asp Val Asp Asn Asp Val Phe Asp Val Ser Arg Tyr Val
            980                 985                 990

Thr Pro Arg Asn Gln Ala Gly Glu  Arg Val Arg Val Gly  Thr Ser Ser
        995                 1000                1005

Ser Ser  Arg Ala Pro Gln Gly  Ala Thr Gly Leu Ala  Pro Gly Thr
    1010                1015                1020

Ser Leu  Thr Ser Leu Asp Asp  Asp Ala Leu Asp Ile  Leu Asp Ala
    1025                1030                1035

Ile Gln  Gly Gln Arg Gly Arg  Arg Arg
    1040                1045


<210> SEQ ID NO 64
<211> LENGTH: 1528
<212> TYPE: PRT
<213> ORGANISM: Anaplasma phagocytophilum

<400> SEQUENCE: 64

Met Thr Leu Leu Leu Lys Gln Asn Pro Pro Lys Ala Ser Val Ala Leu
1               5                   10                  15

Leu Gly Ser Ala Ile Asp Phe Phe Leu Cys Arg Asp Arg Asn Ser His
            20                  25                  30

Pro Ala Arg Arg Arg Met Val Ile Leu Leu Ala Glu Gly Phe Thr Leu
        35                  40                  45

Arg Glu Gly Ser Ala Val Pro Pro Ala Leu Ile His Glu Asn Leu Thr
    50                  55                  60

Ser Pro Asp Leu Leu Ala Arg Ala Leu His Lys Thr Ala Ser Asn Ser
65                  70                  75                  80

Thr Ala Phe Gln Gln Val Pro Phe Gln Leu Trp His Ala Leu Ala Leu
                85                  90                  95

Ala Tyr Asn Ser Leu Pro Gly Lys Asn Gln Glu Glu Asp Leu Thr Asn
            100                 105                 110

Phe Val Leu Gly Cys Leu Asp Gly Val Ser Glu Asp Met Thr Ile Val
        115                 120                 125

Arg Glu Glu Asp Ser Thr Thr Phe Glu Val Gln Ser Tyr Thr Thr Phe
    130                 135                 140

Ser Arg Val His Ser Leu Leu Ala Ser Ala Pro Ser Ser Tyr Lys Asn
145                 150                 155                 160

Gly Ala Leu Thr Val His Glu Ser Cys Ile Phe Ser Ile Gln Asp Lys
                165                 170                 175

Ser Gly Val Pro Ile Ala Lys Val Lys Met Trp Val Glu Tyr Asp Ile
            180                 185                 190

Ala Pro Ser Thr Lys Ala Glu Gly Val Tyr Arg Thr Ala Val Lys Lys
        195                 200                 205

Val Lys Leu Val Leu Thr Glu Arg Asp Cys Arg Asp Val Arg Gln Gly
```

```
    210                 215                 220

Glu Pro Gly Ser Val Cys Ser Trp His Asn Ile Pro Lys Ala Leu Ala
225                 230                 235                 240

Lys His Tyr Val Arg Val Pro Glu Arg Pro Thr His Val Leu Tyr Ser
                245                 250                 255

Ala Cys Asn Leu Gln Arg His Asn Pro Arg Tyr Met Ala Arg Arg Val
            260                 265                 270

Phe Tyr Asp Val Ser Gly Ile Asp Glu Cys Ile Leu Arg Ala Tyr Ser
        275                 280                 285

Val Ile Ser Gly Met Pro Pro Glu Val Leu Glu Leu Ser Phe Cys Asn
    290                 295                 300

Thr Val Ile Ser Gln Glu Ala Ser Gly Val Phe Arg Val Val Val Arg
305                 310                 315                 320

Gly Val Val Gly Leu Val Gly Tyr Asp Lys Ser Ser Val Val Gln Gln
                325                 330                 335

Gly Ala Val Ser His Gly Arg Asp Ala Val Ser Lys Met Gly Val Cys
            340                 345                 350

Met Ser Phe Val Ala Ser Gln Ala His Asp Ala Cys Ala Thr Ile Leu
        355                 360                 365

Arg His Val Ala Val Thr Val Asn Thr Phe Gly Asn Val Leu Thr Leu
    370                 375                 380

Gly Gly Gly Ile Ser Leu Arg Asp Phe Leu Ala Gly Ser Ala Lys Asp
385                 390                 395                 400

Thr Asp Phe Ala Gly Ser His Ile Cys Asn Phe Gly Glu Glu Ile Val
                405                 410                 415

Ala His Gly Leu Ser Leu Trp Glu Asp Leu Gly Lys Arg His Arg Trp
            420                 425                 430

Ala Ser His Ser Val Pro Val Arg Gly Asp Cys Gly Ile Phe Ile Gln
        435                 440                 445

His Ser Asp Glu Ile Arg Glu Ile Leu Arg Ser Gln Pro Lys His Ala
    450                 455                 460

Ala Asn Ile Val Glu Lys Thr Gly Val Asn Thr Glu Asn Leu Arg Val
465                 470                 475                 480

Leu Leu Ser Ser Ile Leu Ser Asn Ser Ser Gly Ser Ser Leu Pro Val
                485                 490                 495

Glu Leu Ala Ala His Tyr Val Ala His Glu Gly Val Val Ala Asp Asn
            500                 505                 510

Gly Asp Ser Ala Arg Arg Leu Pro Val Asn Gln His Val Leu Glu Glu
        515                 520                 525

His Leu Val Tyr Arg Val Thr Ser Val Ser Gly Ile His Ile His Ala
    530                 535                 540

Cys Val Asp Tyr Val Val Glu Asp Ile Asp Thr Pro Gly Ser Val Lys
545                 550                 555                 560

Asp Leu Gly Leu Cys Ile Arg Asp Val Arg Ile Gly Thr Arg Val Ala
                565                 570                 575

Ser Ser Ala Glu Glu Val Cys Ser Ala Ile Gln Glu Lys Glu Gly Arg
            580                 585                 590

Ile Asp Arg Asn Asp Phe Ala Trp Phe Asn Val Asp Gln Ser Leu Val
        595                 600                 605

Glu Thr Ser Arg Ala Glu Phe Arg Ala Ala Ile Gly Thr Leu Pro Ile
    610                 615                 620

Leu Pro Ser Thr Arg Ser Leu Leu Ser Ser Asp Leu Thr Tyr Phe Ser
625                 630                 635                 640
```

-continued

```
Arg Asp Cys Ser Lys Ile Glu Asn Ala Val Lys Glu Arg Met Leu Pro
                645                 650                 655

Ala Leu Thr Leu Tyr Ala Lys Lys Ile Ala Lys Arg Asn Ala Glu Gly
            660                 665                 670

Met Leu Arg Val Thr Gly Asp Pro Leu Arg Gly Ser Ala Asp Thr Arg
        675                 680                 685

Trp Leu Ala Gln Met Leu Glu Ser Gly Lys Val Leu Val Gln Ser Pro
    690                 695                 700

Asn Ile Leu Ser Met Glu Glu Asp Gly Thr Ala Phe Val Ser Pro Asn
705                 710                 715                 720

Phe Asn Pro Ala Lys Cys Glu Glu Asp Asp Val Arg Glu Ala Gly Gly
                725                 730                 735

Val Arg Ala Arg Leu Ala Ala Thr Leu Gln Asn Met Leu Gly Asp Pro
            740                 745                 750

Arg Ile His Val Ala Ile Ser Glu Ala Ile Val Ser Met Ser Asp Val
        755                 760                 765

Arg Gly Thr Asp Leu Val Arg Leu Cys Arg Glu Leu Ile Cys Thr Thr
    770                 775                 780

Met Leu Ser Lys Lys Cys Ala Val Gln Val Val Asp Thr Gly Leu Arg
785                 790                 795                 800

Ile Ile Pro Asp Val Gln Gln Gly Gly Thr Gly Thr Leu Arg Leu Tyr
                805                 810                 815

Gln His Val Leu Phe Ala Pro Val Ala Trp Trp Ile Glu Lys Pro Ile
            820                 825                 830

Ala Ile His Leu Val Val Arg Ser Asp Leu Val Ile His Arg Asp Leu
        835                 840                 845

Thr Gly Ala Leu Ala Phe Asn Ile Glu Ser Val Arg Phe Gly Leu Arg
    850                 855                 860

Ala Ser Gln Asn Thr Val Leu Ser Thr Ser Ala Leu Leu Leu Glu Cys
865                 870                 875                 880

Lys Pro Ser Leu Leu Gly Leu Cys Cys Thr Val Asp Val Gln Pro Ser
                885                 890                 895

Glu Glu Glu Gly Val Tyr Ser Ser Arg Ala Leu His Val Met Ala Ala
            900                 905                 910

Ile Gln Arg Tyr Tyr Gly Ser Ala Tyr Ser Phe Leu Leu Val Asp Pro
        915                 920                 925

Leu Glu Asp Thr Arg Ser Thr Asn Asp Ser Leu Leu Leu Leu Val Arg
    930                 935                 940

Thr Gly Ile Gly Glu Phe Leu Asn Val Phe Gly Val Asp Gly Val Val
945                 950                 955                 960

Arg His Pro Leu Leu Cys Phe Thr Asp Ser Ser Gln Asp Val Asp Glu
                965                 970                 975

His Pro Thr Ser Glu Gln Asp Ile Tyr Asn Trp Ile Ser Lys Asn Tyr
            980                 985                 990

Pro Arg His Gly Asp Asp Ile Gly  Gly Ile Ile Ser Glu  Ala Leu Phe
        995                 1000                 1005

Asn Ala  Thr Gly Phe Gly Asn  Val Cys Lys Phe Leu  Arg Phe Ser
    1010                 1015                 1020

Val Gly  Pro Asn Leu Glu Ile  Thr Pro Val Glu Arg  Gly Gly Tyr
    1025                 1030                 1035

Arg Asn  Pro Gln Asp Val Ser  Gly Val Ile Ala Ser  Gly Pro Asp
    1040                 1045                 1050
```

-continued

```
Gly Leu  Phe Thr Ala Arg Pro  Tyr Leu Val Lys Leu  Arg Lys Gly
    1055                 1060                 1065

Ser Glu  Thr Ser Thr Leu Gly  Leu Val Cys Thr Cys  Asn Ile Ser
    1070                 1075                 1080

Val Arg  Pro Gly Gly Asn Asn  Glu Ile Leu Val Gln  Val Arg Gly
    1085                 1090                 1095

Leu Lys  Val Ser Leu Cys Ser  Gly Lys Asn Leu Leu  Lys Phe Phe
    1100                 1105                 1110

Leu Ser  Thr Ser Thr Asp Gln  Gly Ile Tyr His Glu  Gln Tyr Ser
    1115                 1120                 1125

Glu Phe  Leu His Ser Leu Glu  Pro Cys Ser Asp Leu  Ser Glu His
    1130                 1135                 1140

Cys Leu  Gln Ala Arg Val Gln  Ser Ala Lys Leu Ala  Asn Tyr Val
    1145                 1150                 1155

Arg Arg  Lys Gln His Pro Gly  Ile His Thr Gln His  Glu His Ala
    1160                 1165                 1170

Pro Gly  Gly Pro Lys Ala Ser  Asp Ala Gly Ser His  Thr Met Lys
    1175                 1180                 1185

Arg His  Gly Arg Val Leu Pro  Thr Pro Met Asp Pro  Lys Val Leu
    1190                 1195                 1200

Gln Asp  Leu Arg Ser Ser Asn  Leu Leu Ala Ala Ala  Phe Gly Gly
    1205                 1210                 1215

Glu Arg  Phe Pro Glu Asn Asp  His Ile Leu Arg Thr  Met Lys Ala
    1220                 1225                 1230

Leu Val  Asp Val Ala Ser Arg  Gly Gln Ile Ile Cys  Ala Ser Pro
    1235                 1240                 1245

Glu Arg  Gly His Lys Gly Ala  Leu Tyr Thr Asn Val  Ala Arg Met
    1250                 1255                 1260

Ser Glu  Asn Arg Leu Trp Val  Leu His Asn Ala Cys  Phe Met Thr
    1265                 1270                 1275

Pro Asp  Leu Arg Val Leu Met  Val Glu Leu His Tyr  Lys Val Asp
    1280                 1285                 1290

Arg Lys  Lys Ser Pro His Gly  Gly Arg Asp Ile Phe  Glu Ile Cys
    1295                 1300                 1305

Asp Gly  Ser Phe Asn Val Ala  Ser Gly Asp Thr Pro  Ser Lys Lys
    1310                 1315                 1320

Asp Phe  Ser Ile Arg Ile Pro  Lys Asn Val Gln Val  Ser Glu Asn
    1325                 1330                 1335

Lys Trp  Asn Ile Phe Ser Glu  Met Leu Lys Pro Pro  Val Val Pro
    1340                 1345                 1350

Glu Ser  Phe Leu Asp Lys Met  Cys Arg Trp Leu Thr  Thr Ala Trp
    1355                 1360                 1365

Asn Ser  Leu Lys Ser Phe Val  Ser Asn Ala Gly Gly  Tyr Val Met
    1370                 1375                 1380

Arg Leu  Phe Arg Ala Cys Cys  Ser Cys Val Arg Pro  Gln Asn Val
    1385                 1390                 1395

Ser Glu  Asp Asn Val Thr Leu  Leu Asp Ser Asn Arg  Asp Ser His
    1400                 1405                 1410

Glu Cys  Glu Ser Ala Val Ser  Glu Val Ser Ala Pro  Ala Pro Val
    1415                 1420                 1425

Ile Gly  Thr Ser Ser Glu His  Val His Ser Asn Asp  Val Asp Thr
    1430                 1435                 1440

Ala Gln  Ser Ser Thr Lys Ala  Lys Gly Thr Asp Gly  Lys Lys Pro
```

```
    1445                1450                1455

Ser Thr  Thr Val Pro Lys Lys  Pro Pro Arg Pro Ala  Arg Gly Ala
    1460                1465                1470

Lys Ser  Ser Ser Ala His Ser  Val Ala Gly Val Thr  Gln Gly Gly
    1475                1480                1485

Ala Gly  Asp Val Thr Arg Glu  Val Gly Gly Pro Ser  Thr Ser Val
    1490                1495                1500

Ala Asp  Pro Thr Ala Ala Ser  Ser Val Ser Gln Leu  Gln Ser Ser
    1505                1510                1515

Arg Ala  Ser Asn Val Ser Gln  Gln Gln His
    1520                1525


<210> SEQ ID NO 65
<211> LENGTH: 416
<212> TYPE: PRT
<213> ORGANISM: Anaplasma phagocytophilum

<400> SEQUENCE: 65

Met Val Cys Cys Val Ser Arg Val Val Leu Tyr Ile Ala Ser Val Ile
1               5                   10                  15

Leu Leu Met Leu Ile Met Gly Glu Asp Ala Ser Ala Ala Ile Tyr Lys
            20                  25                  30

Asp Asp Leu Pro Pro Asn Ser Lys Lys Phe Tyr Val Ala Leu Asp Tyr
        35                  40                  45

Ala Pro Ala Leu Ser Arg Val Ser Thr Phe Asp Ile Val Gly Asp Gly
    50                  55                  60

Lys Thr His Ile Ala Leu Pro Tyr Leu Lys Asn Asp Gln Glu Asp Arg
65                  70                  75                  80

Phe Asn Ala Glu Ala Ile Asp Trp Asp Ala Pro Asn Leu Ser Val Gln
                85                  90                  95

Phe Lys Asn Ser Val Leu Met Ser Trp Val Gly Ser Ile Gly Tyr Lys
            100                 105                 110

Met Met Gly Gly Arg Leu Glu Leu Glu Val Gly His Glu Lys Phe Gly
        115                 120                 125

Ala Arg Val Ser Ser Gly Glu Asn Arg Glu Glu Asn Ser Asp Val Ala
    130                 135                 140

Tyr Val Phe Phe Ser Arg Leu Leu Pro Tyr Tyr Leu Val Ser Ala Gln
145                 150                 155                 160

Tyr Glu Lys Leu Ile Ser Gly Leu Ala Asn Leu Thr Glu Asp Glu Ile
                165                 170                 175

Leu Ala Phe Ala Asn Gly Val Ala Asp Gln Arg Pro Asp Leu Asp Lys
            180                 185                 190

Lys Ile Cys Lys Lys Ala Arg Leu Gly Gly Asp Asp Arg Gly Thr Asp
        195                 200                 205

Ala Gln Ala Ala Cys Arg Asp Ser Ile Lys Gly Ala Asp Val Gly Gly
    210                 215                 220

Phe Gly Ala Phe Met Arg Lys Ala Ile Gly Thr Tyr Leu Met Trp Arg
225                 230                 235                 240

Tyr Asn Gly Gly Ser Asp Arg Tyr Gly Leu Glu Arg Gly Gly Arg Ser
                245                 250                 255

Val Asn Ser Lys Asp Ile Val Ser Asp Ile Lys Glu Leu Pro Lys Glu
            260                 265                 270

Glu Arg Lys Ile Leu Ala Gly Ile Leu Ala Ala Ala Thr Gly Tyr Gly
        275                 280                 285
```

Val Val Val Glu Ile Pro Ser Val Ala Ala Thr Ser Val Met Val Asn
    290                 295                 300

Ala Cys Tyr Asp His Asn Val Ser Leu Thr Arg Lys Arg Ala Ser Ala
305                 310                 315                 320

Tyr Ser Cys Val Gly Leu Gly Ser Thr Phe Val Glu Ile Val Asp Glu
                325                 330                 335

His Arg Ala Ala Lys Leu Ala Tyr Arg Leu Lys Ala Gly Leu Ser Tyr
            340                 345                 350

Asn Phe Ala Ser Gly Val Thr Ala Phe Val Gly Gly Phe Tyr His His
        355                 360                 365

Ile Ile Gly Asp Ser Trp Tyr Asp Arg Val Pro Met Arg Thr Val Phe
    370                 375                 380

Leu Asp Glu Lys Thr Gly Glu Arg Pro Val Lys Thr Gly Lys Val Asp
385                 390                 395                 400

Leu Ser Leu Asp Tyr Ile Gly Ala Glu Cys Gly Ile Arg Leu Ile Leu
                405                 410                 415

<210> SEQ ID NO 66
<211> LENGTH: 134
<212> TYPE: PRT
<213> ORGANISM: Anaplasma phagocytophilum

<400> SEQUENCE: 66

Met Lys Gly Lys Ser Asp Ser Glu Ile Arg Thr Ser Ser Ser Ile Arg
1               5                   10                  15

Thr Ser Ser Ser Asp Asp Ser Arg Ser Ser Asp Asp Ser Thr Arg Ile
            20                  25                  30

Arg Ala Ser Lys Thr His Pro Gln Ala Pro Ser Asp Asn Ser Ser Ile
        35                  40                  45

Leu Ser Ser Glu Asp Ile Glu Ser Val Met Arg Cys Leu Glu Glu Glu
    50                  55                  60

Tyr Gly Gln Lys Leu Ser Ser Glu Leu Lys Lys Ser Met Arg Glu Glu
65                  70                  75                  80

Ile Ser Thr Ala Val Pro Glu Leu Thr Arg Ala Leu Ile Pro Leu Leu
                85                  90                  95

Ala Ser Ala Ser Asp Ser Asp Ser Ser Ser Arg Lys Leu Gln Glu Glu
            100                 105                 110

Trp Val Lys Thr Phe Met Ala Ile Met Leu Pro His Met Gln Lys Ile
        115                 120                 125

Val Ala Ser Thr Gln Gly
    130

<210> SEQ ID NO 67
<211> LENGTH: 159
<212> TYPE: PRT
<213> ORGANISM: Anaplasma marginale

<400> SEQUENCE: 67

Leu Phe Ser Lys Glu Lys Val Gly Met Asp Ile Val Gly Val Pro Phe
1               5                   10                  15

Ser Ala Gly Arg Val Glu Lys Val Tyr Phe Asp Phe Asn Lys Tyr Glu
            20                  25                  30

Ile Lys Gly Ser Gly Lys Lys Val Leu Leu Gly Leu Val Glu Arg Met
        35                  40                  45

Lys Ala Asp Lys Arg Ser Thr Leu Leu Ile Ile Gly His Thr Asp Ser
    50                  55                  60

Arg Gly Thr Glu Glu Tyr Asn Leu Ala Leu Gly Glu Arg Arg Ala Asn
65 70 75 80

Ala Val Lys Glu Phe Ile Leu Gly Cys Asp Arg Ser Leu Ser Pro Arg
85 90 95

Ile Ser Thr Gln Ser Arg Gly Lys Ala Glu Pro Glu Val Leu Val Tyr
100 105 110

Ser Ser Asp Phe Lys Glu Ala Glu Lys Ala His Ala Gln Asn Arg Arg
115 120 125

Val Val Leu Ile Val Glu Cys Gln His Ser Val Ser Pro Lys Lys Lys
130 135 140

Met Ala Ile Lys Trp Pro Phe Ser Phe Gly Arg Ser Ala Ala Lys
145 150 155

<210> SEQ ID NO 68
<211> LENGTH: 157
<212> TYPE: PRT
<213> ORGANISM: Anaplasma marginale, subspecies Centrale

<400> SEQUENCE: 68

Asn Lys Glu Lys Val Asn Ile Asp Ile Gly Gly Val Pro Leu Ser Ala
1 5 10 15

Gly Arg Val Glu Lys Val Tyr Phe Asp Phe Asn Lys Tyr Glu Ile Lys
20 25 30

Gly Ser Gly Lys Lys Val Leu Leu Gly Leu Val Glu Arg Met Lys Ala
35 40 45

Asp Lys Met Ser Thr Leu Leu Ile Val Gly His Thr Asp Ser Arg Gly
50 55 60

Thr Glu Glu Tyr Asn Leu Ala Leu Gly Glu Arg Arg Ala Asn Ala Val
65 70 75 80

Lys Glu Phe Ile Leu Gly Cys Asp Arg Ser Leu Ser Pro Arg Ile Ser
85 90 95

Thr Gln Ser Arg Gly Lys Ala Glu Pro Glu Ile Leu Val Tyr Ser Ser
100 105 110

Asp Phe Lys Glu Ala Glu Lys Ala His Ala Gln Asn Arg Arg Val Val
115 120 125

Leu Ile Met Glu Cys Gln His Ala Ala Ser Pro Lys Lys Ala Arg Val
130 135 140

Ser Arg Trp Pro Phe Ser Phe Gly Arg Ser Ser Ala Thr
145 150 155

<210> SEQ ID NO 69
<211> LENGTH: 135
<212> TYPE: PRT
<213> ORGANISM: Ehrlichia chaffeensis

<400> SEQUENCE: 69

Asn Val Asp His Val Phe Ser Asn Thr Lys Thr Ile Glu Lys Ile Tyr
1 5 10 15

Phe Gly Phe Gly Lys Ala Thr Ile Glu Asp Ser Asp Lys Thr Ile Leu
20 25 30

Glu Lys Val Met Gln Lys Ala Glu Glu Tyr Pro Asp Thr Asn Ile Ile
35 40 45

Ile Val Gly His Thr Asp Thr Arg Gly Thr Asp Glu Tyr Asn Leu Glu
50 55 60

Leu Gly Lys Gln Arg Ala Asn Ala Val Lys Asp Phe Ile Leu Glu Arg
65 70 75 80

```
Asn Lys Ser Leu Glu Asp Arg Ile Ile Ile Glu Ser Lys Gly Lys Ser
                85                  90                  95

Glu Pro Ala Val Leu Val Tyr Ser Asn Asn Pro Glu Glu Ala Glu Tyr
            100                 105                 110

Ala His Thr Lys Asn Arg Arg Val Val Ile Thr Leu Thr Asp Asn Leu
        115                 120                 125

Ile Tyr Lys Ala Lys Ser Ser
    130                 135


<210> SEQ ID NO 70
<211> LENGTH: 135
<212> TYPE: PRT
<213> ORGANISM: Ehrlichia canis

<400> SEQUENCE: 70

Thr Thr Asp His Val Pro Leu Val Asn Thr Asp His Val Phe Ser Asn
1               5                   10                  15

Met Lys Thr Ile Glu Lys Ile Tyr Phe Asp Phe Gly Lys Ala Thr Ile
            20                  25                  30

Gly Asp Ser Asp Lys Ala Ile Leu Glu Lys Val Ile Gln Lys Ala Gln
        35                  40                  45

Lys Asp Thr Asn Thr Asn Ile Val Ile Val Gly His Thr Asp Thr Arg
    50                  55                  60

Gly Thr Asp Glu Tyr Asn Leu Glu Leu Gly Glu Gln Arg Ala Asn Ala
65                  70                  75                  80

Val Lys Asp Phe Ile Ile Glu His Asp Lys Ser Leu Glu Asn Arg Ile
                85                  90                  95

Thr Val Gln Ser Lys Gly Lys Ser Glu Pro Ala Val Leu Val Tyr Ser
            100                 105                 110

Ser Asn Pro Glu Glu Ala Glu His Ala His Ala Lys Asn Arg Arg Val
        115                 120                 125

Val Ile Thr Leu Thr Asp Asn
    130                 135


<210> SEQ ID NO 71
<211> LENGTH: 195
<212> TYPE: PRT
<213> ORGANISM: Ehrlichia ruminantium

<400> SEQUENCE: 71

Asn Ser Lys His Val Pro Leu Val Asn Val His Asn Leu Phe Ser Asn
1               5                   10                  15

Ile Lys Ala Ile Asp Lys Val Tyr Phe Asp Leu Asp Lys Thr Val Ile
            20                  25                  30

Lys Asp Ser Asp Lys Val Leu Leu Glu Lys Leu Val Gln Lys Ala Gln
        35                  40                  45

Glu Asp Pro Thr Thr Asp Ile Ile Ile Val Gly His Thr Asp Thr Arg
    50                  55                  60

Gly Thr Asp Glu Tyr Asn Leu Ala Leu Gly Glu Gln Arg Ala Asn Ala
65                  70                  75                  80

Val Arg Asp Phe Ile Ile Ser Cys Asp Lys Ser Leu Glu Lys Arg Ile
                85                  90                  95

Thr Val Arg Ser Lys Gly Lys Ser Glu Pro Ala Ile Leu Val Tyr Ser
            100                 105                 110

Asn Asn Pro Lys Glu Ala Glu Asp Ala His Ala Lys Asn Arg Arg Val
        115                 120                 125
```

-continued

```
Val Ile Thr Leu Val Asn Asn Ser Thr Ser Thr Asp Asn Lys Val Pro
    130                 135                 140

Thr Thr Thr Thr Pro Phe Asn Glu Glu Ala His Asn Thr Ile Ser Lys
145                 150                 155                 160

Asp Gln Glu Asn Asn Thr Gln Gln Gln Ala Lys Ser Asp Asn Ile Asn
                165                 170                 175

Asn Ile Asn Thr Gln Gln Lys Leu Glu Gln Asp Asn Asn Asn Thr Pro
            180                 185                 190

Glu Val Asn
        195


<210> SEQ ID NO 72
<211> LENGTH: 110
<212> TYPE: PRT
<213> ORGANISM: Ehrlichia ruminantium

<400> SEQUENCE: 72

Met Cys Ser Ser Phe Met Ala Asp Glu Asp Tyr Lys Gly Val Ile Lys
1               5                   10                  15

Gln Tyr Ile Asp Thr Val Lys Glu Ile Val Gly Asp Ser Lys Thr Phe
            20                  25                  30

Asp Gln Met Phe Glu Ser Val Val Lys Ile Gln Glu Arg Val Met Ala
        35                  40                  45

Ala Ser Ala Gln Asn Glu Ala Asn Gly Ala Leu Val Glu Gly Asp Ser
    50                  55                  60

Lys Met Lys Arg Ile Arg Ser Ala Asp Asp Ser Ile Ala Tyr Thr Gln
65                  70                  75                  80

Ser Gln Glu Leu Leu Glu Glu Leu Lys Val Leu Lys Lys Arg Ile Ala
                85                  90                  95

Arg Leu Glu Arg His Val Phe Lys Ser Asn Lys Thr Glu Val
            100                 105                 110
```

OMPA AND ASP14 IN VACCINE COMPOSITIONS AND AS DIAGNOSTIC TARGETS

FIELD OF THE INVENTION

The invention generally relates to a vaccine and diagnostic for anaplasmosis in animals and humans. In particular, the invention provides *Anaplasma phagocytophilum* outer surface protein A (OmpA) epitopes and/or *Anaplasma phagocytophilum* surface protein 14 (Asp14) epitopes.

PRIORITY

This application claims the benefit of U.S. application 61/665,223, filed Jun. 27, 2012, and U.S. application 61/698,979, filed Sep. 10, 2012. These applications are incorporated herein by reference in their entirety.

SEQUENCE LISTING

This document incorporates by reference an electronic sequence listing text file, which was electronically submitted along with this document. The text file is named 02940826TA_ST25.txt, is 87 kilobytes, and was created on Jun. 17, 2013.

BACKGROUND OF THE INVENTION

*Anaplasma phagocytophilum* (Aph) is a tick-transmitted obligate intracellular bacterium of the family Anaplasmataceae that can infect humans, livestock, companion animals and wild animals. In addition to Aph, the Anaplasmataceae family members include *Anaplasma marginale, Anaplasma platys, Ehrlichia chaffeensis, Ehrlichia canis*, and *Ehrlichia ruminatium*, among others, and all of these cause similar infections known collectively as ehrlichiosis. When humans contract an Aph infection it is more specifically known as human granulocytic anaplasmosis (HGA). An emerging and potentially fatal disease, HGA is transmitted by the same vectors that transmit Lyme Disease, primarily ticks and deer, but other animal and human hosts can complete the vector cycle and therefore extend the spread of disease. Since HGA became a reportable disease in the U.S. in 1999, the number of cases has risen annually, reaching 1,761 in 2010. Since diagnostic tools for HGA are lacking, this number of actual cases is likely to be much higher. HGA is increasingly recognized in Europe and Asia, and Aph infection is now the most widespread tick-transmitted disease of animals in Europe.

As the name implies, an obligate intracellular bacterium must enter a target cell in its human or animal host to survive, replicate, and move to the next host. When an *Anaplasma* spp. or *Ehrlichia* spp. infected tick bites a subject, the bacteria is transferred from the tick salivary glands into the tissues of the host or into the bloodstream where they bind to the surface of host cells and are taken up into vacuoles that form around each bacterium. A resident bacterium prevents the vacuole from merging with lysosomes. In doing so, the bacterium converts the cell into a protective niche that favors bacterial survival and remains in circulation to enable it to complete its zoonotic cycle. While the hallmark of these diseases is Aph colonization of neutrophils, other pathological findings can include leukopenia, thrombocytopenia, and elevated serum transaminase levels. Anaplasmosis is marked by fever and increased susceptibility to potentially fatal opportunistic infections.

Infected neutrophils in a host can be ingested in a second tick bite/bloodmeal. In this manner the disease may be transferred to another subject bitten subsequently. However, HGA can also be transmitted perinatally or by blood transfusion, and possibly nosocomially. Blocking infection of neutrophils could conceivably prevent all of these types of dissemination of Aph infection and the increased risk of opportunistic infections that can accompany the disease. Furthermore, targeting Aph proteins that are conserved among related Anaplasmataceae family members might also reduce or block transmission of disease caused by related Anaplasmataceae family members.

In addition to neutrophils, Aph has been detected in the microvascular endothelium of heart and liver in experimentally infected severe combined immunodeficiency mice. Promyelocytic and endothelial cell lines are useful in vitro models for studying Aph-host cell interactions. When naïve neutrophils or HL-60 cells are overlaid on Aph-infected endothelial cells, the bacterium rapidly transmigrates into the myeloid cells. These observations demonstrated that Aph infects endothelial cells in vivo and suggested that the bacterium may transmigrate between endothelial cells and neutrophils during the course of mammalian infection. Thus, targeting the Aph invasins that mediate infection of endothelial cells may prevent movement of the bacteria into the microvasculature of heart and liver in an affected subject by blocking the mechanism of endothelial cell-to-neutrophil transfer.

The Aph genome has now been sequenced and annotated. The annotated Aph genome (HZ strain, isolated from a human patient) can be found on the website at cmr.jcvi.org, and more specifically on the page found at cmr.jcvi.org/tigr-scripts/CMR/GenomePage.cgi?org_search=&org=gaph. Another website is the page found at ncbi.nlm.nih.gov, more specifically on the page found at ncbi.nlm.nih.gov/Taxonomy/Browser/wwwtax.cgi?mode-Info&id=948&1v1=3&keep=1&srchmode=1&unlock. This information has promoted some progress regarding diagnosis of anaplasmosis and protecting subjects from infection. U.S. Pat. No. 7,906,296 B2 to Beall et al teaches that *Anaplasma platys* (Apl), formerly known as *Ehrlichia platys*, causes tick-born anaplasmosis in dogs. Beall further teaches the uses of Apl polypeptides. The Apl sequences were amplified from a blood sample of a dog known to be infected with Apl in order to develop methods for detecting the presence of antibodies to Apl and/or Aph in dog sera. Beall also teaches that peptides including Apl P44, encoding a major surface protein, might be used to elicit an immune response in vivo and confer resistance to anaplasmosis caused by Apl or Aph. U.S. Pat. No. 8,158,370 B2 to Liu el al. teaches that polypeptide sequences amplified from either Apl or Aph can be used in diagnostic assays, or to induce an immune reaction that might confer protection from Apl or Aph infection. The Aph sequences used by Liu were derived from APH_0915, encoding a protein of unknown function. More recently, Liu et al., in U.S. Pat. No. 8,303,959 and US 2013/0064842, teaches the use of four strain variants of Aph P44 surface proteins to diagnosis and protect against anaplasmosis.

Despite these teachings, there are currently no human or animal vaccines against anaplasmosis caused by any of the Anaplasmataceae family members. Antibiotic treatments with doxycycline or tetracycline can be effective, but tools for rapid and definitive diagnosis in any species other than dogs are lacking. The current gold standard serologic test for diagnosis of anaplasmosis in humans is indirect immunofluorescence assays (IFA) performed as timed pairs over a period of a few weeks, only available in specialized reference laboratories. This assay measures non-specific increases in IgM and IgG antibody levels. However, IgM antibodies, which usually rise at the same time as IgG near the end of the first week of illness and remain elevated for months or longer, are even less specific than IgG antibodies and more likely to result in a false positive. Serologic tests based on enzyme immunoassay (EIA) technology are available from some commercial laboratories. However, EIA tests are qualitative rather than quantitative, meaning they only provide a positive/negative result, and are less useful to measure changes in antibody titers between paired specimens. Furthermore, some EIA assays rely on the evaluation of IgM antibody alone, which again may have a higher frequency of false positive results. Between 5-10% of currently healthy people in some areas may have elevated antibody titers due to past exposure to Aph or related family members. If only one sample is tested it can be difficult to interpret. A four-fold rise in antibody titer is needed to achieve significance in paired samples taken weeks apart.

Therefore, the need remains for compositions and methods to rapidly and accurately diagnosis new cases and to provide adequate vaccination against Anaplasmataceae infections that cause anaplasmosis and HGA.

SUMMARY

An embodiment of the invention is a composition including one or more isolated polypeptides, wherein at least one of said one or more polypeptides is or includes SEQ ID NO:03 or SEQ ID NO:06. The one or more polypeptides may be linked to an amino acid spacer, an amino acid linker, a signal sequence, a stop transfer sequence, a transmembrane domain, a protein purification ligand, a heterologous protein, or one or more additional polypeptides comprising SEQ ID NO:01, 02, 03, 04, 05 or 06, or a combination thereof. An exemplary embodiment is one or more polypeptides linked to a protein purification ligand, and protein purification ligands are a peptide encoding a histidine tag.

Another embodiment of the invention comprises one or more polypeptides selected from the group consisting of SEQ ID NO:01. SEQ ID NO:02, and SEQ ID NO:03. Another embodiment of the invention comprises one or more polypeptides selected from the group consisting of SEQ ID NO:04, SEQ ID NO:05, and SEQ ID NO:06.

Another embodiment of the invention is a method of protecting a subject from acquiring a zoonotic disease and/or treating a zoonotic disease in a subject by the step of administering a composition including one or more isolated polypeptides, wherein at least one of said one or more polypeptides is or includes SEQ ID NO:03 or SEQ ID NO:06. The one or more polypeptides may be linked to an amino acid spacer, an amino acid linker, a signal sequence, a stop transfer sequence, a transmembrane domain, a protein purification ligand, a heterologous protein, or one or more additional polypeptides comprising SEQ ID NO:01, 02, 03, 04, 05 or 06; or a combination thereof. The zoonotic disease may be one caused by an obligate intracellular Anaplasmataceae bacterium selected from the group consisting of *Anaplasma phagocytophilum, Anaplasma marginale, Anaplasma platys, Ehrlichia chaffeensis, Ehrlichia canis*, and Ehrlicia *ruminatium*. When the subject is a human, and the zoonotic disease may be human granulocytic anaplasmosis (HGA). When the subject is an animal, the zoonotic disease may be anaplasmosis.

Another embodiment of the invention is a method of detecting antibodies that specifically bind an Anaplasmataceae polypeptide in a test sample. The method may include the steps of contacting a test sample, under conditions that allow polypeptide-antibody complexes to form, with a composition that includes at least one or more polypeptides encoding all or a portion of SEQ ID NO:01 or SEQ ID NO:04, and detecting said polypeptide-antibody complexes, wherein the detection is an indication that antibodies specific for Anaplasmataceae Asp14 or OmpA are present in the test sample. The method may be an assay selected from the group consisting of an immunoblot and an enzyme-linked immunosorbent assay (ELISA). An exemplary embodiment of this methodology may include using at least one polypeptide which is or includes SEQ ID NO:03 or SEQ ID NO:06 in the assay, whereby infection with obligate intracellular Anaplasmataceae is determined from a serum sample exhibiting antibody binding with the at least one polypeptide.

BRIEF DESCRIPTION OF THE FIGURES

FIGS. 6A and B. Alignment of OmpA (SEQ ID NO:04) with *Anaplasma* and *Ehrlichia* species homologs AM854 (SEQ ID NO: 31), ACHIS_00486 (SEQ ID NO:33), ECH_0462 (SEQ ID NO:39), Ecaj_0563 (SEQ ID NO:45), and Erum 5620 (SEQ ID NO:51) with regions of identity and similarity shaded, and predicted 3D structure with extracellular loop and helix are indicated by arrows.

FIG. 11. An alignment of Asp14 residues 101-115, which constitute a conserved domain among homologs from *Anaplasma* and *Ehrlichia* species Asp14 (SEQ ID NO:01), AM936 (SEQ ID NO:13), ACHIS_00403 (SEQ ID NO:15), ECH_0377 (SEQ ID NO:19), Ecaj_0636 (SEQ ID NO:23), and Erum6320 (SEQ ID NO:27) with regions of identity and similarity shaded.

FIG. 14. Locations of linker insertion mutations that identify regions required to disrupt the ability of OmpA to antagonize Aph infection, showing alignment of OmpA (SEQ ID NO: 10) with *Anaplasma* and *Ehrlichia* species homologs AM854 (SEQ ID NO: 32), ACHIS_00486 (SEQ ID NO: 34), ECH_0462 (SEQ ID NO:40), Ecaj_0563 (SEQ ID NO:46), and Erum 5620 (SEQ ID NO:52) with regions of identity and similarity shaded.

DETAILED DESCRIPTION

Figure 1A:
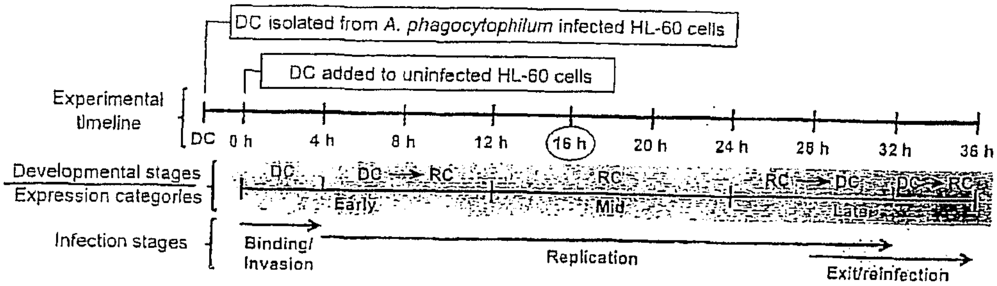
FIGS. 1A and B. Timeline of Aph infection cycle and differential transcription profiling of OMP candidate genes throughout the Aph infection cycle.

Aspects of the invention are related to diagnosing, preventing, and treating zoonotic diseases caused by Anaplasmataceae bacteria. The diseases affect both animals and humans and are collectively referred to as anaplasmosis, but more specifically known as HGA when transmitted to humans. Aph surface proteins OmpA and Asp14 have been identified as mediating bacteria-host cell binding and entry. Thus, the surface proteins OmpA and Asp14 and fragments thereof can be used for diagnosing whether a patient has been suffering from Aph infection. Specifically, if antibodies to one or more of OmpA or Asp14 are identified in serum or other biological material from a subject suspected of an Aph infection by suitable assay, such as ELISA or immunoblot, where, for example, the antibodies bind to or interact with OmpA or Asp14 proteins or fragments thereof, then it can be determined that the subject has been exposed to, infected with, or is currently infected with Aph. Furthermore, administration of OmpA or Asp14 proteins or fragments, or nucleic acids encoding for OmpA or Asp14 proteins, such as in forms where the nucleic acids are present with a vector such as a viral vector, or are present as purified peptides, polypeptides or proteins in a pharmaceutically acceptable carrier, can provide an immunogenic response in the subject and protection from subsequent Aph infection, or provide for treatment by the production of antibodies to Aph infection in a subject that is already infected.

The critical regions of Asp14 and OmpA that mediate infection are highly conserved among family members Aph, *A. marginale*, and closely related *Ehrlichia* species, such as *E. chaffeensis, E. canis*, and *E. ruminatium*, and may be highly conserved in *A. platys*. In particular, Aph and *A. marginale* are closely related and express many gene homologs, including Asp14, OmpA and other surface antigens. The high degree of conservation makes these surface proteins ideal for producing a vaccine or immunogenic composition to provide protection from or therapy for multiple pathogens in humans and animals.

In one embodiment, the composition of the invention comprises one or more isolated and purified recombinant polypeptides. Each polypeptide comprises amino acid sequences encoding an Asp14 or an OmpA invasin domain that mediates uptake of Aph bacteria into host cells. The Asp14 invasin domain lies within aal13-124 (SEQ ID NO:03). In other embodiments, polypeptide fragments such as Asp14 aa101-124 (SEQ ID NO:02) or the full length protein (SEQ ID NO:01) are used. In another embodiment, the composition of the invention comprises the invasin domain of OmpA, which lies within aa 59-74 (SEQ ID NO:06). In other embodiments, a larger fragment of OmpA encompassing aa19-74 (SEQ ID NO:05), or the full length OmpA protein (SEQ ID NO:06) is used. It is contemplated that virtually any protein sequence, as well as its corresponding nucleic acid sequence coding for the protein sequence that is or includes SEQ ID NO: 04 may be used. This would include the full length sequence (e.g., SEQ ID NO:04) as well as any sequence of, for example 5-50 (or less than 5 or more than 50) amino acids before the beginning or at the end of the amino acid sequence defined by SEQ ID NO:04, and this can include amino acids which are present in SEQ ID NO:06 as well as amino acids which are from different species (e.g., a chimera) or from a synthetic sequence, e.g., a histidine or GST tag. While the invention may comprise one, or a plurality, or multiple copies of any single one of these polypeptides, yet another embodiment is a mixture of at least two of the polypeptides encoded by SEQ ID NO:01, 02, 03, 04, 05 and 06. Any of these polypeptides may be produced by means of chemical synthesis or recombinant techniques well-known to those of ordinary skill in the art of molecular biology.

There is currently no means for preventing transmission of the bacteria causing anaplasmosis or HGA. While antibiotic treatments exist, these treatments are not advised for some groups of patients. In one embodiment, the invention is a vaccine for prevention or treatment of anaplasmosis and HGA. One embodiment of the invention is a pharmaceutically acceptable composition comprising one or a plurality of any one of or a mixture of at least two amino acid sequences which are or include the amino acid sequences which are identified as SEQ ID NO:01, 02, 03, 04, 05 and 06. Administration of the composition of the invention stimulates an immune response in a subject and production of antibodies against Asp14, OmpA, or both. Because Asp14 and OmpA are on the outer surface of Aph bacteria, antibodies produced by the subject will block binding of bacteria to host cells and interfere with uptake into vacuoles. Bacteria unable to enter host cells will be detected by the host immune system and cleared from the body. Blockade can occur at the point of entry into neutrophils or endothelial cells or transfer between these two host cell types. Interruption of the zoonotic life cycle provides a further benefit to public health and well-being by breaking the chain of disease transmission to others.

Aside from commercial assays to detect Apl in dogs, there is no specific assay to rapidly or confirm Anaplasmataceae infection, or accurately diagnose HGA or anaplasmosis. In another embodiment, the invention provides a method to detect the presence of Aph Asp14 or OmpA in assays of biological samples obtained from subjects to bind to antibodies produced by an Anaplasmataceae-infected individual, either of which would be diagnostic for HGA or anaplasmosis. The preferred composition for diagnostic testing may comprise either full length Asp14 (SEQ ID NO: 3) or OmpA (SEQ ID NO:04). However, compositions comprising fragments of Asp14, such as SEQ ID NO:01 and/or 02, are also contemplated, as are any mixtures of at least two of SEQ ID NO:01, 02, and 03. Likewise, composition comprising fragments of OmpA, such as SEQ ID NO:06 and/or 05, and any mixtures of at least two of SEQ ID NO:04, 05, and 06. The assay used to detect antibodies may be any type of immunoassay, such as an immunoblot or an enzyme-linked immunosorbent assay. The test sample may be any type of body fluid, such as blood, plasma, serum, urine, saliva, or other body fluid. Tissues or cells may also be used, such as tissue sections or cell preparations adhered to slides or coverslips for immunohistochemical staining. The preferred embodiment is an ELISA with each protein type to independently detect antibodies to Asp14, and OmpA, however, a combination to detect Asp14 and OmpA antibodies in one ELISA is also contemplated.

In order to facilitate the understanding of the present invention, the following definitions are provided:

Aph: *Anaplasma phagocytophilum* or *A. phagocytophilum*, an Anaplasmataseae family bacterium that is tick-born and causes anaplasmosis in humans and animals.

Apl: *Anaplasma platys* or *A. platys*, an Anaplasmataseae family member bacterium that is tick-born and causes anaplasmosis that is restricted to dogs.

Anaplasmataceae: a family of closely related bacteria, including *Anaplasma* and *Ehrlichia* species. The genera *Neorickettsia* and Wolbachhia are also Anaplasmataceae, bacteria but do not cause anaplasmosis.

Antigen: term used historically to designate an entity that is bound by an antibody, and also to designate the entity that induces the production of the antibody. More current usage limits the meaning of antigen to that entity bound by an antibody, while the word "immunogen" is used for the entity that induces antibody production. Where an entity discussed herein is both immunogenic and antigenic, reference to it as either an immunogen or antigen will typically be made according to its intended utility. The terms "antigen", "antigenic region" "immunogen" and "epitope" may be used interchangeably herein. As used herein, an antigen, immunogen or epitope is generally a portion of a protein (e.g. a peptide or polypeptide).

Asp14: 14-kilodalton Aph surface protein. OmpA homologs are expressed by Anaplasmataceae family members, including Aph, *A. marginate, Ehrlichia chaffeensis, E. canis, E. ewingii*, and *E. ruminatium.*

OmpA: Outer membrane protein A. OmpA homologs are expressed by Anaplasmataceae family members, including Aph, *A. marginate, Ehrlichia chaffeensis, E. canis, E. ewingii*, and *E. ruminatium.*

DC and RC: Aph undergoes a biphasic developmental cycle, the kinetics of which have been tracked in promyelocytic HL-60 cells. The cycle begins with attachment and entry of an infectious dense-cored (DC) organism. Once intracellular, the DC differentiates to the non-infectious reticulate cell (RC) form and replicates by binary fission to produce a bacteria-filled organelle called a morula. Later, the RCs transition back to DCs, which initiate the next round of infection.

Epitope: a specific chemical domain on an antigen that is recognized by a B-cell receptor, and which can be bound by secreted antibody. The term as used herein is interchangeable with "antigenic determinant".

Immunodominant epitope: The epitope on a molecule that induces the dominant, or most intense, immune response. The immunodominant epitope would elicit the greatest antibody titer during infection or immunization, as measured by, for example, the fraction of reactivity attributable to a certain antigen or epitope in an enzyme-linked immunosorbant assay as compared with the total responsiveness to an antigen set or entire protein.

Invasin domain: An invasin domain is a region of a pathogen's protein that binds a host cell and mediates intracellular signaling and pathogen entry into the host cell. In some cases, uptake of the pathogen results in the formation of a vacuole in which the intracellular pathogen will reside. The invasin domains of the invention are linear amino acid sequences within Asp14, OmpA, or other surface proteins that are found on the outer membrane of the bacteria Aph and other Anaplasmataceae family members, and can vary slightly from one family member to the next. However, the invasin domain in each Asp14 homolog is critical for uptake of bacteria into host cells (known to be neutrophils and endothelial cells in the case of Anaplasmataceae).

Linker sequences: short peptide sequences encoding functional units that may be engineered or otherwise added at the ends or within recombinant proteins, polypeptides, peptides of interest. Linker sequences may be used as "handles" for protein purification, as detectable signals of expression or binding to other proteins or macromolecules, to modulate tertiary structure, or enhance antigenicity. Examples of linker sequences include but are not limited to an amino acid spacer, an amino acid linker, a signal sequence, a stop transfer sequence, a transmembrane domain, and a protein purification ligand.

LINKER: a program to generate linker sequences for fusion proteins. Protein Engineering 13(5): 309-312, which is a reference that describes unstructured linkers. Structured (e.g. helical) sequence linkers may also be designed using, for example, existing sequences that are known to have that secondary structure, or using basic known biochemical principles to design the linkers.

Tags: Recombinant protein sequences that can be added to the N- or C-terminus of a recombinant protein for the purpose of identification or for purifying the recombinant protein for subsequent uses. Examples of recombinant protein tags that may be useful in practicing the invention include but are not limited to glutathione-S-transferease (GST), poly-histidine, maltose binding protein (MBP), FLAG, V5, halo, myc, hemaglutinin (HA), S-tag, calmodulin, tag, streptavidin binding protein (SBP), Softag1™, Softag3™, Xpress tag, isopeptag, Spy Tag, biotin carboxyl carrier protein (BCCP), GFP, Nus-tag, strep-tag, thioredoxin tag, TC tag, and Ty tag. All such tags are well-known to those of ordinary skill in the art of recombinant protein production.

Epitope: An epitope may comprise a single, non-interrupted, contiguous chain of amino acids joined together by peptide bonds to form a peptide or polypeptide. Such an epitope can be described by its primary structure, i.e. the linear sequence of amino acids in the peptide chain. Epitope may also refer to conformational epitopes, which are comprised of at least some amino acids that are not part of an uninterrupted, linear sequence of amino acids, but which are brought into proximity to other residues in the epitope by secondary, tertiary and/or quaternary interactions of the protein. Residues in conformational epitopes may be located far from other resides in the epitope with respect to primary sequence, but may be spatially located near other residues in the conformational epitope due to protein folding.

Protein: Generally means a linear sequence of about 100 or more amino acids covalently joined by peptide bonds.

Polypeptide: Generally means a linear sequence of about 55 to about 100 amino acids covalently joined by peptide bonds.

Peptide: Generally means a linear sequence of about 55 or fewer amino acids covalently joined by peptide bonds.

Note: The terms "peptide", "polypeptide" and "protein" may be used interchangeably herein.

Chimeric or fusion peptide or polypeptide: a recombinant or synthetic peptide or polypeptide whose primary sequence comprises two or more linear amino acid sequences which do not occur together in a single molecule in nature. The two or more sequences may be, for example, a peptide (e.g. an epitope or antigenic region) and a linker sequence, or two or more peptides (which may be the same or different) which are either contiguous or separated by a linker sequences, etc.

Tandem repeats: two or more copies of nucleic acid or amino acid sequences encoding the same peptide, which are arranged in a linear molecule and are either contiguous or separated by a linker sequences, etc.

Original or native or wild type sequence: The sequence of a peptide, polypeptide, protein or nucleic acid as found in nature.

Recombinant peptide, polypeptide, protein or nucleic acid: peptide, polypeptide, protein or nucleic acid that has been produced and/or manipulated using molecular biology techniques such as cloning, polymerase chain reaction (PCR), etc.

Synthetic peptide, polypeptide, protein or nucleic acid: peptide, polypeptide, protein or nucleic acid that has been produced using chemical synthesis procedures.

Type-specific: associated primarily with a single phyletic group.

Surface protein: A protein located on the outer surface membrane of a cell or bacterium.

TABLE 1

Aph Sequence Listing with SEQ ID Numbers.

| SEQ ID NO | PROTEIN NAME | GENBANK ACCESSION # AND NAME | AMINO ACID SEQUENCE |
|---|---|---|---|
| SEQ ID NO: 01 | Full-length Asp14 | YP_504865 APH_0248 | MIPLAPWKSISVVYMSGSDEYKEIIKQCIGSVKEVFGEGRFDDVVASIMKMQEKVLASSMQQDDTGTVGQIESGEGSGARLSDEQVQQLMNSIREEFKDDLRAIKRRILKLERAVYGANTPKES |
| SEQ ID NO: 02 | Asp14 aa101-124 | APH_0248 | LRAIKRRILKLERAVYGANTPKES |
| SEQ ID NO: 03 | Asp 14 aa113-124 | APH_0248 | RAVYGANTPKES |
| SEQ ID NO: 04 | Full length OmpA | YP_504946 APH_0338 | MLRRSSFFCLLALLSVTSCGTLLPDSNVGVGRHDLGSHRSVAFAKKVEKVYFDIGKYDLKGPGKKVILELVEQLRQDDSMYLVVIGHADATGTEEYSLALGEKRANAVKQFIIGCDKSLAPRVTTQSRGKAEPEVLVYSTDAQEVEKANAQNRRAVIVVEFAHIPRSGVADMHAPVASSITSENSNASAEGEDMEASEFSSAIAN |
| SEQ ID NO: 05 | OmpA aa19-74 | APH_0338 | CGTLLPDSNVGVGRHDLGSHRSVAFAKKVEKVYFDIGKYDLKGPGKKVILELVEQLR |
| SEQ ID NO: 06 | OmpA aa59-74 | APH_0338 | LKGPGKKVILELVEQL |
| SEQ ID NO: 07 | OmpA aa48-56 | APH_0338 | EKVYFDIGK |
| SEQ ID NO: 08 | OmpA | APH_0338 | GHADATGTEEYSLALG |

TABLE 1-continued

Aph Sequence Listing with SEQ ID Numbers.

| SEQ ID NO | PROTEIN NAME | GENBANK ACCESSION # AND NAME | AMINO ACID SEQUENCE |
|---|---|---|---|
| SEQ ID NO: 09 | OmpA | APH_0338 | LVYSTDAQEVEKANAQNRRAV |
| SEQ ID NO: 10 | OmpA | APH_0338 | PDSNVGVGRHDLGSHRSVAFAKKVEKVYFDIGKYDLKGPGKKVILELVEQLRQDDSMYLVVIGHADATGTEEYSLALGEKRANAVKQFIIGCDKSLAPRVTTQSRGKAEPEVLVYSTDAQEVEKANAQNRRAVIVVEFAHIPRSGVADM |
| SEQ ID NO: 11 | Asp14 aa101-112 | APH_0248 | LRAIKRRILKLE |
| SEQ ID NO: 12 | Asp14 aa19-60 | APH_0248 | DEYKEIIKQCIGSVKEVFGEGRFDDVVASIMKMQEKVLASSM |

TABLE 2

Asp14 Homologs Sequence Listing with SEQ ID Numbers

| | | | |
|---|---|---|---|
| SEQ ID NO: 13 | *Anaplasma marginale* | AM936 | MSGEDEYKEIIRQCIGSVKEVFGEGRFDDVVASIMKMQEKVLASSMKDGDPVGQIAADGVGNELYDRIADRLEERVSQKISEDLRIIKKRLLRLERVVLGGGSVSGDAAAHQVSGNQPSQQNSSAAAEGG |
| SEQ ID NO: 14 | *A. marginale* | AM936 | LGGGSVSGDAAAHQVSGNQPSQQNSSAAAEGG |
| SEQ ID NO: 15 | *A. marginale* subspecies *Centrale* | ACIS_00403 | MSGEDEYKEIIRQCIGSVKEVFGEGRFDDVVASIMKMQEKVLASSMKDGDPVGQIAADGVGNELYDRIADRLEERVSQKISEDLRIIKKRLLRLERVVLGGGSVSGDAAAAHQVSGNQPSQQNSSAAAEGG |
| SEQ ID NO: 16 | *A. marginale* subspecies *Centrale* | ACIS_00403 | LGGGSVSGDAAAAHQVSGNQPSQQNSSAAAEGG |
| SEQ ID NO: 17 | *A. marginale* & *A. marginale* subspecies *Centrale* | AM936 & ACIS-00403 | MSGEDEYKEIIRQCIGSVKEVFGEGRFDDVVASIMKMQEKVLASSM |
| SEQ ID NO: 18 | *A. marginale* & *A. marginale* subspecies *Centrale* | AM936 & ACIS-00403 | DLRIIKKRLLRLERVV |
| SEQ ID NO: 19 | *Ehrlichia chaffeensis* | ECH_0377 | MAEDDYKGVIKQYIDTVKEIVGDSKTFDQMFESVVRIQERVMAANAQNNEDGVIDNGDQVKRIGSSTSESISNTEYKELMEELKVIKKRILRLERKILKPKEEV |

TABLE 2-continued

Asp14 Homologs Sequence Listing with SEQ ID Numbers

| | | | |
|---|---|---|---|
| SEQ ID NO: 20 | *E. chaffeensis* | ECH_0377 | MAEDDYKGVIKQYIDT<br>VKEIVGDSKTFDQMFE<br>SVVRIQERVM |
| SEQ ID NO: 21 | *E. chaffeensis* | ECH_0377 | ELKVIKKRILRLE |
| SEQ ID NO: 22 | *E. chaffeensis* | ECH_0377 | RKILKPKEEV |
| SEQ ID NO: 23 | *E. canis* | Ecaj_0636 | MADDEYKGVIQQYINT<br>VKEIVSDSKTFDQMFE<br>SVVKIQERVMEANAQN<br>DDGSQVKRIGSSTSDS<br>ISDSQYKELIEELKVI<br>KKRLLRLEHKVLKPKE<br>GA |
| SEQ ID NO: 24 | *E. canis* | Ecaj_0636 | MADDEYKGVIQQYINT<br>VKEIVSDSKTFDQMFE<br>SVVKIQERVM |
| SEQ ID NO: 25 | *E. canis* | Ecaj_0636 | ELKVIKKRLLRLE |
| SEQ ID NO: 26 | *E. canis* | Ecaj_0636 | HKVLKPKEGA |
| SEQ ID NO: 27 | *E. ruminantium* | Erum6320 | MADEDYKGVIKQYIDT<br>VKEIVGDSKTFDQMFE<br>SVVKIQERVMAASAQN<br>EANGALVEGDSKMKRI<br>RSADDSIAYTQSQELL<br>EELKVLKKRIARLERH<br>VFKSNKTEA |
| SEQ ID NO: 28 | *E. ruminantium* | Erum6320 | MADEDYKGVIKQYIDT<br>VKEIVGDSKTFDQMFE<br>SVVKIQERVM |
| SEQ ID NO: 29 | *E. ruminantium* | Erum6320 | ELKVLKKRIARLE |
| SEQ ID NO: 30 | *E. ruminantium* | Erum6320 | RHVFKSNKTEA |

TABLE 3

OmpA Homologs Sequence Listing with SEQ ID Numbers

| | | | |
|---|---|---|---|
| SEQ ID NO: 31 | *Anaplasma marginale* | AM854 | MLHRWLALCFLASFAV<br>TGCGLFSKEKVGMDIV<br>GVPFSAGRVEKVYFDF<br>NKYEIKGSGKKVLLGL<br>VERMKADKRSTLLIIG<br>HTDSRGTEEYNLALGE<br>RRANAVKEFILGCDRS<br>LSPRISTQSRGKAEPE<br>VLVYSSDFKEAEKAHA<br>QNRRVVLIVECQHSVS<br>PKKKMAIKWPFSFGRS<br>AAKQDDVGSSEVSDEN<br>PVDDSSEGIASEEAAP<br>EEGVVSEEAAEEAPEV<br>AQDSSAGVVAPE |
| SEQ ID NO: 32 | *A. marginale* | AM854 | LFSKEKVGMDIVGVPF<br>SAGRVEKVYFDFNKYE<br>IKGSGKKVLLGLVERM<br>KADKRSTLLII |

TABLE 3-continued

OmpA Homologs Sequence Listing with SEQ ID Numbers

| | | | |
|---|---|---|---|
| SEQ ID NO: 33 | *A. marginale* subspecies *Centrale* | ACIS_00486 | MLHRWLALCLLASLAV<br>TGCELFNKEKVNIDIG<br>GVPLSAGRVEKVYFDF<br>NKYEIKGSGKKVLLGL<br>VERMKADKMSTLLIVG<br>HTDSRGTEEYNLALGE<br>RRANAVKEFILGCDRS<br>LSPRISTQSRGKAEPE<br>ILVYSSDFKEAEKAHA<br>QNRRVVLIMECQHAAS<br>PKKARVSRWPFSFGRS<br>SATQQDNGGGTVAAGS<br>PGEDAPAEVVEPEETQ<br>EAGE |
| SEQ ID NO: 34 | *A. marginale* subspecies *Centrale* | ACIS_00486 | LFNKEKVNIDIGGVPL<br>SAGRVEKVYFDFNKYE<br>IKGSGKKVLLGLVERM<br>KADKMSTLLIV |
| SEQ ID NO: 35 | *A. marginale* & *A. marginale* subspecies *Centrale* | AM854 & ACS-00486 | AGRVEKVYFDFNKYEI<br>KGSGKKVLLGLVERMK<br>AD |
| SEQ ID NO: 36 | *A. marginale* & *A. marginale* subspecies *Centrale* | AM936 & ACIS-00403 | GHTDSRGTEEYNLALG |
| SEQ ID NO: 37 | *A. marginale* & *A. marginale* subspecies *Centrale* | AM854 & ACS-00486 | RRANAVKEFILGCDRS<br>LSPRISTQSRGKAE |
| SEQ ID NO: 38 | *A. marginale* & *A. marginale* subspecies *Centrale* | AM854 & ACIS-00486 | LVYSSDFKEAEKAHAQ<br>NRRVVLI |
| SEQ ID NO: 39 | *Ehrlichia chaffeensis* | ECH_0462 | MKHKLVFIKFMLLCLI<br>LSSCKTTDHVPLVNVD<br>HVFSNTKTIEKIYFGF<br>GKATIEDSDKTILEKV<br>MQKAEEYPDTNIIIVG<br>HTDTRGTDEYNLELGK<br>QRANAVKDFILERNKS<br>LEDRIIIESKGKSEPA<br>VLVYSNNPEEAEYAHT<br>KNRRVVITLTDNLIYK<br>AKSSDKDPSSNKTEQ |
| SEQ ID NO: 40 | *Ehrlichia chaffeensis* | ECH_0462 | NVDHVFSNTKTIEKIY<br>FGFGKATIEDSDKTIL<br>EKVMQKAEEYPDTNII<br>IV |
| SEQ ID NO: 41 | *Ehrlichia chaffeensis* | ECH_0462 | IEDSDKTILEKVMQKA<br>EEYPDTNIIIV |
| SEQ ID NO: 42 | *Ehrlichia chaffeensis* | ECH_0462 | GHTDTRGTDEYNLELG<br>E |
| SEQ ID NO: 43 | *Ehrlichia chaffeensis* | ECH_0462 | QRANAVKDFILERNKS<br>LEDRIIIESKGKSEPA<br>V |
| SEQ ID NO: 44 | *Ehrlichia chaffeensis* | ECH_0462 | LVYSNNPEEAEYAHTK<br>NRRVVI |
| SEQ ID NO: 45 | *E. canis* | Ecaj_0563 | MKHKLVFIKFILLCLI<br>LSSCKTTDHVPLVNTD<br>HVFSNMKTIEKIYFDF<br>GKATIGDSDKAILEKV<br>IQKAQKDTNTNIVIVG<br>HTDTRGTDEYNLELGE |

TABLE 3-continued

| OmpA Homologs Sequence Listing with SEQ ID Numbers | | | |
|---|---|---|---|
| | | | QRANAVKDFIIEHDKSLENRITVQSKGKSEPAVLVYSSNPEEAEHAHAKNRRVVITLTDNGNKTSQ |
| SEQ ID NO: 46 | *E. canis* | Ecaj_0563 | TTDHVPLVNTDHVFSNMKTIEKIYFDFGKATIGDSDKAILEKVIQKAQKDTNTNIVIV |
| SEQ ID NO: 47 | *E. canis* | Ecaj_0563 | GDSDKAILEKVIQKAQKDTNTNIVIV |
| SEQ ID NO: 48 | *E. canis* | Ecaj_0563 | GHTDTRGTDEYNLELGE |
| SEQ ID NO: 49 | *E. canis* | Ecaj_0563 | QRANAVKDFIIEHDKSLENRITVQSKGKSEPAV |
| SEQ ID NO: 50 | *E. canis* | Ecaj_0563 | LVYSSNPEEAEHAHAKNRRVVI |
| SEQ ID NO: 51 | *E. ruminantium* | Erum5620 | MRYQLIVANLILLCLTLNGCHFNSKHVPLVNVHNLFSNIKAIDKVYFDLDKTVIKDSDKVLLEKLVQKAQEDPTTDIIIVGHTDTRGTDEYNLALGEQRANAVRDFIISCDKSLEKRITVRSKGKSEPAILVYSNNPKEAEDAHAKNRRVVITLVNNSTSTDNKVPTTTTPFNEEAHNTISKDQENNTQQQAKSDNINNINTQQKLEQDNNNTPEVN |
| SEQ ID NO: 52 | *E. ruminantium* | Erum5620 | NSKHVPLVNVHNLFSNIKAIDKVYFDLDKTVIKDSDKVLLEKLVQKAQEDPTTDIIIV |
| SEQ ID NO: 53 | *E. ruminantium* | Erum5620 | DSDKVLLEKLVQKAQEDPTTDIIIV |
| SEQ ID NO: 54 | *E. ruminantium* | Erum5620 | GHTDTRGTDEYNLALGE |
| SEQ ID NO: 55 | *E. ruminantium* | Erum5620 | QRANAVRDFIISCDKSLEKRITVRSKGKSEPAI |
| SEQ ID NO: 56 | *E. ruminantium* | Erum5620 | LVYSNNPKEAEDAHAKNRRVVI |

In addition to sequences for OmpA and Asp14 shown in Table 1, and homologs shown in Tables 2-3, other surface proteins that Aph preferentially expresses in human versus tick cells may be used. Table 4 shows examples of proteins that can be included in the "cocktail" of peptides, polypeptides or protein sequences of the composition of the invention. Examples of these include APH_0915, APH_1325 (Msp2), APH_1378, APH_1412, APH_0346, APH_0838, APH_0839, APH_0874, and APH_0906 because all are upregulated 3- to 60-fold during RC-DC transition, DC exit, and/or reinfection and our surface proteomic study indicates that they are surface proteins. The file names for each of the aforementioned proteins are from the *A. phagocytophilum* HZ annotated genome. A similar expression profile is exhibited by APH_1235, which is another late stage gene that is upregulated 70-fold, as taught by Mastronunzio and colleagues, who identified APH_1235 as an *A. phagocytophilum* surface protein. P44 is a 44 kilodalton surface protein and is the bacterium's major surface protein. Synonyms of P44 are Msp2 (major surface protein 2) and Msp2 (P44). All *Anaplasma* species encode P44 proteins and there are huge repertoires of P44 genes in these bacterial species' chromosomes. For instance, the annotated Aph strain HZ genome encode 113 P44 proteins. These exist as complete genes or pseudogenes (incomplete genes). There is one expression site for p44 genes. Basically, different p44 genes get shuffled into the expression site by a process known as gene conversion with the end result being that Aph (and other *Anaplasma* species) can vary the P44 protein on their cell surfaces, a process called antigenic variation. This enables them to perpetually evade the humoral immune response.

TABLE 4

| Anaplamatacaea Surface Proteins Sequence Listing and SEQ ID Numbers | | |
|---|---|---|
| SEQ ID NO: 57 | Full-length APH_0915 | Genbank Accession No: YP_505488 |
| SEQ ID NO: 58 | Full-length APH_1378 | Genbank Accession No: YP_505877 |
| SEQ ID NO: 59 | Full-length APH_1412 | Genbank Accession No: YP_505903 |
| SEQ ID NO: 60 | Full-length APH_0346 | Genbank Accession No: YP_504953 |
| SEQ ID NO: 61 | Full-length APH_0838 | Genbank Accession No: YP_505415 |
| SEQ ID NO: 62 | Full-length APH_0839 | Genbank Accession No: YP_505416 |
| SEQ ID NO: 63 | Full-length APH_0874 | Genbank Accession No: YP_505450 |
| SEQ ID NO: 64 | Full-length APH_0906 | Genbank Accession No: YP_505479 |
| SEQ ID NO: 65 | Full-length APH_1325 (Msp2) | Genbank Accession No: YP_505833 |
| SEQ ID NO: 66 | Full-length APH_1235 | Genbank Accession No: YP_505764 |

In addition to polypeptides sequences from Aph surface proteins, other sequences may be included in the polypeptides of the invention. Such sequences include but are not limited to antigenic peptide sequences such as linker sequences which in and of themselves are antigenic. Examples of recombinant protein tags that may be useful in practicing the invention include but are not limited to glutathione-S-transferease (GST), poly-histidine, maltose binding protein (MBP), FLAG, V5, halo, myc, hemaglutinin (HA), S-tag, calmodulin, tag, streptavidin binding protein (SBP), Softag1™, Softag3™, Xpress tag, isopeptag, Spy Tag, biotin carboxyl carrier protein (BCCP), GFP, Nus-tag, strep-tag, thioredoxin tag, TC tag, and Ty tag. Examples of linker sequences include but are not limited to an amino acid spacer, an amino acid linker, a signal sequence, a stop transfer sequence, a transmembrane domain, and a protein purification ligand. It should also be recognized that a multitude of other such sequences are known to those of skill in the art, and inclusion of other antigenic, linker, or tag sequences is contemplated.

Those of skill in the art will recognize that, while in some embodiments of the invention, the amino acid sequences that are chosen for inclusion in the polypeptides of the invention correspond exactly to the primary amino acid sequence of the original or native sequences of an Asp14 or OmpA protein, this need not always be the case. The amino acid sequence of an epitope that is included in the polypeptides of the invention may be altered somewhat and still be suitable for use in the present invention. For example, certain conservative amino acid substitutions may be made without having a deleterious effect on the ability of the polypeptides to elicit an immune response. Those of skill in the art will recognize the nature of such conservative substitutions, for example, substitution of a positively charged amino acid for another positively charged amino acid (e.g. K for R or vice versa); substitution of a negatively charged amino acid for another negatively charged amino acid (e.g. D for E or vice versa); substitution of a hydrophobic amino acid for another hydrophobic amino acid (e.g. substitution of A, V, L, I, W, etc. for one another); etc. All such substitutions or alterations of the sequences of the polypeptides that are disclosed herein are intended to be encompassed by the present invention, so long as the resulting polypeptides still function to elicit a suitable immune response. In addition, the amino acid sequences that are included in the polypeptides or any chimeric proteins of the invention need not encompass a full length native polypeptide. Those of skill in the art will recognize that truncated versions of amino acid sequences that are known to be or to contain antigenic polypeptides may, for a variety of reasons, be preferable for use in the practice of the invention, so long as the criteria set forth for an epitope is fulfilled by the sequence. Amino acid sequences that are so substituted or otherwise altered may be referred to herein as "based on" or "derived from" the original wild type or native sequence. In general, the Asp14 or OmpA proteins or polypeptide fragments from which the linear epitopes are "derived" or on which the linear epitopes are "based" are the Asp14 or OmpA proteins or peptide fragments as they occur in nature. These natural Asp14/OmpA proteins may alternatively be referred to as native or wild type proteins.

Such changes to the primary sequence may be introduced for any of a variety of reasons, for example, to eliminate or introduce a protease cleavage site, to increase or decrease solubility, to promote or discourage intra- or inter-molecular interactions such as folding, ionic interactions, salt bridges, etc, which might otherwise interfere with the presentation and accessibility of the individual epitopes along the length of a peptide or polypeptide. All such changes are intended to be encompassed by the present invention, so long as the resulting amino acid sequence functions to elicit a protective antibody response in a host to whom it is administered. In general, such substituted sequences will be at least about 50% identical to the corresponding sequence in the native protein, preferably about 60 to 70, or even 70 to 80, or 80 to 90% identical to the wild type sequence, and preferably about 95, 96, 97, 98, 99, or even 100% identical to a native Asp14 or OmpA sequence or peptide fragment. The reference native Asp14 or OmpA sequence or peptide fragment may be from any suitable type of Anaplasmataceae, e.g. from any Anaplasmataceae which is known to infect mammals.

In some embodiments of the invention, individual linear epitopes in a chimeric vaccinogen are separated from one another by intervening sequences that are more or less neutral in character, i.e. they do not in and of themselves elicit an immune response to Anaplasmataceae. Such sequences may or may not be present between the epitopes of a chimera. If present, they may, for example, serve to separate the epitopes and contribute to the steric isolation of the epitopes from each other. Alternatively, such sequences may be simply artifacts of recombinant processing procedures, e.g. cloning procedures. Such sequences are typically known as linker or spacer peptides, many examples of which are known to those of skill in the art. See, for example, Crasto, C. J. and J. A. Feng. 2000.

In addition, other elements may be present in chimeric proteins, for example leader sequences or sequences that "tag" the protein to facilitate purification or detection of the protein, examples of which include but are not limited to tags that facilitate detection or purification (e.g. S-tag, or Flag-tag), other antigenic amino acid sequences such as known T-cell epitope containing sequences and protein stabilizing motifs, etc. In addition, the chimeric proteins may be chemically modified, e.g. by amidation, sulfonylation, lipidation, or other techniques that are known to those of skill in the art.

The invention further provides nucleic acid sequences that encode chimeric proteins of the invention. Such nucleic acids include DNA, RNA, and hybrids thereof, and the like. Further, the invention comprehends vectors which contain or house such coding sequences. Examples of suitable vectors include but are not limited to plasmids, cosmids, viral based vectors, expression vectors, etc. In a preferred embodiment, the vector will be a plasmid expression vector.

The chimeric proteins of the invention may be produced by any suitable method, many of which are known to those of skill in the art. For example, they may be chemically synthesized, or produced using recombinant DNA technology (e.g. in bacterial cells, in cell culture (mammalian, yeast or insect cells), in plants or plant cells, or by cell-free prokaryotic or eukaryotic-based expression systems, by other in vitro systems, etc.). In some embodiments, the polypeptides are produced using chemical synthesis methods.

The present invention also provides compositions for use in eliciting an immune response. The compositions may be utilized as vaccines to prevent or treat anaplasmosis, particularly when manifested in humans as HGA. By eliciting an immune response, we mean that administration of the antigen causes the synthesis of specific antibodies (at a titer as described above) and/or cellular proliferation, as measured, e.g. by $^3$H thymidine incorporation, or by other known techniques. By "vaccine" we mean a linear polypeptide, a mixture of linear polypeptides or a chimeric or fusion polypeptide that elicits an immune response, which results in protection of an organism against challenge with an Anaplasmataceae species bacterium. The protective response either wholly or partially prevents or arrests the development of symptoms related to anaplasmosis or HGA infection (i.e. the symptoms of anaplasmosis), in comparison to a non-vaccinated (e.g. adjunct alone) control organisms, in which disease progression is not prevented. The compositions include one or more isolated and substantially purified polypeptides or chimeric peptides as described herein, and a pharmacologically suitable carrier. The polypeptides or chimeric peptides in the composition may be the same or different, i.e. the composition may be a "cocktail" of different polypeptides or chimeric peptides, or a composition containing only a single type of polypeptide or chimeric peptide. The preparation of such compositions for use as vaccines is well known to those of skill in the art. Typically, such compositions are prepared either as liquid solutions or suspensions, however solid forms such as tablets, pills, powders and the like are also contemplated. Solid forms suitable for solution in, or suspension in, liquids prior to administration may also be prepared. The preparation may also be emulsified. The active ingredients may be mixed with excipients which are pharmaceutically acceptable and compatible with the active ingredients. Suitable excipients are, for example, water, saline, dextrose, glycerol, ethanol and the like, or combinations thereof. In addition, the composition may contain minor amounts of auxiliary substances such as wetting or emulsifying agents, pH buffering agents, and the like. The vaccine preparations of the present invention may further comprise an adjuvant, suitable examples of which include but are not limited to Seppic, Quil A, Alhydrogel, etc. If it is desired to administer an oral form of the composition, various thickeners, flavorings, diluents, emulsifiers, dispersing aids or binders and the like may be added. The composition of the present invention may contain any such additional ingredients so as to provide the composition in a form suitable for administration. The final amount of polypeptides or chimeric peptides in the formulations may vary. However, in general, the amount in the formulations will be from about 0.01-99%, weight/volume.

The methods involve administering a composition comprising recombinant polypeptides or chimeric peptides in a pharmacologically acceptable carrier to a mammal. The mammal may be a human, but this need not always be the case. Because anaplasmosis is a zoonotic disease that causes anaplasmosis in all known mammalian hosts, veterinary applications of this technology are also contemplated. The vaccine preparations of the present invention may be administered by any of the many suitable means which are well known to those of skill in the art, including but not limited to by injection, inhalation, orally, intranasally, by ingestion of a food product containing the polypeptides or chimeric peptides, etc. In some embodiments, the mode of administration is subcutaneous or intramuscular. In addition, the compositions may be administered in conjunction with other treatment modalities such as substances that boost the immune system, various anti-bacterial chemotherapeutic agents, antibiotics, and the like.

The present invention provides methods to elicit an immune response to Anaplasmataceae and/or to vaccinate against Anaplasmataceae infection in mammals. In one embodiment, the mammal is a human. However, those of skill in the art will recognize that other mammals exist for which such vaccinations would also be desirable, e.g. the preparations may also be used for veterinary purposes. Examples include but are not limited to companion "pets" such as dogs, cats, etc.; food source, work and recreational animals such as cattle, horses, oxen, sheep, pigs, goats, and the like; or even wild animals that serve as a reservoir of Anaplasmataceae, particularly wild animals adapted to living in close proximity to urban areas (e.g. mice, deer, rats, raccoons, opossum, coyotes, etc).

The invention also provides a diagnostic and a method for using the diagnostic to identify individuals who have antibodies to the epitopes contained within the polypeptides or chimeric proteins of the invention. A biological sample from an individual (e.g. a human, a deer, or other mammals susceptible to infection by Anaplasmataceae) suspected of having been exposed to Anaplasmataceae, or at risk for being exposed to Anaplasmataceae, is contacted with the peptides, polypeptides, or chimeric proteins of the invention. Using known methodology, the presence or absence of a binding reaction between the polypeptides or chimeric proteins and antibodies in the biological sample is detected. A positive result (i.e. binding occurs, thus antibodies are present) indicates that the individual has been exposed to and/or is infected with Anaplasmataceae. Further, the diagnostic aspects of the invention are not confined to clinical use or home use, but may also be valuable for use in the laboratory as a research tool, e.g. to identify Anaplasmataceae bacteria isolated from ticks, to investigate the geographical distribution of Anaplasmataceae species and strains, etc.

The present invention also encompasses antibodies to the epitopes and/or to the polypeptides or chimeric proteins disclosed herein. Such antibodies may be polyclonal, monoclonal or chimeric, and may be generated in any manner known to those of skill in the art. In a preferred embodiment of the invention, the antibodies are bactericidal, i.e. exposure of Anaplasmataceae bacteria to the antibodies causes death of the bacteria. Such antibodies may be used in a variety of ways, e.g. as detection reagents to diagnose prior exposure to Anaplasmataceae, as a reagent in a kit for the investigation of Anaplasmataceae, to treat Anaplasmataceae infections, etc.

Alternatively, appropriate antigen fragments or antigenic sequences or epitopes may be identified by their ability, when included in polypeptides or chimeric proteins, to elicit suitable antibody production to the epitope in a host to which the polypeptides or chimeric proteins are administered. Those of skill in the art will recognize that definitions of antibody titer may vary. Herein, "titer" is taken to be the inverse dilution of antiserum that will bind one half of the available binding sites on an ELISA well coated with 100 ng of test protein. In general, suitable antibody production is characterized by an antibody titer in the range of from about 100 to about 100,000, and preferably in the range of from about 10,000 to about 10,000,000. Alternatively, and particularly in diagnostic assays, the "titer" should be about three times the background level of binding. For example, to be considered "positive", reactivity in a test should be at least three times greater than reactivity detected in serum from uninfected individuals. Preferably, the antibody response is protective, i.e. prevents or lessens the development of symptoms of disease in a vaccinated host that is later exposed to Anaplasmataceae, compared to an unvaccinated host.

The following Examples are provided to illustrate various embodiments of the invention, however, as described in detail above, aspects of the invention can be practiced in a variety of ways different from those illustrated in the Examples.

EXAMPLES

The following experimental procedures were used in the examples of the invention:

Cell Lines and Cultivation of Uninfected and Aph-Infected HL-60 Cells.

PSGL-1 CHO cells and RF/6A cells were cultivated as described [21,77]. Uninfected HL-60 cells (American Type Culture Collection [ATCC]; Manassas, Va.; ATCC code CCL-240) and HL-60 cells infected with the Aph NCH-1 strain or a transgenic HGE1 strain expressing GFP (a gift from Ulrike Munderloh of the University of Minnesota, Minneapolis, Minn.) were cultivated. Spectinomycin (Sigma-aldrich, St. Louis, Mo.) was added to HL-60 cultures harboring transgenic HGE1 bacteria at a final concentration of 100 μg/ml.

Aph DC Organism Surface Biotinylation and Affinity Purification.

Aph DC organisms from $10^9$ infected (≥90%) HL-60 cells were enriched for by sonication followed by differential centrifugation as described [61]. To purify DC organisms away from the majority of contaminating host and RC organism cellular debris, the sonicate was fractionated using discontinuous Renografin (diatrizoate sodium, Bracco diagnostics, Princeton, N.J.) density gradient centrifugation. Purified DC organisms were resuspended in 1 ml of phosphate-buffered saline (PBS) (pH 8.0) containing 1 mM $MgCl_2$ and 10 mM Sulfo-NHS-SS-Biotin (Pierce; Rockland, Ill.) and incubated for 30 min at room temperature. Free biotin was quenched by washing the sample with 50 mM Tris (pH 8.0), followed by two washes with PBS. Biotinylated bacteria were solubilized in radioimmunoprecipitation assay (RIPA) buffer (25 mM Tris-HCl [pH 7.6], 150 mM NaCl, 1% NP-40, 1% sodium deoxycholate, 0.1% sodium dodecyl sulfate [SDS], 1 mM sodium orthovanadate, 1 mM sodium fluoride, and Complete EDTA-free protease inhibitor set cocktail [Roche, Indianapolis, Ind.]) on ice for 1 h. Every 20 min during the 1-h incubation, the sample was subjected to eight 8-s bursts on ice interspersed with 8-s rest periods using a Misonix 54000 ultrasonic processor (Farmingdale, N.Y.) on an amplitude setting of 30. Insoluble material was removed by spinning at 10,000×g for 10 min at 4° C. To purify biotinylated proteins, the clarified lysate was mixed with High Capacity NeutrAvidin agarose beads (Pierce) by end-over-end rotation overnight at 4° C. The gel slurry was pelleted by centrifugation at 1,000×g for 1 min. After removal of the supernatant, the beads were resuspended in eight ml PBS and parceled into ten 800 μl aliquots, each of which were added to spin columns optimized for affinity purification (Pierce). The columns were washed three times with PBS and centrifuged at 1,000×g to remove any non-biotinylated proteins. The captured biotinylated proteins were eluted from the beads by end-over-end rotation with 150 mM DTT in 0.25% sodium deoxycholate for 2 h at room temperature. The agarose beads were centrifuged at 1,000×g for 2 min and the supernatant containing the biotinylated proteins was saved. The Bradford assay was used to determine the protein concentration of the eluate. The majority of the sample was stored at 4° C. until analysis. To ensure that this procedure had enriched for DC bacterial surface proteins, an aliquot of the affinity-purified sample was resolved by SDS-PAGE alongside an Aph whole-cell lysate, neutravidin beads plus unlabeled DC whole cell lysate, and neutravidin beads alone followed by silver staining.

2D-LC/MS-MS Proteome Analysis.

Unless otherwise stated, all buffers were made with LC/MS grade solvents (Fisher Chemical, Fairlawn, N.J.). Samples were processed for proteomic analysis as described previously with the following methodological details. Following biotinylation enrichment of Aph surface proteins, 300 μg of protein mass in 400 μl of lysis buffer was concentrated and exchanged into 25 μl of ammonium bicarbonate buffer (ABC) (50 mM $NH_4CO_3$/0.05% $C_{24}H_{39}O_4Na$) using a Centriprep YM-10 filter unit (Millipore, Billerica, Mass.). DTT was added to achieve a final concentration of 20 mM, and disulfide bonds were reduced at 90° C. for 30 min. After cooling to room temperature, cysteine alkylation was performed on the sample with freshly prepared iodoacetamide (32 mM) for 30 min at room temperature in the dark. Trypsin Gold (100 ng/μ1; Promega, Madison, Wis.) was added to a final 1:100 enzyme:protein ratio, and the sample was incubated at 37° C. overnight. The digested sample was dried within a speed vacuum and stored dry at −20° C.

The digest sample was reconstituted in 60 μL of 100 mM ammonium formate (pH 10) for multidimensional peptide separation and mass spectrometry analysis on a 2D-nano-Acquity chromatography system online with a Synapt quadrupole/time-of-flight tandem mass spectrometer (Waters) as previously reported. Two-replicate injections were analyzed for the sample. Resulting data were processed using PLGS software, v2.4 (Waters) as described elsewhere. Data were then search against an Aph-specific FASTA database (RefSeq and Uniprot sources; downloaded February 2010) and its reversed-sequences as a decoy database. Search parameters required a minimum precursor ion intensity of 500 counts, two or more peptide sequences per protein and a minimum of seven matching fragment ions. Trypsin selectivity was specified allowing for 1 missed cleavage event and variable methionine oxidation. Using a decoy-database method, a score threshold was calculated at the 5% false-discovery rate. Confidence in the protein identification is also increased for those that were identified against both RefSeq and Uniprot Aph databases.

Analyses of Differential Aph Gene Expression Over the Course of Infection.

Synchronous infections of HL-60 cells with Aph DC organisms were established. Indirect immunofluorescence microscopic examination of aliquots recovered at 24 h confirmed that ≥60% of HL-60 cells contained morulae and that the mean number of morulae per cell was 2.8±0.6. The infection time course proceeded for 36 h at 37° C. in a humidified atmosphere of 5% $CO_2$. At the appropriate time-point, aliquots were removed and processed for RNA isolation and RT-qPCR was performed using gene-specific primers. Relative transcript levels for each target were normalized to the transcript levels of the Aph 16S rRNA gene (Aph_1000) using the $2^{-\Delta\Delta C_T}$ method.

Transmission Feeding of Aph Infected *Ixodes. scapularis* nymphs.

Aph-infected *I. scapularis* nymphs were obtained from a tick colony maintained at Yale University (New Haven, Conn.). To propagate Aph-infected ticks, clean *I. scapularis* larvae were fed on Aph-infected C3H/HeJ mice, and the larvae were allowed to molt to nymphs. Infection was confirmed by testing 10% of each tick batch by PCR of the Aph 16S rRNA gene. Ticks were incubated at 23° C. with 85% relative humidity between feedings. To collect transmission-fed nymphs, groups of 20-25 infected tick nymphs were placed to feed on clean 5-6 week-old C3H/HeJ female mice and removed after 24, 48, or 72 hours of feeding. Salivary glands dissected from 2-3 ticks were pooled into a tube of RLT buffer and frozen at −80° C., prior to RNA extraction with the Qiagen RNEasy Kit (Qiagen, CA). Unfed ticks were dissected and RNA extracted from combined salivary glands and midguts. RT-qPCR was performed as described above.

Recombinant Protein Expression and Purification and Antisera Production.

Aph genes of interest were amplified using gene-specific primers and Platinum Pfx DNA polymerase (Invitrogen). Amplicons were cloned into pENTR/TEV/D-TOPO (Invitrogen) as described [83] to yield pENTR-candidate gene entry plasmids containing the genes of interest. Plasmid inserts were verified and recombination of the candidate gene insert downstream of and in frame with the gene encoding GST was achieved using the pDest-15 vector (Invitrogen). In some cases plasmids encoding GST-OmpA or GST-Asp14 were subjected to PCR mutagenesis using the Stratagene Quick Change kit according to the manufacturer's instructions for the purpose of inserting DNA segments encoding five-amino acid linkers or substituting the alanine codon for a specific OmpA or Asp14 amino acid. Expression and purification of GST-OmpA, GST-Asp14, and GST-Msp5 and generation of murine polyclonal antisera against each protein were performed as described. KLH-conjugated peptides corresponding to OmpA amino acids 23-40, 41-58, or 59-74 or Asp14 amino acids 101-112 or 113-124 were synthesized by and used for raising rabbit polyclonal antiserum against each peptide by New England Peptides (Gardner, Mass.).

Antibodies, Western Blot Analyses, and Spinning Disk Confocal Microscopy.

Antisera generated in this study and previous studies targeted OmpA, Asp14, Msp5, APH_0032 [61], APH_1387 [83], Msp2 (P44), and Asp55 and Asp62. The latter two antibodies were gifts from Yasuko Rikihisa of The Ohio State University (Columbus, Ohio). Anti-Msp2 (P44) mAb 20B4 [84,85] was a gift from J. Stephen Dumler of The Johns Hopkins University (Baltimore, Md.). Western blot analyses were performed. Aph infected HL-60 cells were processed and analyzed via indirect immunofluorescence using spinning disk confocal microscopy.

Surface Trypsin Digestion of Intact Aph DC Organisms.

Intact DC bacteria were incubated at a 10:1 ratio of total protein to trypsin (Thermo Scientific, Waltham, Mass.) in 1×PBS or vehicle alone at 37° C. After 30 min, phenylmethanesulfonyl fluoride (Sigma) was added to a final concentration of 2 mM. Bacteria were pelleted at 5,000 g for 10 min, after which pellets were resuspended in urea lysis buffer and processed. Lysates of trypsin- and vehicle-treated Aph organisms were fractionated by SDS-PAGE, Western-blotted, and screened with antibodies targeting OmpA, Asp14, Asp55 [33], Msp5, Msp2 (P44), and APH_0032.

Flow Cytometry.

$1\times10^7$ HL-60 cells infected with either transgenic HGE1 organisms expressing GFP or wild-type Aph bacteria were mechanically lysed followed by differential centrifugation to pellet host cellular debris. GFP-positive Aph organisms and remaining host cellular debris were pelleted, followed by resuspension in PBS containing equivalent amounts of a 1:25 dilution of preimmune mouse serum, mouse anti-Asp14 or anti-OmpA, or secondary antibody alone. Antibody incubations and wash steps were performed. For FACS analyses, samples were analyzed on a FACSCanto II Flow Cytometer (Becton Dickinson, Franklin Lakes, N.J.). $1\times10^8$ events, which corresponded to individual Aph organisms and host cellular debris, were collected in the VCU Flow Cytometry and Imaging Shared Resource Facility. Post data-acquisition analyses were performed using the FCS Express 4 Flow Cytometry software package (De Novo Software, Los Angeles, Calif.).

In Silico Analyses.

The MEMSAT-SVM algorithm (bioinf.cs.ucl.ac.uk/psipred) was used to predict the membrane topology of Aph OmpA. Predicted signal sequences for *Anaplasma* spp., *Ehrlichia* spp., and *O. tsutsugamushi* OmpA proteins were determined using TMPred (www.ch.embnet.org/software/TMPRED_form). Alignments of OmpA sequences (minus the predicted signal sequences) were generated using CLUSTAL W. The tertiary structure for Aph OmpA was predicted using the PHYRE$^2$ (Protein Homology/analogy Recognition Engine, version 2.0) server (see the website at sbg.bio.ic.ac.uk/phyre2). To assess how OmpA potentially interacts with sLe$^x$, the OmpA tertiary structure predicted by PHYRE$^2$ was docked with the crystal structure for sLe$^x$ using the autodock vina algorithm.

Assay for Inhibition of Aph Binding and Infection.

For antibody blocking studies, infection assays were performed as described, except that host cell-free Aph organisms were incubated with heat-killed mouse polyclonal antiserum targeting GST, GST-Asp14, or GST-OmpA (10-200 ug/ml) or rabbit polyclonal anti-OmpA (targeting OmpA aa23-40, aa43-58, or aa59-74) and/or anti-Asp14 peptide serum (targeting Asp14 aa98-112 or aa 113-124) for 30 min, after which the bacteria were added to HL-60 cells in the continued presence of antiserum for 1 h. Unbound bacteria were removed and aliquots of host cells were examined for bound Aph organisms using indirect immunofluorescence microscopy. The remainders of the samples were incubated for 48 h, after which host cells were examined for the presence of morulae using indirect immunofluorescence microscopy. For recombinant protein blocking studies, RF/6A or HL-60 cells were incubated with 4 μM GST; GST-Asp14; GST-OmpAor GST APH_1387 at 37° C. for 1 h. Host cells were washed with PBS to remove unbound proteins, fixed with paraformaldehyde for 1 h, and permeabilzed with ice-cold methanol for 30 min. Protein binding to host cells was assessed by indirect immunofluorescence microscopy using rabbit anti-GST antibody (Invitrogen). For blocking studies, host cells were incubated with recombinant proteins for 1 h after which Aph organisms were added for an additional 24 h. Unbound bacteria were removed and the samples were incubated for 48 h followed by immunofluorescence microscopy analysis for the presence of morulae.

Statistical Analyses.

The Student's t test (paired) performed using the Prism 4.0 software package (Graphpad; San Diego, Calif.) was used to assess statistical significance. Statistical significance was set at $p<0.05$.

Example 1. Neutravidin Affinity Purification of Biotinylated Aph DC Surface Proteins and Two-Dimensional-Liquid Chromatography Tandem Mass Spectrometry (2D-LC/MS-MS) Proteome Analysis Identifies Novel Outer Membrane Protein Candidates DC bacteria were purified to remove the majority of contaminating host cellular debris. DC surface proteins labeled by Sulfo-NHS-SS-Biotin were recovered by neutravidin affinity chromatography (data not shown). Aliquots of input host cell-free DC lysate, affinity-captured DC surface proteins, neutravidin beads plus unlabeled DC whole cell lysate (lane 3), and neutravidin beads alone were resolved by SDS-PAGE followed by silver staining.

Because the Aph DC is the adherent and infectious form and the complement of DC surface proteins is unknown, we set out to identify DC surface proteins. Aph infected HL-60 cells were sonicated to liberate the bacteria from host cells and destroy fragile RC organisms. Electron microscopic examination of sonicated samples confirmed the presence of DC, but not RC bacteria, along with host cellular debris (data not shown). DC organisms were surface-labeled and biotinylated proteins were captured by chromatography. Aliquots of affinity-captured DC proteins, input host cell-free DC lysate, neutravidin beads plus unlabeled DC whole cell lysate, and neutravidin beads alone were resolved by SDS-PAGE followed by silver staining (data not shown). Comparison of the banding patterns of the input lysate and eluate revealed enrichment for many proteins. With the exception of proteins of 44 kDa and 70 kDa, both of which were recovered in low abundances, non-biotinylated DC whole cell lysate proteins did not bind to neutravidin beads.

Eluted proteins were subjected to 2D-LC/MS-MS proteomic analysis. Resulting data were searched against 2 Aph-specific FASTA databases (RefSeq and Uniprot sources) using Protein Lynx Global Surveyor (PLGS) software. Table 5 summarizes a total of 56 identified Aph proteins, 47 of which were identified in both the RefSeq and UnitProt sources.

TABLE 5

Aph DC proteins recovered post-surface labeling and affinity chromatography analyzed by 2D-nanoLC/tandem MS protein analysis
TABLE 5. *A. phagocytophilum* DC proteins recovered post-surface labeling and affinity chromatography analyzed by 2D-nanoLC/tandem MS protein analysis

| | | | | RefSeq[a] | | | | UniProt[b] | | | |
|---|---|---|---|---|---|---|---|---|---|---|---|
| Locus | JCVI Description | mW[c] (Da) | pI[d] | Score | Peptides | Coverage (%) | Amount (fmol)[e] | Score | Peptides | Coverage (%) | Amount (fmol) |
| **APH_1221**[f] | **P44 18ES outer membrane protein expression locus with P44-18** | 45,799 | 5.6 | 20,608.4 | 131 | 78.0 | 269.0 | 20,363.3 | 133 | 78.0 | 222.1 |
| APH_1287 | P44 32 outer membrane protein | 44,350 | 5.4 | 19,848.5 | 137 | 73.9 | 343.3 | 19,451.2 | 137 | 75.1 | 375.9 |
| **APH_1229** | **P44 2b outer membrane protein** | 44,884 | 5.2 | 18,321.9 | 138 | 81.4 | 29.1 | 17,898.4 | 135 | 76.5 | 31.7 |
| APH_1169 | P44 19 outer membrane protein | 33,033 | 5.3 | 18,185.8 | 62 | 82.3 | 524.8 | 17,902.6 | 65 | 82.3 | 633.6 |
| APH_1269 | P44 16 outer membrane protein | 45,261 | 5.6 | 16,839.7 | 114 | 69.0 | 314.4 | 16,779.1 | 116 | 69.0 | 550.3 |
| APH_1275 | P44 16b outer membrane protein | 45,194 | 5.9 | 16,695.3 | 122 | 78.0 | 44.4 | 16,427.1 | 122 | 78.0 | 37.5 |
| APH_1215 | P44 14 outer membrane protein | 46,133 | 5.4 | 13,580.3 | 129 | 77.1 | 788.0 | 13,490.5 | 123 | 76.7 | 664.6 |
| APH_0172 | P44 outer membrane protein C terminal fragment | 7,236 | 4.4 | 11,994.3 | 18 | 94.0 | 0[g] | 11,807.8 | 18 | 94.0 | 0 |
| APH_1235 | Hypothetical protein | 14,762 | 5.3 | 4,190.9 | 33 | 91.8 | 189.4 | 4,998.2 | 30 | 97.0 | 189.4 |
| **APH_0240** | **Chaperonin GroEL** | 58,263 | 5.0 | 1,436.7 | 69 | 68.7 | 76.9 | 1,403.2 | 64 | 71.6 | 76.9 |
| APH_0494 | F0F1 ATP synthase subunit beta | 51,478 | 4.8 | 641.4 | 32 | 58.9 | 40.8 | 628.2 | 30 | 70.1 | 40.8 |
| **APH_0405** | **Asp62 outer membrane protein** | 57,538 | 9.5 | 489.5 | 27 | 45.5 | 84.9 | 471.9 | 21 | 38.6 | 106.4 |
| APH_1087 | Putative competence lipoprotein ComL | 26,084 | 4.8 | 458.2 | 10 | 36.9 | 32.9 | 519.9 | 10 | 36.9 | 32.9 |
| APH_1032 | Elongation factor Tu | 42,831 | 5.1 | 415.5 | 19 | 44.8 | 0.0 | 398.1 | 19 | 35.1 | 51.1 |
| APH_1190 | Putative ATP synthase F0 B subunit | 18,837 | 5.9 | 415.5 | 2 | 14.4 | 31.7 | 458.5 | 10 | 47.9 | 31.7 |
| **APH_0404** | **Asp55 outer membrane protein** | 63,644 | 8.9 | 413.1 | 21 | 26.8 | 49.3 | 413.9 | 22 | 25.8 | 49.3 |
| APH_0397 | 30S ribosomal protein S2 | 32,118 | 9.2 | 406.4 | 12 | 32.8 | 66.8 | 392.5 | 12 | 36.1 | 66.8 |
| **APH_0036** | **Co chaperone GrpE** | 22,646 | 5.8 | 394.7 | 4 | 33.2 | 0.0 | 372.7 | 4 | 33.2 | 0 |
| **APH_1404** | **Type IV secretion system protein VirB10** | 46,871 | 4.7 | 388.9 | 8 | 22.8 | 34.5 | 379.4 | 7 | 21.7 | 34.5 |
| **APH_0346** | **Chaperone protein DnaK** | 69,676 | 4.9 | 381.2 | 25 | 34.4 | 177.7 | 380.1 | 24 | 36.4 | 177.7 |
| APH_0248 | Hypothetical protein (Asp14) | 13,824 | 4.9 | 359.0 | 10 | 58.1 | 0 | | | | |
| APH_1049 | Major surface protein 5 | 23,341 | 4.7 | 353.7 | 4 | 22.5 | 170.6 | 339.9 | 3 | 22.5 | 170.6 |
| APH_1334 | F0F1 ATP synthase subunit alpha | 54,068 | 5.3 | 312.1 | 30 | 34.8 | 180.0 | 270.5 | 23 | 28.5 | 0 |
| APH_0051 | Iron binding protein | 37,317 | 5.2 | 252.9 | 4 | 14.6 | 0 | 318.8 | 5 | 17.9 | 109.1 |
| APH_0853 | Hypothetical protein | 10,833 | 9.3 | 249.9 | 4 | 62.9 | 0 | 162.7 | 1 | 15.5 | 0 |
| APH_0625 | Immunogenic protein; membrane transporter | 34,653 | 5.9 | 229.0 | 6 | 28.6 | 0 | 207.9 | 5 | 28.6 | 0 |
| APH_1050 | Putative phosphate ABC transporter periplasmic phosphate binding protein | 37,567 | 5.6 | 221.0 | 3 | 16.5 | 0 | 192.1 | 1 | 2.7 | 0 |
| APH_1246 | Glutamine synthetase type I | 52,383 | 6.0 | 216.0 | 9 | 10.2 | 0 | 228.0 | 10 | 10.2 | 0 |
| APH_1232 | Citrate synthase I | 45,591 | 5.8 | 213.8 | 5 | 19.7 | 0 | 151.0 | 2 | 3.6 | 0 |
| APH_0600 | Thiamine biosynthesis protein ThiC | 61,522 | 6.0 | 203.3 | 4 | 11.0 | 0 | 206.0 | 4 | 13.5 | 0 |
| APH_0059 | Phenylalanyl tRNA synthetase alpha subunit | 39,277 | 6.5 | 197.0 | 7 | 14.0 | 0 | 180.0 | 8 | 11.4 | 0 |
| APH_0555 | Cysteinyl tRNA synthetase | 51,774 | 5.8 | 192.8 | 5 | 18.6 | 0 | 197.2 | 4 | 16.0 | 0 |
| APH_0794 | Hypothetical protein | 27,119 | 7.1 | 183.9 | 2 | 8.4 | 0 | 164.8 | 1 | 4.2 | 0 |
| APH_0740 | AnkA | 131,081 | 6.1 | 182.8 | 11 | 7.2 | 0 | 189.2 | 13 | 8.2 | 0 |
| APH_1258 | Fructose bisphosphate aldolase | 32,685 | 6.7 | 182.0 | 5 | 9.2 | 0 | 193.7 | 4 | 9.2 | 0 |
| APH_1025 | 50S ribosomal protein L7 L12 | 14,122 | 4.8 | 181.5 | 2 | 23.9 | 0 | | | | |
| APH_1292 | Cell division protein FtsZ | 41,975 | 5.0 | 181.3 | 3 | 13.3 | 0 | 205.0 | 3 | 10.5 | 0 |
| **APH_1210** | **OMP85 family outer membrane protein** | 85,652 | 8.5 | 173.9 | 7 | 8.3 | 0 | 165.5 | 6 | 5.7 | 0 |
| APH_0283 | 50S ribosomal protein L2 | 29,772 | 11.5 | 169.5 | 3 | 8.3 | 0 | 154.1 | 2 | 6.2 | 0 |
| APH_0893 | Heat shock protein 90 | 71,123 | 4.9 | 167.9 | 6 | 12.7 | 0 | 173.7 | 9 | 17.0 | 0 |
| APH_0111 | Uridylate kinase | 26,347 | 6.9 | 164.4 | 2 | 13.1 | 0 | 176.4 | 3 | 18.0 | 0 |
| **APH_0608** | **PpiC parvulin rotamase family protein** | 67,363 | 4.9 | 161.4 | 10 | 13.1 | 0 | 144.2 | 8 | 9.0 | 0 |
| **APH_1359** | **Major outer membrane protein OMP-1A** | 31,617 | 9.0 | 157.8 | 2 | 5.5 | 0 | 142.4 | 2 | 5.5 | 0 |

TABLE 5-continued

Aph DC proteins recovered post-surface labeling and affinity chromatography analyzed by 2D-nanoLC/tandem MS protein analysis
TABLE 5. *A. phagocytophilum* DC proteins recovered post-surface labeling and affinity chromatography analyzed by 2D-nanoLC/tandem MS protein analysis

| | | | | RefSeq[a] | | | | UniProt[b] | | | |
|---|---|---|---|---|---|---|---|---|---|---|---|
| Locus | JCVI Description | mW[c] (Da) | pI[d] | Score | Peptides | Coverage (%) | Amount (fmol)[e] | Score | Peptides | Coverage (%) | Amount (fmol) |
| APH_1084 | Cytochrome c oxidase subunit II | 29,873 | 6.1 | 155.0 | 3 | 13.0 | 0 | | | | |
| APH_0422 | Acetylglutamate kinase | 35,726 | 4.6 | 151.9 | 2 | 7.0 | 0 | | | | |
| APH_0971 | Putative trigger factor | 49,358 | 4.8 | 140.8 | 3 | 13.0 | 0 | 138.3 | 2 | 10.0 | 0 |
| APH_0038 | CTP synthetase | 59,416 | 5.5 | 139.6 | 2 | 5.9 | 0 | 136.9 | 2 | 5.9 | 0 |
| APH_1355 | P44 79 outer membrane protein | 50,321 | 8.7 | 139.0 | 2 | 3.9 | 0 | 147.7 | 2 | 4.6 | 0 |
| APH_0669 | Bifunctional proline dehydrogenase pyrroline 5 carboxylate dehydrogenase | 114,508 | 5.1 | 139.0 | 4 | 6.9 | 0 | 159.1 | 5 | 7.6 | 0 |
| APH_0450 | ATP dependent Clp protease ATP binding subunit ClpA | 86,715 | 6.2 | 138.0 | 2 | 1.6 | 0 | | | | |
| APH_0231 | Leucyl aminopeptidase | 54,611 | 5.5 | 128.8 | 3 | 11.4 | 0 | | | | |
| APH_0874 | Hypothetical protein | 115,420 | 6.6 | 123.2 | 5 | 2.9 | 0 | | | | |
| APH_1017 | Outer membrane protein Msp2 family | 46,971 | 8.4 | | | | | 131.9 | 2 | 3.6 | 0 |
| APH_1339 | Conserved domain protein | 47,356 | 7.3 | | | | | 128.6 | 2 | 5.1 | 0 |
| APH_0168 | Heme exporter protein CcmC | 26,310 | 9.5 | | | | | 126.7 | 4 | 6.9 | 0 |
| APH_0502 | tRNA pseudouridine synthase A | 28,012 | 8.8 | | | | | 131.9 | 2 | 3.6 | 0 |

[a]Refseq, *A. phagocytophilum*, Downloaded February 2010
[b]UniProt, *A. phagocytaphilum*, Downloaded February 2010
[c]mW, molecular weight in Daltons
[d]pI, isoelectric point
[e]fmol, femtomoles
[f]Proteins that have been previously confirmed to be on the *A. phagocytophilum* surface and/or were recovered by surface biotinylation and affinity chromatography in the study by Ge and colleagues are denoted by bold text.
[g]Peptides that are considered in-source fragments are given a 0 fmol value as their quantification is confounded by signal lost within the mass spectrometer.

All proteins for which at least two peptides were identified from either RefSeq or UnitProt and scored above a 5% false-discovery cutoff are listed. Three protein identifications from each search result are likely false-positives, and are most probably among those found on one search result. Nine proteins had previously been delineated as being surface-localized, thereby validating the efficacy of our approach. Ten paralogs of the major surface protein 2 [Msp2 (P44)] family were identified, eight of which yielded the highest PLGS scores.

Example 2. Selection of Aph OMP Candidates for Further Study. FIG. 1A Illustrates the Experimental Timeline Relative to the the Infection Cycle and Stages of Aph Organisms During Infection of a Host DC organisms were used to synchronously infect HL-60 cells and the infection proceeded for 36 h, a time period that allows for the bacteria to complete their biphasic developmental cycle and reinitiate infection. Total RNA was isolated from the DC inoculum and from infected host cells at several postinfection time points. RT-qPCR was performed using gene-specific primers. Relative transcript levels for each target were normalized to Aph 16S rRNA gene transcript levels using the $2^{-\Delta\Delta c_T}$ method. To determine the relative transcription of OMP candidate genes between RC and DC organisms, normalized transcript levels of each gene per time point (shown in FIG. 1B-D) were calculated as the fold-change in expression relative to expression at 16 h (encircled in the experimental timeline in FIG. 1A), a time point at which the Aph population consists exclusively of RC organisms. (FIG. 1A) Diagram of the experimental design highlighting the time points at which RNA was isolated, the Aph biphasic developmental and infection stages, and the expression categories into which each gene of interest was classified based on its expression profile. (FIGS. 1B-D) RT-qPCR results for each OMP candidate-encoding gene of interest are grouped as (1B) early stage, (1C) mid stage, and (1D) late stage depending on when during the course of infection they are most highly expressed. (FIG. 1E) RT-qPCR results for control genes. The data in FIGS. 1B-E are the means and standard deviations of results for triplicate samples and are representative of two independent experiments that yielded similar results.

Several proteins were selected for differential gene expression analysis over the course of Aph infection. Asp14, APH_0625, and APH_0874 were chosen because they were hitherto hypothetical proteins. For the remainder of this paper, we will refer to "hypothetical" proteins for which we have demonstrated expression as "uncharacterized" proteins. APH_1049 (Msp5), APH_1210 (Omp85), and APH_1359 (Omp-1A) were selected because, even though they are confirmed *Anaplasma* spp. proteins, their differential gene expression patterns have yet to be studied. APH_0240 (chaperonin GroEL), APH_0346 (DnaK), and APH_1032 (elongation factor Tu) were chosen because, even though these proteins play housekeeping roles, they have also been identified as surface proteins of Aph and other bacterial species and/or have been linked to bacterial adhesion.

A limitation of the surface biotinylation-affinity proteomics method is that it will not identify surface proteins that are inaccessible to the cross-linker, either due to a lack of free amine groups for cross-linking or due to excessive distance from the bacterial surface to which it extends relative to the length of the cross-linker. Also, detergents may not fully extract integral membrane proteins or protein complexes. Lastly, a surface protein that is in low abundance may not be in sufficient quantity to be detected even if biotinylated. We rationalized that Aph genes upregulated during colonization of mammalian versus tick cells are important for infection of mammalian cells. Therefore, as a complementary approach, we selected 9 candidate genes that are known to be preferentially expressed during infection of HL-60 cells and endothelial cells versus infection of ISE6 (immortalized *I. scapularis* embryonic) cells and are predicted by the CELLO subcellular prediction server to localize to the Aph outer membrane. These candidates, which were not detected by our or a previous surface proteomics study, are OmpA (homologous to peptidoglycan-associated lipoprotein [Pal]; conserved among most Gram-negative bacteria), APH_1220 (Omp-1N), APH_1325 (Msp2), APH_0838, APH_0839, APH_0906, APH_0915, APH_1378, and APH_1412. We also selected aph 0441 and aph_1170, because they encode previously detected, but uncharacterized Aph surface proteins. The SignalP 3.0 server predicts 9 of the 20 candidates—OmpA, Omp-la, Omp-1N, Omp85, Msp2, Msp5, APH_0441, APH_0915, and APH_1378—to carry N-terminal signal peptide sequences. The TMPred algorithm (see the website at ch.embnet.org/software/TMPRED_form-.html) predicts that all candidates except for Asp14 and APH_1412 carry one or more transmembrane domains.

Example 3. Differential Transcription Profiling of omp Candidate Genes Throughout the Aph Infection Cycle To gain insight into the transcription of the 20 genes of interest during the Aph infection cycle, we synchronously infected HL-60 cells with DC organisms and allowed the infection to proceed in order for the bacteria to complete their biphasic developmental cycle and initiate a second round of infection. We isolated total RNA from DC organisms used as the inoculum and from bacteria recovered at several post-infection time points. RT-qPCR was performed on total RNA using gene-specific primers. Relative transcript levels for each target were normalized to Aph 16S rRNA gene (aph_1000) transcript levels using the $2^{-\Delta\Delta C_T}$ method. To facilitate identification of genes that are upregulated in the infectious DC form compared to the non-infectious RC form, normalized transcript levels for each gene per time point were calculated as the fold-change in expression relative to expression at 16 h, a time point at which the Aph population consists exclusively of RC organisms.

Figure 1B:
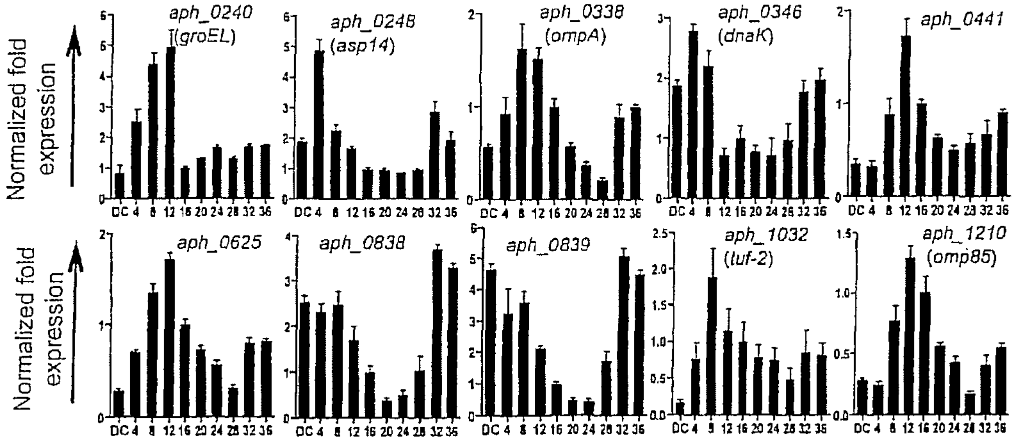
FIG. 1C-E. Differential transcription profiling of OMP candidate genes throughout the Aph infection cycle.
Figure 1C:
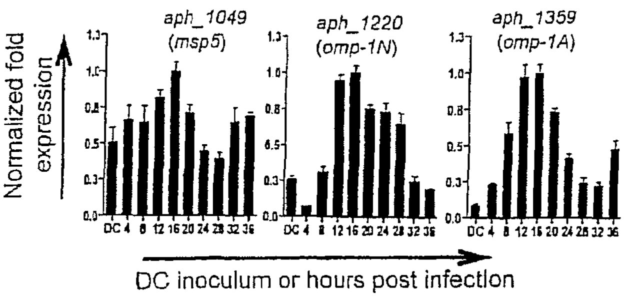
Figure 1D:
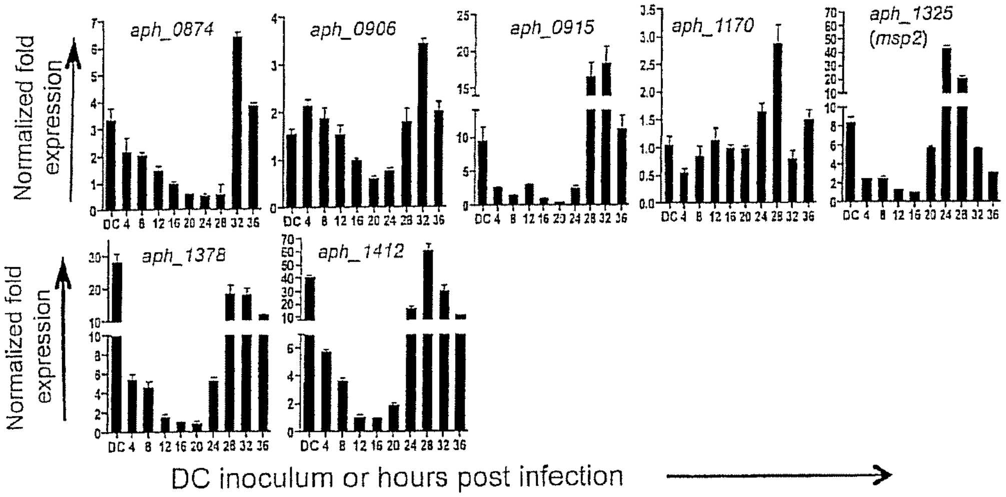
Figure 1E:
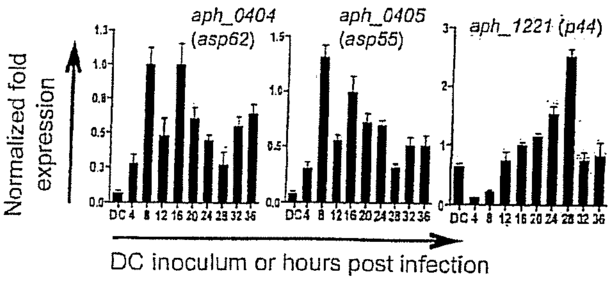

Genes of interest were classified as early (0-12 h), mid (12-24 h), or late stage (24-36 h) (FIG. 1A). The early stage correlates with DC adhesion and invasion, DC to RC differentiation, and initiation of RC replication. Early stage gene transcription increased at 4 h and peaked at 8 h or 12 h, except for asp14 and aph_0346, both of which peaked at 4 h (FIG. 1B). Expression levels of all early stage genes began to increase again between 28 and 36 h, which correspond to the period during which Aph RC organisms differentiate to DC organisms and initiate the second round of infection. Mid stage gene expression, which coincides with a period of extensive Aph replication, peaked at 16 h (FIG. 1C). Late stage genes were upregulated between 24 and 36 h (FIG. 1D), a period that correlates with the conversion of RC to DC organisms, DC exit, and initiation of the second round of infection. All target mRNAs were detected in host cell-free DC organisms (FIG. 1). Transcript levels of asp14, aph_0346, aph_0838, aph_0839, aph_0874, aph_0915, aph_1378, aph_1412, and msp2 were more abundant in DC bacteria used as the inoculum than in RC bacteria at 16 h. Because msp2 (P44), asp62, and asp55 encode confirmed Aph surface proteins and because the latter two constitute an operon, these genes were analyzed as controls. Coincident with the kinetics of the infection cycle, msp2 (p44) transcription steadily increased from 4 to 28 h, after which it pronouncedly declined by 32 h. The transcriptional profiles of asp55 and asp62 were highly similar, which reinforces the accuracy of the expression data obtained for all genes.

Figure 2A:
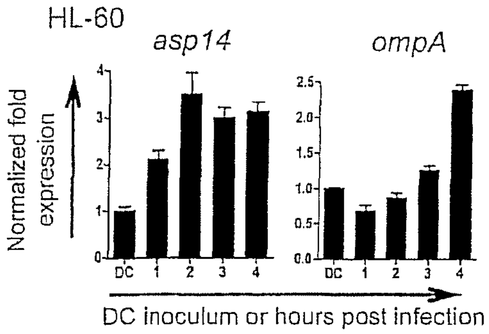
FIG. 2A-D. Differential expression analyses of ompA and asp14 during Aph invasion of HL-60 and RF/6A cells, during Aph binding to PSGL-1 CHO cells, and during transmission feeding of Aph infected *I. scapularis* ticks.
Figure 2B:
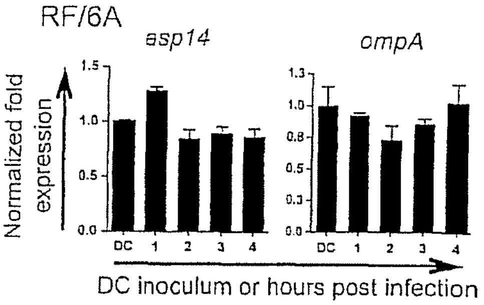
Figure 2C:
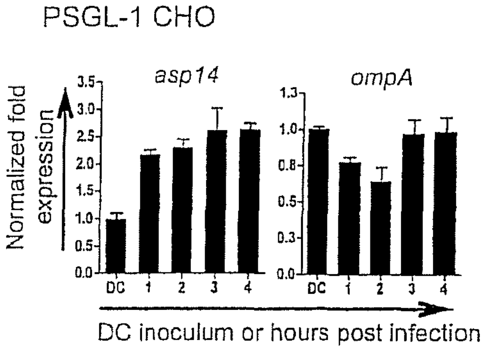

Example 4. Aph Transcriptionally Upregulates ompA and Asp14 During Binding and Invasion of Myeloid but not Endothelial Cells It takes up to four hours for the majority of bound Aph organisms to enter and reside within nascent host cell-derived vacuoles. Thus, genes that are upregulated between 0 and 4 h and in the initial hours following bacterial entry conceivably encode products that are important for invasion and/or establishing infection. Of all genes examined, asp1-1 is the most abundantly expressed at 4 h (FIGS. 1B-E), and asp14 and ompA exhibit the most abundant non-DC to RC-normalized transcript levels (data not shown). Accordingly, we more closely examined the expression profiles of ompA and asp14. Differential expression analyses of ompA and asp14 during Aph invasion of HL-60 and RF/6A cells, during Aph binding to PSGL-1 CHO cells, and during transmission feeding of Aph infected *I. scapularis* ticks is shown in FIG. 2A-C. Aph organisms were incubated with HL-60 (2A), RF/6A (2B), and PSGL-1 CHO cells (2C) for 4 h, a period that is required for bacterial adherence and for >90% of bound bacteria to invade host cells. Aph cannot invade PSGL-1 CHO cells. Total RNA was isolated from the DC inoculum and from host cells at 1, 2, 3, and 4 h post-bacterial addition. (2D) Aph infected *I. scapularis* nymphs were allowed to feed on mice for 72 h. Total RNA was isolated from the salivary glands of uninfected and transmission fed ticks that had been removed at 24, 48, and 72 h post-attachment. Total RNA was isolated from combined salivary glands and midguts from unfed ticks. (2A-2D) RT-qPCR was performed using gene-specific primers. Relative transcript levels for asp14 and ompA were normalized to Aph 16S rRNA gene transcript levels. The normalized values in FIGS. 2A-C are presented relative to asp14 or ompA transcript levels of the DC inoculum. Data are the means and standard deviations of results for triplicate samples and are representative of two independent experiments that yielded similar results.

Aph DC bacteria were added to HL-60 and RF/6A cells, after which RT-qPCR was performed on total RNA isolated at 1, 2, 3, and 4 h. RNA isolated from the DC bacterial inoculum served as a reference control. asp14 was upregulated at all time points during adhesion and invasion of HL-60 cells and exhibited a maximal increase at 2 h, whereas ompA demonstrated a maximal increase at 4 h (FIG. 2A). Neither ompA nor asp14 was upregulated during binding and invasion of endothelial cells (FIG. 2B).

Example 5. Aph Engagement of PSGL-1 Promotes Upregulation of Asp14, but not ompA We next examined whether Aph binding to PSGL-1 upregulates either asp14 or ompA. Chinese hamster ovary cells transfected to express PSGL-1 (PSGL-1 CHO cells) are ideal models for studying Aph-PSGL-1 interactions because they support Aph binding, while untransfected CHO cells that lack PSGL-1 expression do not. Thus, Aph binding to PSGL-1 CHO cells occurs exclusively through bacterial engagement of PSGL-1. DC bacterial binding to PSGL-1 CHO cells upregulated asp14, but not ompA (FIG. 2C).

Figure 2D:
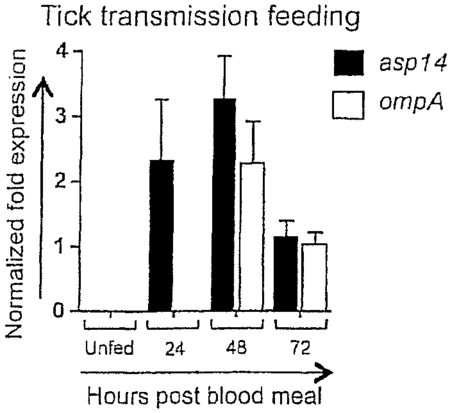

Example 6. Aph Upregulates ompA and Asp14 During *I. scapularis* Transmission Feeding Aph genes that are induced during the bloodmeal of infected *I. scapularis* ticks are presumably important for establishing infection in mammals. We examined ompA and asp14 expression in Aph infected *I. scapularis* nymphs during transmission feeding on naïve mice. Transcripts for neither ompA nor asp14 were detected in unfed Aph infected nymphs (FIG. 2D). Both asp14 and ompA were induced during transmission feeding, being first detected at 24 h and 48 h, respectively.

Figures 3A, 3B, 3C, 3D, 3E, 3F, 3G:
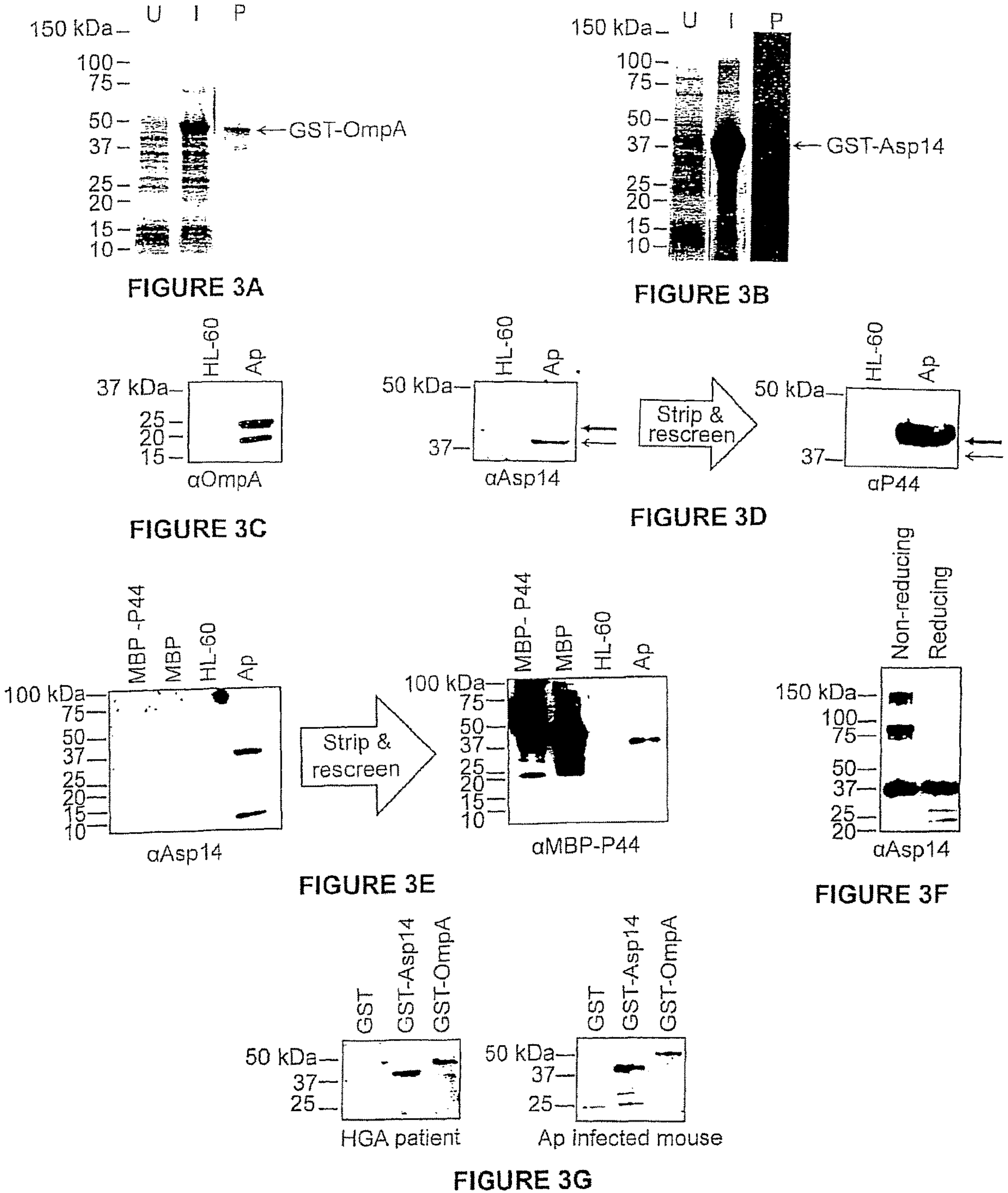
FIG. 3A-G. Aph expresses OmpA and Asp14 during infection of HL-60 cells and during murine and human infection.

Example 7. Aph Expresses OmpA and Asp14 During Infection of HL-60 Cells and During Murine and Human Infection As illustrated in FIGS. 3A and B, whole cell lysates of *E. coli* (U), *E. coli* induced (I) to express GST-OmpA (FIG. 3A) or GST-Asp14 (FIG. 3B), and GST-OmpA (3A) or GST-Asp14 (3B) purified (P) by glutathione sepharose affinity chromatography were separated by SDS-PAGE and stained with Coomassie blue. (FIGS. 3C and D) Western blot analyses in which mouse anti-OmpA (αOmpA; raised against GST-OmpA) and αAsp14 (raised against GST-Asp14) were used to screen whole cell lysates of uninfected HL-60 cells and Ap organisms. The blot in FIG. 3D was stripped and rescreened with anti-Msp2 (P44) (αP44). The thin and thick arrows denote Asp14 and Msp2 (P44), respectively. (FIG. 3E) Western blotted MBP-P44, MBP, and whole cell lysates of uninfected HL-60 cells and Aph organisms were screened with αAsp14. The blot was stripped and rescreened with anti-MBP-P44. (FIG. 3F) GST-Asp14 was resolved by SDS-PAGE under non-reducing and reducing conditions, Western-blotted, and screened with αAsp14. (FIG. 3G) Western-blotted GST-OmpA, GST-Asp14, and GST were screened with sera from an HGA patient and an experimentally infected mouse.

The coding regions of ompA (excluding the signal sequence; 19.9 kDa) and asp14 (13.8 kDa) were cloned and expressed in *E. coli* as N-terminal glutathione-S-transferase (GST)-tagged fusion proteins designated as GST-OmpA and GST-Asp14, respectively (FIGS. 3A and B). After glutathione-Sepharose affinity chromatography, purified GST-OmpA and GST-Asp14 appeared as 46.0- and 39.8-kDa bands, respectively, upon SDS-PAGE. Each fusion protein was used to immunize mice. Polyclonal anti-OmpA antisera recognized proteins of 22.1 kDa and 19.9 kDa, which correspond to OmpA preprotein and mature OmpA, respectively, in an Aph lysate but not an uninfected HL-60 cell lysate (FIG. 3C). In addition to the anticipated 13.8 kDa band, anti-Asp14 detected a band of approximately 42 kDa in a lysate of Aph, but not uninfected HL-60 cells (FIG. 3E). Anti-Asp14 occasionally detected another band of approximately 28 kDa on blots of Aph lysates (data not shown). Even though the 42-kDa band is close in size to that anticipated for Msp2 (P44), anti-Asp14 failed to recognize Aph-derived maltose binding protein (MBP)-tagged Msp2 (P44) (FIGS. 3D and E). An amino acid sequence alignment of Asp14 with Msp2 (P44)-23, the most abundantly expressed Msp2 (P44) paralog of the Aph NCH-1 strain [56,57], revealed no considerable stretches of homology (data not shown). GST-Asp14 multimerizes when fractionated by non-denaturing SDS-PAGE (FIG. 3F). Thus, the 28- and 42-kDa bands in the Aph lysate recognized by anti-Asp14 are presumably multimeric complexes that consist exclusively of or contain Asp14. HGA patient serum and Aph infected mouse serum recognize GST-OmpA and GST-Asp14 (FIG. 3G), signifying that Aph expresses OmpA and Asp14 during human and murine infection.

Example 8. OmpA is Differentially Expressed by Aph During Infection of Mammalian Versus Tick Cells, while Asp14 is Expressed During Infection of Both Mammalian and Tick Cells Because Aph infects myeloid cells, endothelial cells, and *I. scapularis* cells in vivo and in vitro, we examined Asp14 and OmpA expression during infection of HL-60 cells, RF/6A cells, and ISE6 cells, (data not shown). Aph infected HL-60, RF/6A, and ISE6 cells were fixed and viewed by confocal microscopy to determine immunoreactivity with antibodies against Msp2 (P44) (major surface protein; used to identify bacteria), OmpA, or Asp62 (confirmed surface protein). Both OmpA and Asp62 staining yield comparable ring-like bacterial surface staining patterns. Results described are the means and standard deviations of results of at least two separate experiments. At least 200 Msp2 (P44)-positive morulae were scored for Asp14 and OmpA per condition. Confocal microscopic examination using anti-Asp14 or anti-OmpA in conjunction with antiserum against constitutively expressed Msp2 (P44) revealed that 100.0% of morulae (intravacuolar Aph colonies) in each of the three cell lines was Asp14-positive. OmpA was detected in 100.0% and 48.6±15.9% of moruale in HL-60 and RF/6A cells, respectively, but was detected in only 7.0±3.5% of morulae in ISE6 cells (results were statistically significant, $p<0.001$). Anti-OmpA binding to intracellular Aph organisms yielded a ring-like staining pattern on the periphery of each bacterium that overlapped with signal corresponding to the confirmed surface protein, Msp2 (P44)(data not shown). The anti-OmpA staining pattern was similar to that of another confirmed Aph surface protein, Asp62. Anti-Asp14 staining was more uniformly distributed over the bacterial cells and exhibited partial overlap with Msp2 (P44) (data not shown).

Example 9. Surface Localization of OmpA and Asp14

Figure 4A:
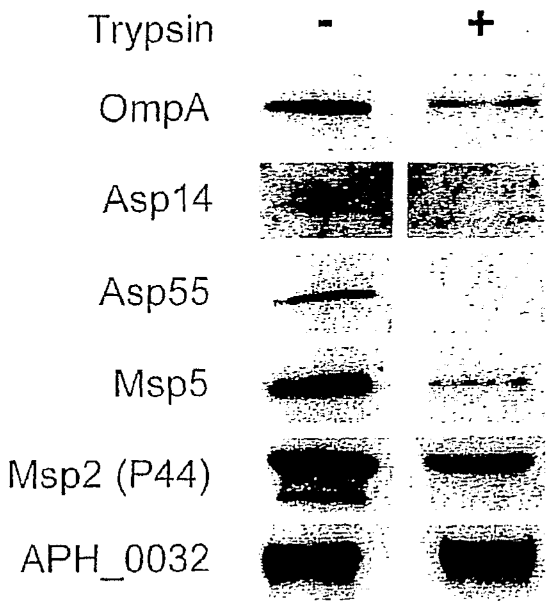
FIGS. 4A and B. Trypsin treatment abolishes detection of Aph surface proteins and surface proteins Asp14 and OmpA are detected in Aph DC organisms.
Figure 4B:
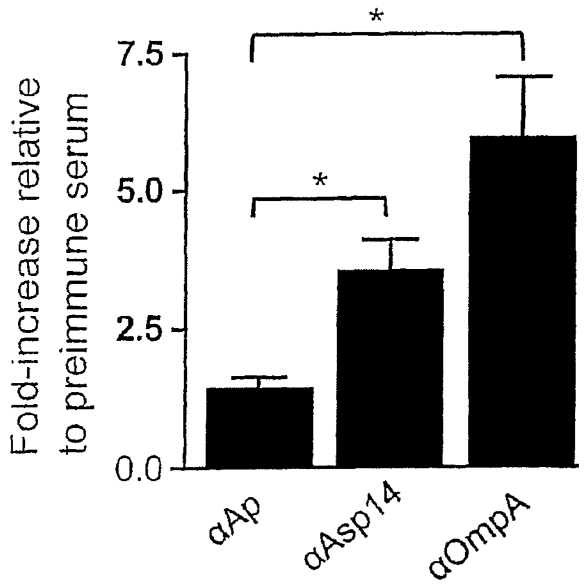
Figure 5A:
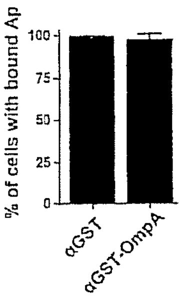
FIG. 5A-D. Anti-OmpA does not disrupt bacterial cellular adherence or bacterial interaction with PSGL-1, but does partially neutralize Aph infection of HL-60 cells.
Figure 5B:
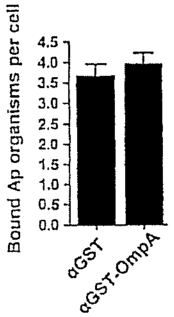
Figure 5C:
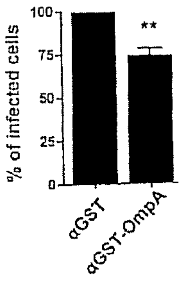
Figure 5D:
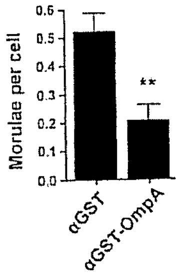

To assess surface presentation of OmpA and Asp14, intact Aph DC organisms were incubated with trypsin followed by solubilization, western blotting, and screening with anti-OmpA or anti-Asp14 to determine if immunoaccessible domains of either target protein are presented on the bacterial surface, shown in FIGS. 4A and B. In FIG. 4A, Intact DC bacteria were incubated with trypsin or vehicle control, lysed in RIPA buffer, fractionated by SDS-PAGE, and immunoblotted. Western blots were screened with antisera targeting OmpA, Asp55, Msp5, Asp14, Msp2 (P44), or APH_0032. Data are representative of two experiments with similar results. In FIG. 4B, Transgenic Aph organisms expressing GFP were incubated with preimmune mouse serum, mouse anti-Asp14 or anti-OmpA, or serum recovered from an Aph infected mouse. Primary antibodies were detected with anti-mouse IgG conjugated to Alexa fluor 647.

Flow cytometry was used to determine the percentage of Alexa fluor 647- and GFP-positive DC organisms per sample. The fold-increases in the percentages of Alexa fluor 647-positive, GFP-positive DC organisms for each sample relative to preimmune serum are provided. Results presented are the means±SD of three experiments. Statistically significant (*, $p<0.05$) values are indicated. Positive control antisera targeted Asp55, Msp2 (P44), and Msp5. Negative control antiserum was specific for API-10032, which is an Aph effector and is not a surface protein. Anti-Asp55 is specific for a peptide epitope of a surface-exposed loop of the target protein. Considerably less detection of Asp55, OmpA, Asp14, and Msp5 was observed for trypsin-treated than for vehicle control-treated bacteria, whereas Msp2 (P44) signal intensity was partially reduced and no loss in APH_0032 signal resulted (FIG. 4A). As a complementary approach to verify surface presentation of OmpA and Asp14, transgenic Aph DC organisms expressing GFP were recovered from sonicated HL-60 cells and screened with anti-OmpA, anti-Asp14, or control antisera using flow cytometry. Serum from an Aph infected mouse recognized 1.9+0.8-fold more organisms than preimmune mouse serum (FIG. 4B). Anti-OmpA and anti-Asp14 recognized 5.0±2.9- and 4.9±2.7-fold more Aph organisms expressing GFP than preimmune mouse serum (FIG. 4B).

Example 10. Pretreatment of Aph with Anti-OmpA Reduces Infection of HL-60 Cells

Because OmpA is exposed on the Aph surface, we determined if treating DC organisms with heat-inactivated anti-OmpA serum prior to incubation with HL-60 cells alters bacterial adhesion to or infection of host cells. Anti-OmpA had no effect on bacterial adhesion, but significantly reduced infection (FIG. 5A-D). Pretreatment of bacteria with mouse polyclonal anti-GST serum had no effect on binding or infection.

Example 11. In Silico Analyses of Aph OmpA and Comparisons with Homologs from other Anaplasmataceae pathogens Since anti-OmpA inhibits Aph infection, we hypothesized that OmpA may contribute to infection of host cells. We performed in silico analyses to identify the predicted extracellular region of OmpA, which would putatively contain any receptor-binding domain, and to assess whether this and other regions of OmpA are conserved among its homologs from other Rickettsiales bacteria. The OmpA N-terminal region extending through to amino acid 86 is predicted to comprise the only extracellular domain, and amino acids 87-102 are predicted to form a transmembrane helix (FIG. 6A). A multiple sequence alignment revealed that the Aph OmpA sequence has several shaded stretches that exhibit identity or similarity with its homologs from other *Anaplasma* spp. and *Ehrlichia* spp. (FIG. 6A).

The PHYRE$^2$ server (see the website at sbg.bio.ic.ac.uk/phyre2) predicts tertiary structures for protein sequences and threads the predicted structures on known crystal structures. The highest scoring model for Aph OmpA that exhibits the greatest amino acid sequence identity with the crystal structure on which it was threaded, *Bacillus* chorismate OmpA, is presented in FIG. 6B. Amino acids 44-56 are predicted to form a surface-exposed helix and loop, as indicated by arrows. The peptide K[IV]YFDaxK (where "a" and "x" represent a non-polar and any amino acid, respectively), that corresponds to Aph OmpA residues 49-56 is conserved among *Anaplasma* spp. and *Ehrlichia* spp. OmpA proteins.

Example 12. Interactions of GST-OmpA with Endothelial Cells

We tested if we could detect GST-OmpA binding to RF/6A cells. Since OmpA proteins of Aph and *O. tsutsugamushi* exhibit regions of identity, *O. tsutsugamushi* infects endothelial cells, and it is unknown whether *O. tsutsugamushi* OmpA interacts with endothelial cells, we also assessed whether GST-tagged *O. tsutsugamushi* OmpA (GST-OtOmpA) bound to RF/6A cells. Negative controls for cellular adhesion were GST alone and GST-tagged APH_1387 amino acids 112-579 (GST-APH_$1387_{112-579}$). APH_1387 is an Aph effector that associates with the bacterium's vacuolar membrane. APH_1387 amino acids 112-579 lack the transmembrane domain that is required for interacting with eukaryotic cell membranes (unpublished observation). GST-OmpA but not GST bound to RF/6A cells (data not shown). Neither GST-APH_$1387_{112-579}$ nor GST-OtOmpA bound the host cells. GST-tagged Aph OmpA binding to RF/6A cells is therefore specific because recombinant form of neither an irrelevant Aph protein nor OmpA derived from another Rickettsiales bacterium binds to RF/6A cells. GST-OmpA binding to RF/6A cells does not involve PSGL-1 or $sLe^x$ since antibodies targeting either receptor fail to bind RF/6A cells (data not shown) and a previous report demonstrated that endothelial cells do not express PSGL-1. We examined if preincubating RF/6A cells with GST-OmpA competitively inhibits Aph binding or infection. GST-OmpA but not GST significantly inhibited infection (data not shown). Neither recombinant protein inhibited Aph adhesion (data not shown).

Example 13. Sialidase and Trypsin Treatments Markedly Reduce GST-OmpA Binding to Host Cells Enzymatic removal of sialic acid residues from myeloid cell surfaces pronouncedly inhibits Aph binding and infection. Sialic acid residues are also important for Aph infection of RF/6A cells, as pretreatment of RF/6A cells with sialidases reduced Aph infection by 52.8±1.4% (data not shown). The MAL-II lectin recognizes sialic acids that are attached to galactose units via α2,3-linkages. The SNA lectin preferentially binds to sialic acid attached to galactose in an α2,6-linkage. Sialidase treatment abolished MAL-II binding and markedly reduced SNA binding, indicating that the sialidase cocktail completely removed α2,3-linked sialic acids and partially removed α2,6-linked sialic acids. GST-OmpA did not bind as well to RF/6A cells that had been incubated in the vehicle control buffer as compared to other buffers. Nonetheless, GST-OmpA binding to sialidase-treated cells was reduced. These results suggest that OmpA recognizes α2,3-linked sialic acids but is also capable of interacting with α2,6-linked sialic acids. Pretreatment of RF/6A cells with trypsin, which would effectively digest protein and glycoprotein receptors, including terminally sialylated glycoproteins, nearly eliminated GST-OmpA binding.

Example 14. GST-OmpA Competitively Inhibits Aph Infection of HL-60 Cells

Figure 7A:
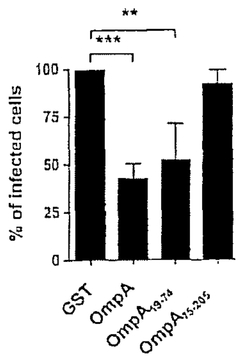
FIGS. 7A and B. Pretreatment of Aph with anti-OmpA reduces infection of HL-60 cells.
Figure 7B:
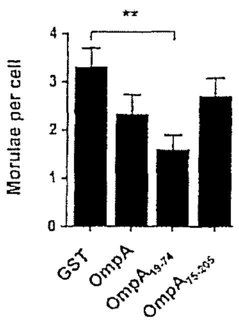

To define the relevance of OmpA to Ap hinfection of human myeloid cells and to delineate the OmpA region that is critical for cellular invasion, we examined if preincubating HL-60 cells with GST-OmpA or fragments thereof inhibits infection by Aph DC organisms. GST-tagged full-length OmpA and $OmpA_{19-74}$, which comprises the majority of the predicted extracellular domain, but not GST-$OmpA_{75-205}$ or GST alone had no effect on adhesion (data not shown), but significantly inhibited infection (FIGS. 7A and B).

Example 15. GST-OmpA Inhibits Aph Binding to $sLe^x$-Capped PSGL-1

Aph binding to the α2,3-linked sialic acid determinant of $sLe^x$ is necessary for the bacterium to optimally engage $sLe^x$-capped PSGL-1 and leads to infection of myeloid cells. Since GST-OmpA recognizes α2,3-sialic acid and competitively inhibits Aph infection of HL-60 cells, we rationalized that GST-OmpA binds to α2,3-sialic acid of $sLe^x$. To test this, we incubated PSGL-1 CHO cells with GST-OmpA in an attempt to block Aph access to the α2,3-sialic acid determinant of $sLe^x$-capped PSGL-1 and thereby inhibit bacterial adherence to these cells. As a positive control for preventing bacterial access to the α2,3-linked sialic acid determinant of $sLe^x$, PSGL-1 CHO cells were incubated with CSLEX1. PSGL-1 CHO cells treated with GST or mouse IgM served as negative blocking controls. GST-OmpA reduced Aph binding to $sLe^x$-modified PSGL-1 by approximately 60% relative to GST alone, and this degree of inhibition was comparable to the blocking afforded by CSLEX1 (data not shown).

Figure 8:
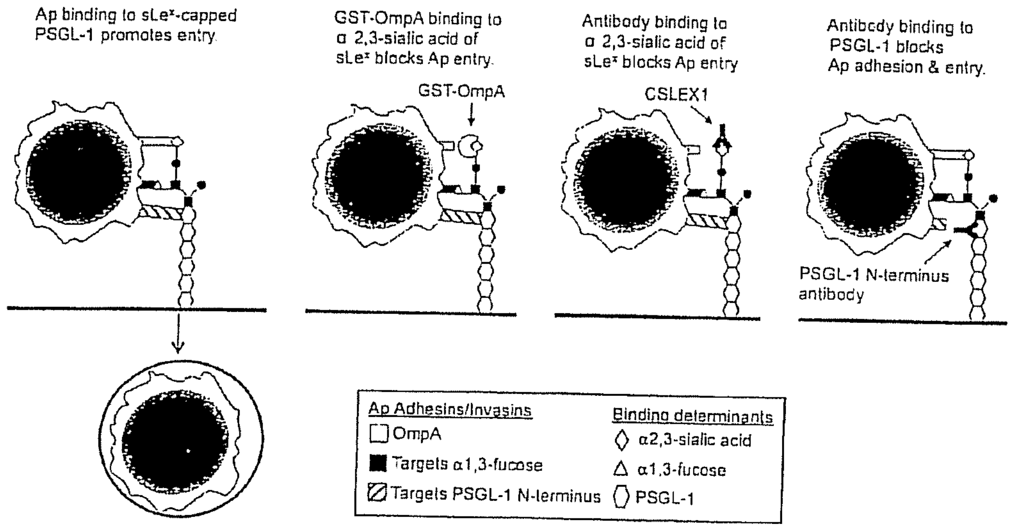
FIG. 8. Model for how Aph OmpA interacts with its receptor to promote infection of host cells FIG. 9A-D. Pretreatment of Aph with anti-Asp14 reduces infection of HL-60 cells.
Figure 9A:
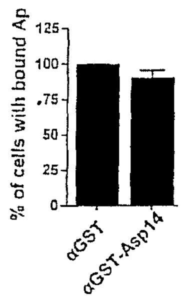
Figure 9B:
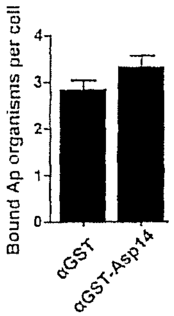
Figure 9C:
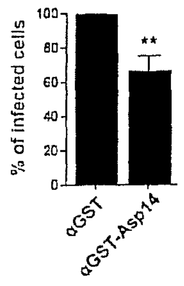
Figure 9D:
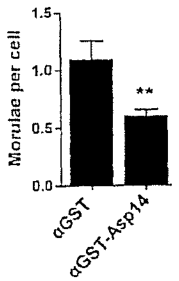

Example 16. Model for how Aph OmpA Interacts with its Receptor to Promote Infection of Host Cells (FIG. 8)

Sialic acid has long been known to be a determinant that is important for Aph infection. This study demonstrates that OmpA targets sialylated glycoproteins to promote Aph infection. Our results fit the model that Aph employs multiple surface proteins to bind three determinants of $sLe^x$-capped PSGL-1 to infect myeloid cells. When these data are examined in the context of results obtained from our own studies and others, the respective contributions of sialic acid, α1,3-fucose, and PSGL-1 N-terminal peptide to Aph binding and entry become clearer. Treating myeloid cells with CSLEX1 to block *A. phagocytophilum* binding to the sialic acid determinant of $sLe^x$ markedly reduces infection, a phenomenon that is analogous to the inhibitory action of GST-OmpA. Moreover, the inhibitory effects of CSLEX1 and GST-OmpA on Aph binding to PSGL-1 CHO cells are nearly identical. Therefore, while OmpA is capable of binding sialic acid determinants of varied sialylated glycans, its specific interaction with the sialic acid residue of $sLe^x$ is important for bacterial entry. GST-OmpA and GST-$OmpA_{19-74}$ binding to host cells reduces Aph infection of HL-60 cells by approximately 52 and 57%, respectively, but has no inhibitory effect on bacterial adhesion. Thus, bacterial recognition of the PSGL-1 N-terminus, α1,3-fucose of $sLe^x$, and perhaps $sLe^x$-/PSGL-1-independent interactions that still occur when the OmpA-sialic acid interaction is disrupted facilitate bacterial binding but lead to sub-optimal infection. Antibodies that block access to the PSGL-1 N-terminal peptide determinant prevent bacterial binding and infection. Therefore, the collective avidity mediated by OmpA interaction with sialic acid together with Aph recognition of α1,3-fucose is insufficient to promote bacterial adhesion and, consequently, entry in the absence of PSGL-1 recognition.

Example 17. Pretreating Aph with Anti-Asp14 Inhibits Infection of HL-60 Cells

Since Asp14 is a surface protein, we examined if incubating Aph DC organisms with heat-inactivated Asp14 antiserum prior to adding them to HL-60 cells inhibited bacterial binding or infection. Anti-Asp14 had no effect on Aph adhesion, but reduced infection by approximately 33% and lowered the mean number of morulae per cell by approximately 54%, (FIGS. 9A-D). Inhibition was specific to Asp14 antiserum, as GST antiserum did not alter bacterial binding or infection.

Example 18. The Asp14 C-Terminal Region Binds Mammalian Host Cells

Since Asp14 is an exposed outer membrane protein and anti-Asp14 reduces Aph infection, we rationalized that Asp14 may interact with mammalian host cell surfaces to promote infection. To test this possibility and to identify the Asp14 region that is sufficient for optimal adherence, we examined if GST-tagged Asp14 or portions thereof bind to RF/6A cells. GST alone and GST-tagged APH_1387 amino acids 112-579 (GST-$APH\_1387_{112-579}$) were negative controls. APH_1387 is an Aph protein that localizes to the pathogen's vacuolar membrane and does not associate with the host cell surface. GST-Asp14 but neither GST nor GST-$APH\_1387_{112-579}$ bound to RF/6A cells (FIG. 9A-D). The binding domain is carried on the Asp14 C-terminal half, as GST-$Asp14_{65-124}$ but not GST-$Asp14_{1-64}$ exhibited binding. GST-$Asp14_{1-100}$ and GST-$Asp14_{1-112}$ were unable to bind RF/6A cells (data not shown). Thus, Asp14 residues 101-124 contain the minimal region that is sufficient to facilitate adhesion to mammalian cell surfaces.

Figure 10A:
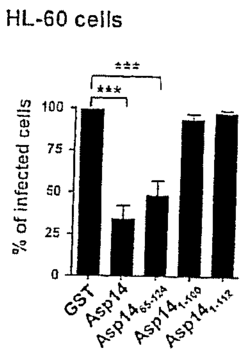
FIG. 10A-D. Asp14 residues 101-124 are required to competitively inhibit Aph infection of mammalian host cells.
Figure 10B:
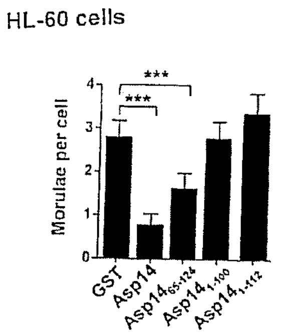
Figure 10C:
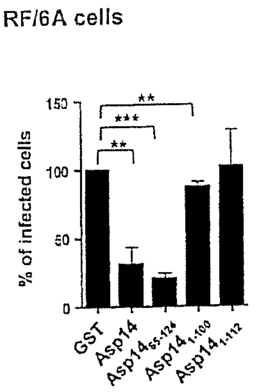
Figure 10D:
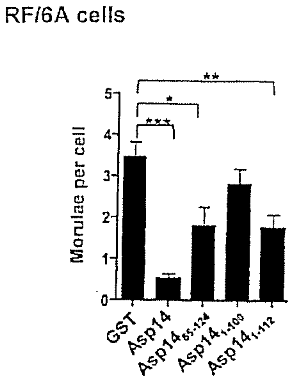

Example 19. GST-Asp14 Requires Asp14 Residues 101-124 to Competitively Inhibit *A. phagocytophilum* Infection of Mammalian Host Cells We next determined if GST-tagged Asp14 or fragments thereof could inhibit *A. phagocytophilum* infection. GST-Asp14 and GST-$Asp14_{65-174}$ each significantly reduced infection of HL-60 and RF/6A cells relative to GST alone (FIG. 10A-D). GST-$Asp14_{1-100}$ and GST-$Asp14_{1-112}$ had no effect on infection of HL-60 cells (FIGS. 10A and B). GST-$Asp14_{1-112}$ did not lower the percentage of infected RF/6A cells, but reduced the mean number of morulae per RF/6A cell comparably to GST-$Asp14_{65-174}$ (FIGS. 10C and D). Pretreating host cells with GST-Asp14 fusion proteins prior to incubation with bacteria failed to inhibit *A. phagocytophilum* binding (data not shown). Thus, *A. phagocytophilum* binding to mammalian host cells is Asp14-independent, but Asp14 is important for bacterial invasion.

Example 20. The Asp14 C-Terminus is Positively Charged and Residues 101-115 Constitute a Conserved Domain Among Homologs from *Anaplasma* and *Ehrlichia* Species Based on our results, a domain that lies within Asp14 amino acids 101-124 is involved in mediating interactions with host cells that promote *A. phagocytophilum* infection. To determine if this or any other Asp14 region is conserved among Anaplasmataceae members, we aligned the primary amino acid sequences of Asp14 with its homologs from two *A. marginale* strains and three monocytotropic *Ehrlichia* species. Doing so identified two conserved regions, the first of which corresponds to Asp14 amino acids 19-61 (FIG. 11). The second conserved region aligns with Asp14 residues 101-115. The consensus sequence for this region among the *Anaplasma* and *Ehrlichia* spp. Asp14 homologs is L[RK]aIKKR[IL]LRLERxV, where "a" and "x" represent a non-polar and any amino acid, respectively. Beginning at tyrosine 116, the Asp14 C-terminus bears no sequence homology to its *A. marginale* and ehrlichiae counterparts. The Asp14 C-terminus (amino acids 101-124) has a charge of +4.91 despite the entire protein sequence having a charge of −3.10. A similar trend is observed when the charges of the Asp14 homologs' C-termini and entire protein sequences are examined.

Figure 12A:
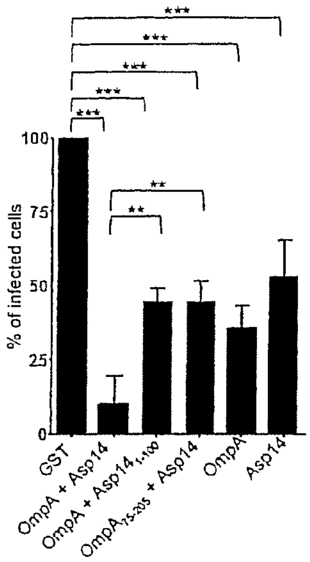
FIGS. 12A and B. Recombinant forms of Asp14 and OmpA cooperatively block Aph infection of HL-60 cells, either as full-length proteins or fragments identified as critical conserved effector domains.
Figure 12B:
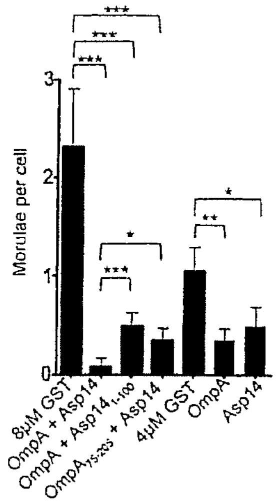

Example 21. GST-Asp14 and GST-OmpA Together More Pronouncedly Inhibit *A. phagocytophilum* Infection of HL-60 Cells than Either Protein Alone We examined whether we could improve upon the protection against *A. phagocytophilum* infection afforded by GST-Asp14 or GST-OmpA by pretreating HL-60 cells with both recombinant proteins. Consistent with previous results, 35.5±7.4% of GST-OmpA-treated and 53.2±11.8% of GST-Asp14-treated HL-60 cells became infected (FIG. 11A). However, HL-60 cells that had been preincubated with both GST-Asp14 and GST-OmpA were better protected against *A. phagocytophilum* infection, as only 9.9±9.4% of cells developed morulae. To prove that the synergistic reduction in infection was specific to the combinatorial effect of GST-Asp14 and GST-OmpA and not simply due to the presence of excess recombinant protein, we treated HL-60 cells with GST-Asp14 and GST-OmpA, GST-Asp$14_{1-100}$ (does not block infection; data not shown) and GST-OmpA, or GST-Asp14 and GST-Omp$A_{75-205}$ (does not block infection). HL-60 cells treated with GST-Asp$14_{1-100}$ and GST-OmpA or GST-Asp14 and GST-Omp$A_{75-205}$ exhibited reductions in infection and bacterial load comparable to cells treated with GST-Asp14 or GST-OmpA alone (FIGS. 12A and B). HL-60 cells treated with GST-Asp14 and GST-OmpA exhibited an approximate 4.5-fold reduction in the percentage of infected cells relative to cells treated with either GST-Asp$14_{1-100}$ and GST-OmpA or GST-Asp14 and GST-Omp$A_{75-205}$ (FIG. 12A).

Example 22. Peptide Antisera Blocking Reveals that the OmpA Invasin Domain Lies within Amino Acids 59-74

Figure 13A:
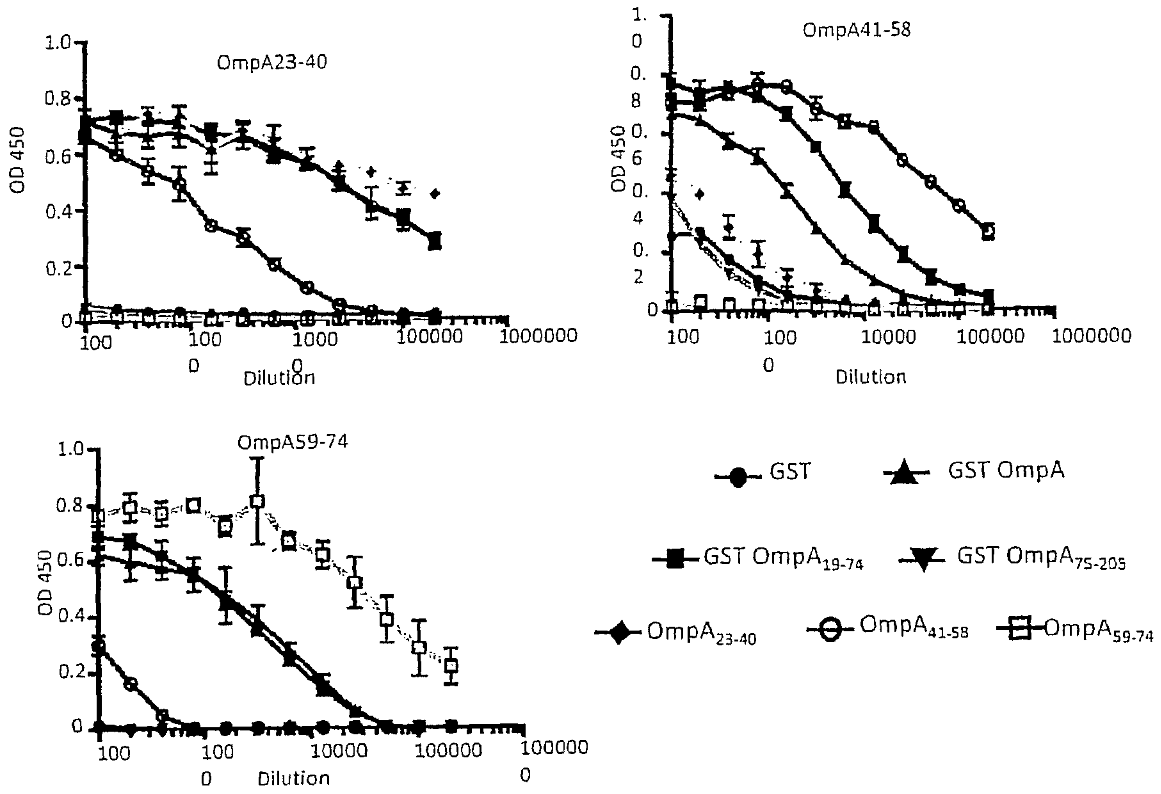
FIG. 13A-C. Peptide antisera blocking reveals that the OmpA invasin domain lies within amino acids 59-74.
Figure 13B:
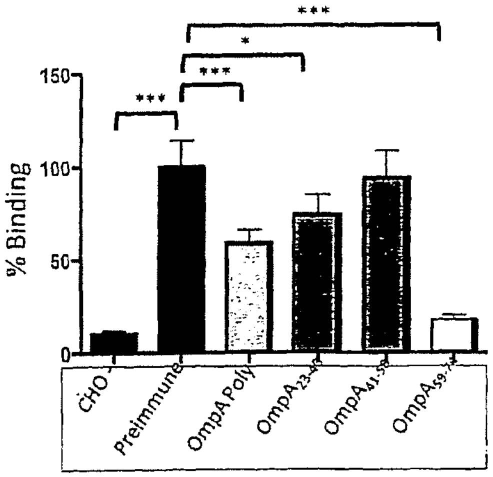
Figure 13C:
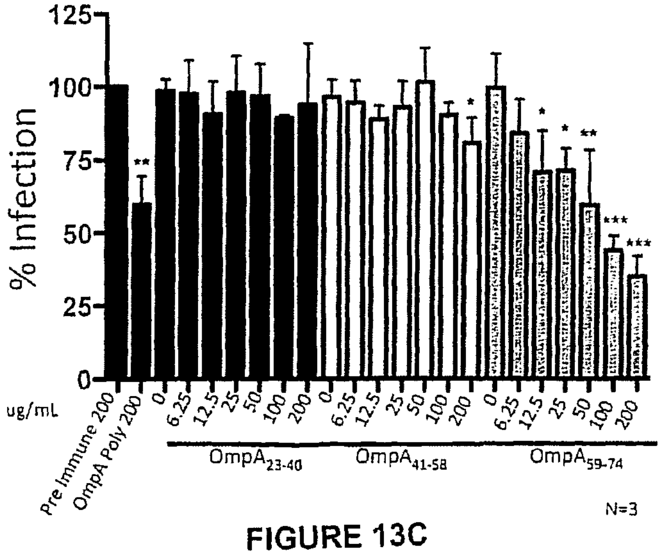

We had rabbit antiserum raised against peptides corresponding to OmpA amino acids 23-40, 41-58, and 59-74. We confirmed by ELISA that each serum is specific for recombinant OmpA and only the peptide against which it was raised (FIG. 13A). Pretreating *A. phagocytophilum* with serum specific for Omp$A_{59-74}$ but neither of the other two peptide sera significantly inhibited *A. phagocytophilum* infection of host cells in vitro (FIG. 13B). Also, treatment of bacteria with Omp$A_{59-74}$ serum but not Omp$A_{23-40}$ serum or Omp$A_{41-58}$ serum prevents *A. phagocytophilum* binding to its known receptor, sialylated PSGL-1 (FIG. 13C).

Please note that even thought amino acids 59-74 are most important for OmpA to promote infection that amino acids 23-58 are predicted to be presented on the *A. phagocytophilum* surface and could therefore be a component of a protective vaccine.

Example 23. Linker Insertions Disrupt the Ability of GST-OmpA to Antagonize *A. phagocytophilum* Infection of Mammalian Host Cells and Support that the Invasin Domain Lies within Amino Acids 59-74

Figure 15:
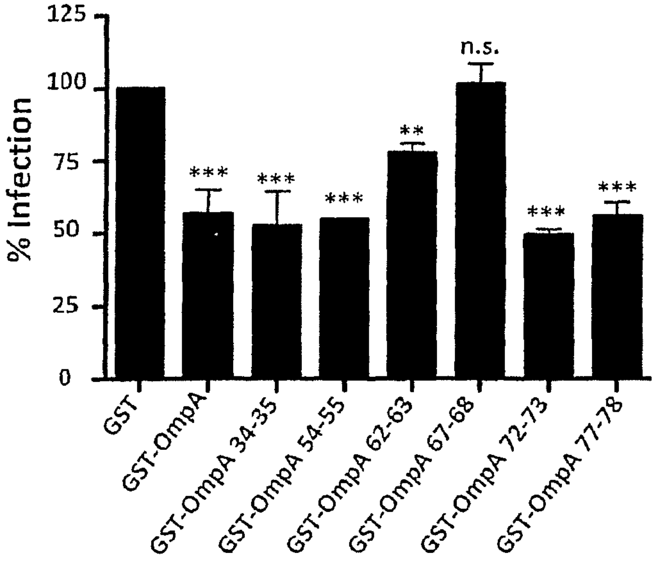
FIG. 15. Percent of infection using linker insertion mutants of OmpA.

We also generated a series of glutathione-S-transferase (GST)-tagged OmpA proteins having an insertion of 5 amino acids (CLNHL) at defined locations. The purpose of the insertion of the amino acid "linker" was to disrupt any OmpA domain that facilitates binding of the protein to host cell surfaces. Individual plasmids encoding GST-OmpA proteins carrying linker insertions between aspartate 34 and leucine 35; isoleucine 54 and glycine 55; proline 62 and glycine 63; isoleucine 67 and leucine 68; glutamate 72 and glutamine 73; or aspartate 77 and aspartate 78 were generated by PCR mutagenesis of the plasmid encoding GST-OmpA (FIG. 14). *E. coli* was transformed with each plasmid, induced to express the GST-OmpA proteins, and the proteins were purified by glutathione affinity chromatography. Adding recombinant wild-type OmpA and several OmpA insertion mutant proteins to host cells successfully inhibited *A. phagocytophilum* infection of host cells (FIG. 15). These data indicate that the OmpA proteins were still able to bind to the OmpA receptor and competitively inhibit bacterial access to the receptor. However, only the GST-OmpA protein bearing a linker insertion between isoleucine 67 and leucine 68 lost the ability to competitively inhibit infection, which indicates that disruption of the region encompassed by amino acids 67 and 68 and its flanking amino acids abrogates the ability of OmpA to bind its receptor.

Figure 16:
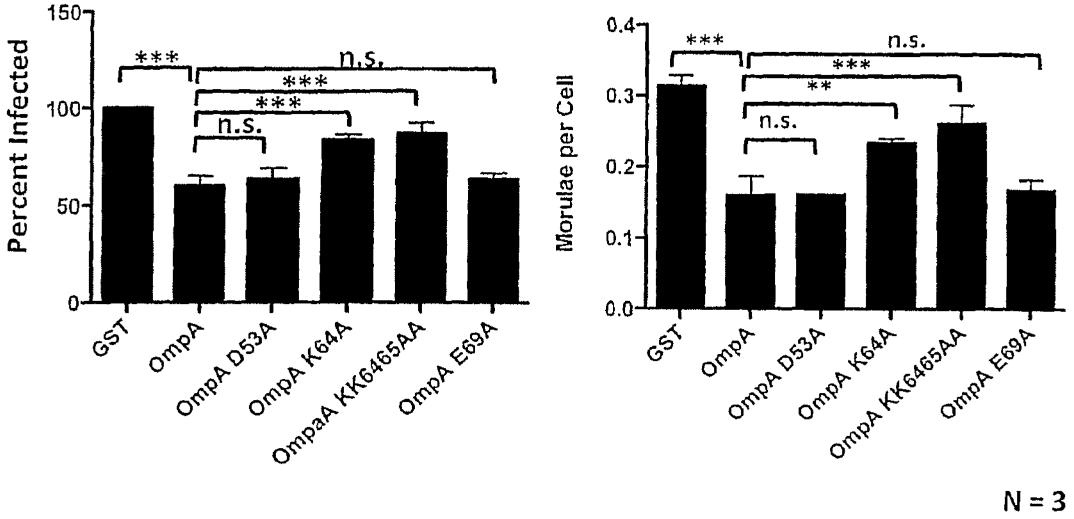
FIG. 16. Percent of infection in alanine substitution experiments that identified that OmpA aa59-74 are important for infection.

Example 24. Alanine Substitution Experiments Identify that Amino Acids within OmpA Aa59-74 are Important for Infection To identify specific amino acids that are important for OmpA to bind to and mediate infection of host cells, we performed PCR mutagenesis to create plasmids encoding GST-OmpA bearing single or double alanine substitutions at D53, K64, E69, K60A, K65, E72A, KK6065AA, KK6064AA, KKK606465AAA, or K64 and K65. The proteins were purified and added to mammalian host cells. Next, *A. phagocytophilum* bacteria were incubated with the host cells. GST-OmpA, GST-OmpAD53A, and GST-OmpA each significantly inhibited infection whereas GST alone did not (FIG. 16). The abilities of GST-OmpAK64A and GST-OmpAKK6465AA to antagonize infection were significantly less than that of GST-OmpA, which indicates that OmpA amino acids 64 and 65 are important for OmpA to properly bind to host cells and for recombinant OmpA to serve as a competitive agonist against *A. phagocytophilum* infection.

Example 25. In Silico Modeling of OmpA Interactions with its Receptor

The tertiary structure for *A. phagocytophilum* OmpA was predicted using the PHYRE$^2$ (Protein Homology/analogy Recognition Engine, version 2.0) server (see the website at sbg.bio.ic.ac.uk/phyre2). The PHYRE$^2$ server predicts tertiary structures for protein sequences and threads the predicted structures on known crystal structures. The highest scoring model predicts that amino acids 59-74 to be part of a surface-exposed helix that would be available to interact with other molecules (data not shown). Indeed, when the autodock vina algorithm (http://vina.scripps.edu) is used to assess whether OmpA binds to its known receptor, sialic acid of the sialyl Lewis x antigen, the lowest free energy models predict that Lysine 64 interacts with sialic acid (data not shown).

Example 26. The Asp14 Invasin Domain Lies within Amino Acids 113-124

Figure 17A:
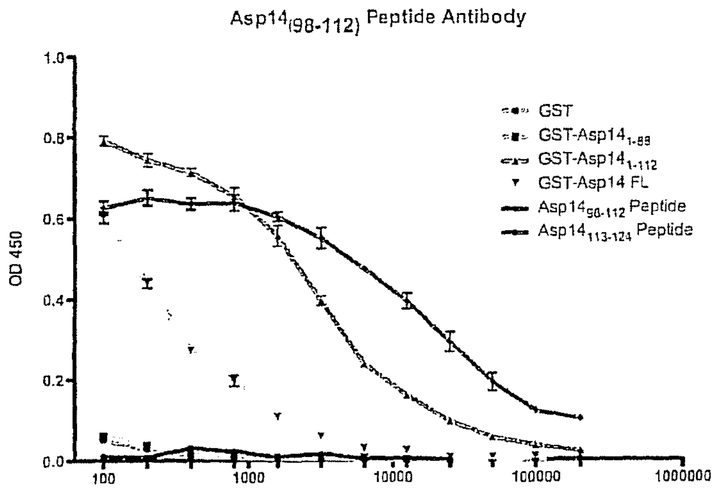
FIGS. 17A and B. ELISA results showing the specificity of antiserum raised against Asp14 aa98-112 or aa113-124.
Figure 17B:
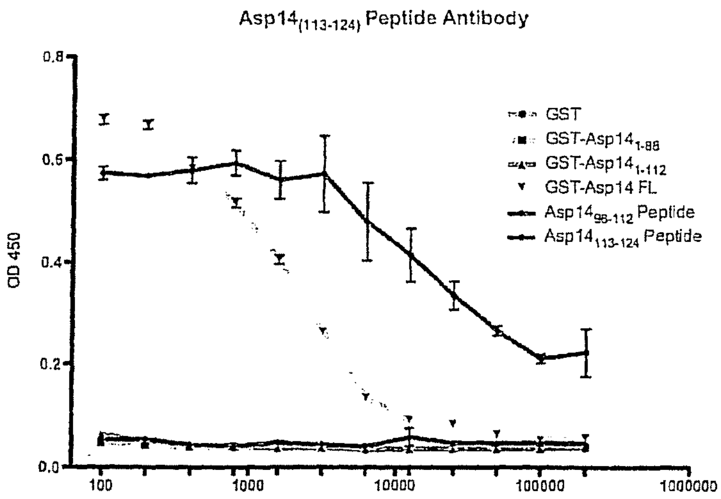
Figure 18:
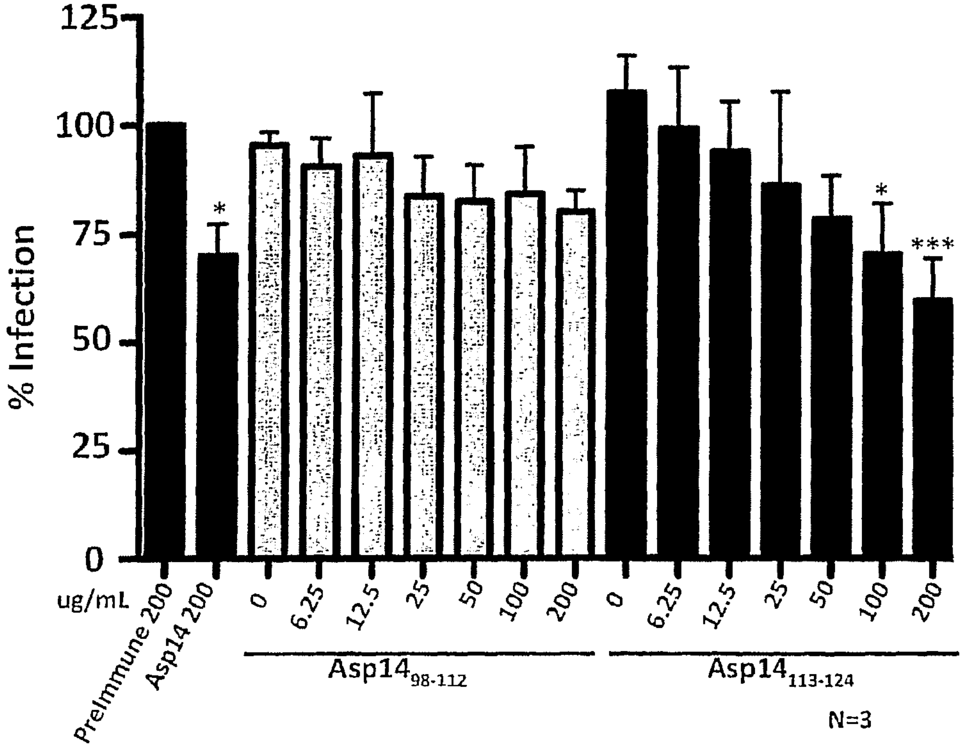
FIG. 18. Percent of bacterial infection inhibited by pretreatment of Aph with antiserum specific for Asp14 invasin domain.

The structure of Asp14 is not known and it cannot be predicted because it bears no semblance to any crystal structure. Next, we set out to identify the region of Asp14 that is important for infection. We knew that the Asp14 invasin domain lies within amino acids 101-124. We had rabbit antiserum raised against peptides corresponding to Asp14 amino acids 101-112 and 113-124. We confirmed by ELISA that each serum is specific for recombinant Asp14 and only the peptide against which it was raised (FIGS. 17A and B). Pretreating Aph with serum specific for $Asp14_{113-124}$ but not $Asp14_{101-112}$ significantly inhibited bacterial infection of host cells in vitro (FIG. 18).

Figure 19:
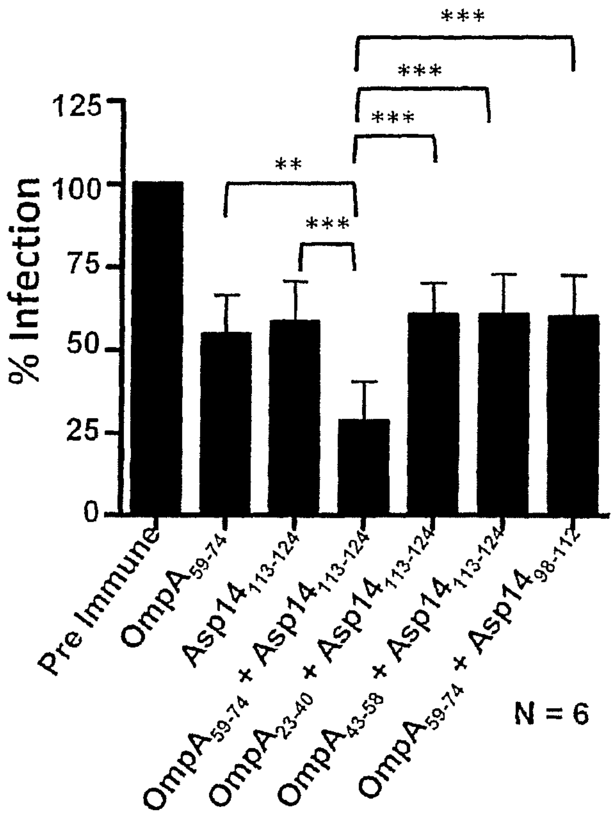
FIG. 19. Percent of infection reduced by antisera specific for the OmpA invasin domain, Asp14 invasin domain, or combinations thereof.

Example 27. Treating Aph with Antibodies Targeting OmpA Aa59-74 and Asp14 Aa113-124 Together Pronouncedly Inhibits Infection of Mammalian Host Cells Treating Aph organisms with anti-$OmpA_{59-74}$ or anti-$Asp14_{113-124}$ significantly inhibits infection of mammalian host cells in vitro (FIG. 19). Treating the bacteria with both anti-$OmpA_{59-74}$ and $Asp14_{113-124}$ even more pronouncedly inhibits infection.

Example 28. Aph OmpA and *A. Marginale* OmpA Share B-Cell Epitopes

Figure 20A:
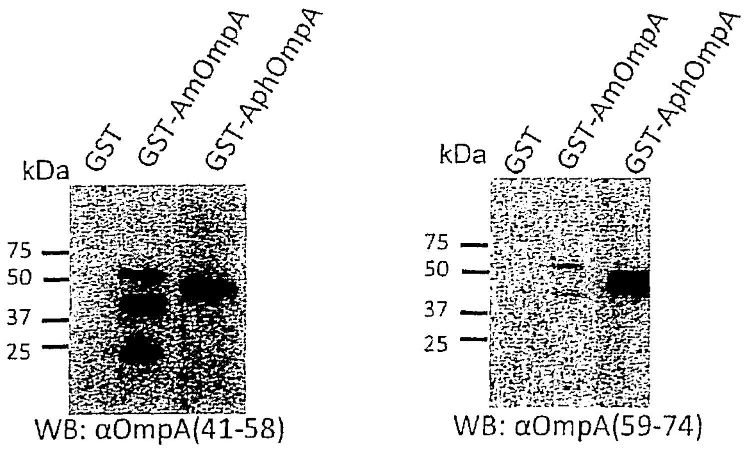
FIGS. 20A and B. Western blot and ELISA showing that *A. phagocytophilum* OmpA and *A. marginale* OmpA share B-cell epitopes.
Figure 20B:
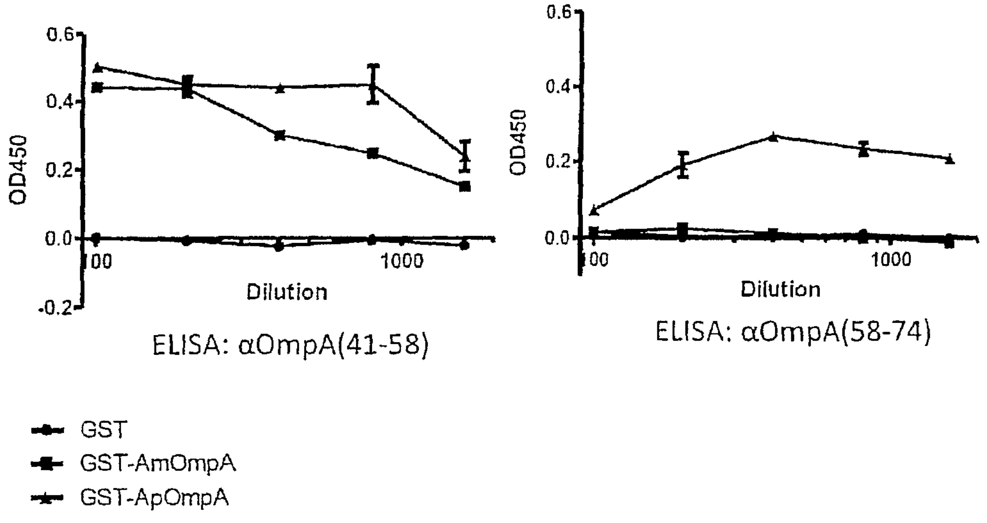

*A. marginale* infects bovine red blood cells and costs the cattle industry hundreds of millions of dollars annually. *A. marginale* OmpA and Aph OmpA, though not identical, are very similar, including the region corresponding to Aph OmpA aa19-74 (SEQ ID NO:05). Therefore, a vaccine preparation that includes SEQ ID NO:05, alone or in combination with other sequences of the invention is also effective in providing protection against *A. marginale* infection. GST-tagged Aph OmpA, GST-tagged *A. marginale* OmpA (AM854), and GST alone were subjected to SDS-PAGE and transferred to nitrocellulose membrane. The blots were screened with serum from a cow that had been infected with *A. marginale* or with serum from a cow that had been immunized with purified *A. marginale* outer membrane proteins. Both sera recognized GST-tagged OmpA proteins not GST (data not shown), thereby demonstrating that OmpA proteins from Aph and *A. marginale* share B cell epitopes. Serum raised against Aph OmpA amino acids 41-58 or 59-74 recognize GST-*A. marginale* OmpA (AM854) in both Western blot (FIG. 20A) and ELISA (FIG. 20B).

Example 28 Immunizing Against OmpA and/or Asp14 Protects Mice from Tick-Mediated Aph Infection C3H/HeJ mice (female, 4-6 weeks of age) are immunized with 10 ug of GST-OmpA (full length), GST-$OmpA_{19-74}$, GST-Asp14; 10 ug each of GST-OmpA and GST-Asp14; or 10 ug each of GST-$OmpA_{19-74}$ and GST-Asp14 in Complete Freund's Adjuvant. At two and four weeks following the initial immunization, mice are boosted with the same amounts and combinations of each antigen in Incomplete Freund's Adjuvant.

Alternatively, C3H/HeJ mice are immunized with 50 ug of KLH-conjugated peptides corresponding to $OmpA_{23-40}$, $OmpA_{41-58}$, $OmpA_{59-74}$, $Asp14_{100-117}$, $AsP14_{113-124}$ and every possible combination thereof. The same adjuvants and immunization schedule as in the preceding paragraph may be followed.

Five days following the second boost, aliquots of serum from each mouse are tested via ELISA to confirm that a humoral immune response was mounted against OmpA, Asp14, and the respective portions thereof. At one week following the second boost, three Aph infected *Ixodes scapularis* ticks are placed on each mouse and allowed to feed for 48 hours to allow for transmission of the bacteria into the mice. On days 3, 8, and 12 post tick feeding, peripheral blood is collected. DNA isolated from the blood is subjected to quantitative PCR using primers targeting the Aph 16S rDNA and murine Beta-actin to determine the pathogen load in the peripheral blood (data not shown). This protocol is also useful when adjuvants suitable for innocculating dogs, humans, or other mammals are used for respective species.

Example 29. Immunizing Against OmpA and/or Asp14 Protects Mice from Syringe Inoculation of Aph Infection C3H/HeJ mice (female, 4-6 weeks of age) are immunized with 10 ug of GST-OmpA (full length), GST-$OmpA_{19-74}$, GST-Asp14; 10 ug each of GST-OmpA and GST-Asp14; or 10 ug each of GST-$OmpA_{19-74}$ and GST-Asp14 in Complete Freund's Adjuvant. At two and four weeks following the initial immunization, mice are boosted with the same amounts and combinations of each antigen in Incomplete Freund's Adjuvant.

Alternatively, C3H/HeJ mice are immunized with 50 ug of KLH-conjugated peptides corresponding to $OmpA_{23-40}$, $OmpA_{41-58}$, $OmpA_{59-74}$, $Asp14_{100-112}$, $Asp14_{113-124}$ and every possible combination thereof. The same adjuvants and immunization schedule as in the preceding paragraph may be followed.

Five days following the second boost, aliquots of serum from each mouse are tested via ELISA to confirm that a humoral immune response was mounted against OmpA, Asp14, and the respective portions thereof. At one week following the second boost, each mouse is inoculated with either 100 ul of blood from an Aph infected SCID mouse that was confirmed to be infected or 100 ul of host cell free Aph bacteria recovered from tissue cell culture. On days 3, 8, and 12 post tick feeding, peripheral blood is collected. DNA isolated from the blood is subjected to quantitative PCR using primers targeting the Aph 16S rDNA and murine Beta-actin to determine the pathogen load in the peripheral blood (data not shown).

This protocol is also useful when adjuvants suitable for innocculating dogs, humans, or other mammals are used for respective species.

In summary, OmpA and Asp14 are the first two Aph surface proteins found to be critical for infection of mammalian cells. Expression of these proteins is induced in Aph during the tick bloodmeal and during the period in which humoral immune responses are stimulated in humans and mice. Embodiments of the invention are compositions comprising OmpA and/or Asp14 sequences and methods to prevent Aph infection of humans and animals by inducing an immune response that blocks one or more of the 3 critical stages of infection: (1) the initial colonization of neutrophils and/or endothelial cells that establishes infection; (2) the dissemination stage when infected peripherally circulating neutrophils are inhibited in their microbial killing capability; and (3) the infection of endothelial cells of heart and liver. A further embodiment provides compositions and methods for diagnosis of anaplasmosis and HGA.

What is claimed is:

1. A method of protecting a subject from an *Anaplasma phagocytophilum* infection comprising administering to said subject an immunogenic composition having at least one polypeptide comprising SEQ ID NO:03.

2. The method according to claim 1, wherein said immunogenic composition comprises at least one polypeptide comprising SEQ ID NO: 3 and SEQ ID NO: 6.

3. The method of claim 1, wherein said subject is an animal and said *Anaplasma phagocytophilum* infection is anaplasmosis.

* * * * *